(12) United States Patent
Lund et al.

(10) Patent No.: US 12,071,547 B2
(45) Date of Patent: Aug. 27, 2024

(54) SULFORHODAMINE PHOSPHORAMIDITE DYES

(71) Applicant: CEPHEID, Sunnyvale, CA (US)

(72) Inventors: Kevin P. Lund, Sunnyvale, CA (US);
Dmitri Sergueev, Sunnyvale, CA (US);
Maher N. Qabar, Sunnyvale, CA (US);
Alexander Gall, Sunnyvale, CA (US)

(73) Assignee: Cepheid, Sunnyvale, CA (US)

( * ) Notice: Subject to any disclaimer, the term of this patent is extended or adjusted under 35 U.S.C. 154(b) by 110 days.

(21) Appl. No.: 17/053,683

(22) PCT Filed: May 7, 2019

(86) PCT No.: PCT/US2019/031188
§ 371 (c)(1),
(2) Date: Nov. 6, 2020

(87) PCT Pub. No.: WO2019/217470
PCT Pub. Date: Nov. 14, 2019

(65) Prior Publication Data
US 2024/0067824 A1 Feb. 29, 2024

Related U.S. Application Data

(60) Provisional application No. 62/668,109, filed on May 7, 2018.

(51) Int. Cl.
*C09B 11/24* (2006.01)
*C12Q 1/6876* (2018.01)

(52) U.S. Cl.
CPC ............ *C09B 11/24* (2013.01); *C12Q 1/6876* (2013.01)

(58) Field of Classification Search
CPC ....................................................... C09B 11/24
See application file for complete search history.

(56) References Cited

U.S. PATENT DOCUMENTS

| 5,231,191 A | 7/1993 | Woo et al. |
| 5,451,463 A | 9/1995 | Nelson |
| 9,040,674 B2 | 5/2015 | Benson et al. |
| 2005/0170363 A1 | 8/2005 | Reddington et al. |

FOREIGN PATENT DOCUMENTS

| CN | 101454315 A | 6/2009 |
| WO | 2011123820 A2 | 10/2011 |

OTHER PUBLICATIONS

Corrie et al, Ring-chain interconversion of sulforhodamine-amine conjugates involves an unusually labile CN bond and allows measurement of sulfonamide ionization kinetics, 2008, Journal of Physical Organic Chemistry, 21(4), p. 286-298 (Year: 2008).*
Office Action mailed Oct. 4, 2021, in corresponding European Patent Application No. 19725532.6 filed May 7, 2019, 6 pages.
Corrie, J.E.T., et al., Chemistry of Sulforhodamine-Amine Conjugates, Bioconjugate Chemistry, 12(2):186-194, 2001.
International Search Report and Written Opinion, mailed Aug. 5, 2019, in corresponding International Patent Application No. PCT/US2019/031188, 17 pages.
Office Action mailed Apr. 11, 2022, in corresponding Indian Patent Application No. 202037052780 filed May 7, 2019, 8 pages.
Office Action mailed Mar. 8, 2022, in corresponding Chinese Patent Application No. 2019800308121 filed May 7, 2019, 19 pages.
Office Action mailed Sep. 5, 2023, issued in corresponding Brazilian Application No. 1120200226840, filed May 7, 2019, 6 pages.
Office Action mailed Feb. 26, 2024, issued in Korean Application No. 10-2020-7035076, filed Dec. 14, 2020, 10 pages.

* cited by examiner

*Primary Examiner* — Samantha L Shterengarts
*Assistant Examiner* — Karen Cheng
(74) *Attorney, Agent, or Firm* — Christensen O'Connor Johnson Kindness PLLC

(57) ABSTRACT

Automated oligonucleotide synthesis-compatible sulforhodamine dye phosphoramidite compounds and labeled polynucleotides incorporating these dyes are provided.

15 Claims, 4 Drawing Sheets

Specification includes a Sequence Listing.

SEQUENCE LISTING

<160> NUMBER OF SEQ ID NOS: 7

<210> SEQ ID NO 1
<211> LENGTH: 17
<212> TYPE: DNA
<213> ORGANISM: Artificial sequence
<220> FEATURE:
<223> OTHER INFORMATION: Synthetic

<400> SEQUENCE: 1
tcagagtacc tgaaaca                                                  17

<210> SEQ ID NO 2
<211> LENGTH: 23
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 2,6-diaminopurine
<220> FEATURE:
<221> NAME/KEY: misc_feature
<222> LOCATION: (7)..(7)
<223> OTHER INFORMATION: 2,6-diaminopurine
<220> FEATURE:
<221> NAME/KEY: misc_feature
<222> LOCATION: (11)..(11)
<223> OTHER INFORMATION: 2,6-diaminopurine
<220> FEATURE:
<221> NAME/KEY: misc_feature
<222> LOCATION: (15)..(15)
<223> OTHER INFORMATION: 2,6-diaminopurine

<400> SEQUENCE: 2
ccncggngcg ngacntctcg gcc                                           23

<210> SEQ ID NO 3
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 2,6-diaminopurine
<220> FEATURE:
<221> NAME/KEY: misc_feature
<222> LOCATION: (5)..(5)
<223> OTHER INFORMATION: 2,6-diaminopurine
<220> FEATURE:
<221> NAME/KEY: misc_feature
<222> LOCATION: (20)..(20)
<223> OTHER INFORMATION: 2,6-diaminopurine

<400> SEQUENCE: 3
ccngngcaaa ctgggcggcn                                               20

<210> SEQ ID NO 4
<211> LENGTH: 27
<212> TYPE: DNA
<213> ORGANISM: Artificial sequence
<220> FEATURE:
<223> OTHER INFORMATION: Synthetic

<400> SEQUENCE: 4
aaacctccag gccagaaaga gagagta                                       27

```
<210> SEQ ID NO 5
<211> LENGTH: 29
<212> TYPE: DNA
<213> ORGANISM: Artificial sequence
<220> FEATURE:
<223> OTHER INFORMATION: Synthetic

<400> SEQUENCE: 5
aaaaggcatt cctgaagctg acagcattc                                    29

<210> SEQ ID NO 6
<211> LENGTH: 26
<212> TYPE: DNA
<213> ORGANISM: Artificial sequence
<220> FEATURE:
<223> OTHER INFORMATION: Synthetic

<400> SEQUENCE: 6
aaaacctgcc ttctgcgtga gattct                                       26

<210> SEQ ID NO 7
<211> LENGTH: 26
<212> TYPE: DNA
<213> ORGANISM: Artificial sequence
<220> FEATURE:
<223> OTHER INFORMATION: Synthetic

<400> SEQUENCE: 7
ctgtacgaaa agaccacagg gcccat                                       26
```

SULFORHODAMINE PHOSPHORAMIDITE DYES

CROSS REFERENCE TO RELATED APPLICATIONS

This application is a National Stage of International Application No. PCT/US2019/031188 filed May 7, 2019, which claims the benefit of U.S. Patent Application No. 62/668,109, filed May 7, 2018, the disclosure of each of which is expressly incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 72982_Seq_Listing_revised_final_2020-11-16.txt. The text file is 2187 bytes; was created on Nov. 16, 2020; and is being submitted via Patent Center.

BACKGROUND

The invention provides novel sulforhodamine dye phosphoramidite compounds useful as automated oligonucleotide synthesis-compatible red dyes.

Fluorescent dyes are among the most commonly used tags for modifying oligonucleotides because they offer sensitive detection in a wide variety of applications ranging from PCR to sequencing. Rhodamine dyes are widely used in oligonucleotide labeling because they offer longer wavelength emission maxima than other dyes such as fluoresceins and provide opportunities for multicolor labeling and staining. Additionally, rhodamines exhibit higher photostability than fluoresceins and coumarins.

Preparation of fluorescent dye-labeled polynucleotides is typically done by post-synthetic conjugation, for example, by reacting an activated dye intermediate with an amino derivative of a polynucleotide. This approach suffers from certain drawbacks, including low conjugation yields and the need for additional purification of the conjugated product. Incorporation of fluorescent dyes into synthetic polynucleotides via automated phosphoramidite synthesis offers a more convenient approach. However, few phosphoramidite derivatives of fluorescent dyes which allow the fluorescent dye to be added to the polynucleotide as part of the automated solid phase synthesis are commercially available.

One example of a popular oligonucleotide labeling dye is Sulforhodamine 101 sulfonyl chloride (Texas Red® dye). However, Texas Red® dye can only be introduced into an oligonucleotide via post-synthetic coupling as no phosphoramidite derivatives of Texas Red® dye are known. Because Texas Red® dye is unstable, it gives much lower coupling yields than carboxyrhodamine dyes (such as 5-TAMRA, SE) which increases the costs associated with preparation of Texas Red®-labeled oligonucleotides.

To be a viable alternative to Texas Red® dye for automated oligonucleotide synthesis, a fluorophore should have spectral characteristics close to those of Texas Red® dye. Such fluorophore should be stable to standard oligonucleotide synthesis conditions (e.g., iodine treatment, capping, and acid deprotection conditions) and amenable to incorporation at any position in the oligonucleotide. Additionally, for PCR applications, such a fluorophore's brightness should be insensitive to changes in the biologically relevant pH range, and the dye needs to be quenched well to produce high End-Point Fluorescence (EPF), which is measured as a difference between the fluorescence of a quenched probe and a cleaved probe or an unquenched probe (e.g., a hybridized probe).

Previously known alternatives of Texas Red® dye that are compatible with oligo synthesis have certain drawbacks. For instance, CAL Fluor Red® 610 dye is a phosphoramidite that fluoresces in the orange-red region of the visible spectrum and can be used for the 5' labeling of fluorogenic probes, such as probes used in 5' nuclease assays, molecular beacons, and similar detection assays. However, this dye does not contain a protected hydroxyl group and thus can only be added to the 5' terminus of an oligonucleotide, limiting its applications. Another family of dyes, AquaPhluor®, includes a red dye that is highly fluorescent with an absorption maximum at 593 nm and an emission maximum at 613 nm. However, due to its structural limitations, this dye can only be incorporated at the 5' end or the 3' end of an oligonucleotide.

Thus, a need still exists for red fluorescent dyes that are compatible with the conditions of automated phosphoramidite oligonucleotide synthesis, can be incorporated into any position of a polynucleotide, have emission and absorption maxima compatible with the existing PCR instrumentation, and provide a high endpoint fluorescence signal in PCR applications.

SUMMARY

In one aspect, provided herein is a compound having a structure represented by Formula I:

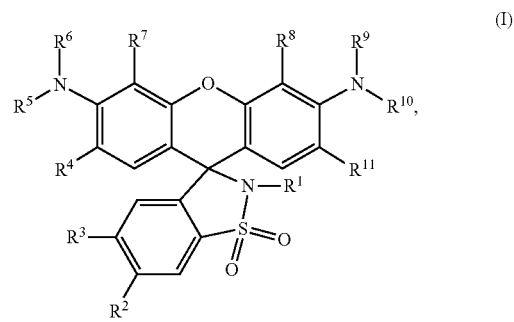

or a stereoisomer, tautomer, or salt thereof, wherein:
$R^1$ is $C_1$-$C_6$ alkyl or $L^1$-X;
$R^2$ is halogen or $SO_2NH_2$,
$R^3$ is H or halogen;
$R^4$, $R^7$, $R^8$, and $R^{11}$ when taken alone are independently H, halogen, or optionally substituted $C_1$-$C_6$ alkyl,
$R^5$, $R^6$, $R^9$, and $R^{10}$ when taken alone are independently H or optionally substituted $C_1$-$C_6$ alkyl;
$R^4$ and $R^5$ when taken together are an optionally substituted $C_2$-$C_3$ alkylene chain connecting the atoms to which $R^4$ and $R^5$ are attached;
$R^6$ and $R^7$ when taken together are an optionally substituted $C_2$-$C_3$ alkylene chain connecting the atoms to which $R^6$ and $R^7$ are attached;
$R^8$ and $R^9$ when taken together are an optionally substituted $C_2$-$C_3$ alkylene chain connecting the atoms to which $R^8$ and $R^9$ are attached;

$R^{10}$ and $R^{11}$ when taken together are an optionally substituted $C_2$-$C_3$ alkylene chain connecting the atoms to which $R^{10}$ and $R^{11}$ are attached;

$R^5$ and $R^6$, when taken together with the nitrogen atom to which $R^5$ and $R^6$ are attached, form a 5-membered or a 6-membered unsaturated ring;

$R^9$ and $R^{10}$, when taken together with the nitrogen atom to which $R^9$ and $R^{10}$ are attached, form a 5-membered or a 6-membered unsaturated ring;

$L^1$ is an optionally substituted $C_2$-$C_{10}$ alkylene or optionally substituted $C_2$-$C_{20}$ heteroalkylene;

X is an activated ester, $N_3$, propynyl, maleimido, or —O—P(OCH$_2$CH$_2$CN)NR$^{12}$R$^{13}$ or X is:

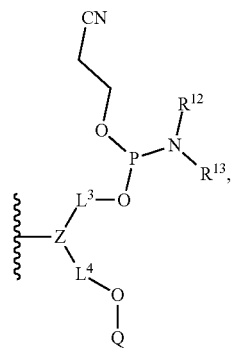

wherein $L^3$ and $L^4$ are independently an optionally substituted $C_2$-$C_{10}$ alkylene or optionally substituted $C_2$-$C_{30}$ heteroalkylene;

Q is a hydroxyl protecting group;

Z is CH, N, NHC(O)N, or OC(O)N; and $R^{12}$ and $R^{13}$ are independently optionally substituted $C_1$-$C_6$ alkyl.

In some embodiments, $R^2$ is Cl and $R^3$ is H. In some embodiments, X is —OP(OCH$_2$CH$_2$CN)N(i-Pr)$_2$. In some embodiments, $L^1$ is a PEG$_{2-10}$ linker. In certain embodiments, $L^1$ is —CH$_2$CH$_2$OCH$_2$CH$_2$—.

In some embodiments, $R^4$ and $R^5$ taken together are an optionally substituted $C_3$ alkylene chain connecting the atoms to which $R^4$ and $R^5$ are attached; $R^{10}$ and $R^{11}$ taken together are an optionally substituted $C_3$ alkylene chain connecting the atoms to which $R^{10}$ and $R^{11}$ are attached; $R^6$ and $R^7$ taken together are an optionally substituted $C_3$ alkylene chain connecting the atoms to which $R^6$ and $R^7$ are attached; and $R^8$ and $R^9$ taken together are an optionally substituted $C_3$ alkylene chain connecting the atoms to which $R^8$ and $R^9$ are attached. In some embodiments, $R^4$ and $R^5$ taken together are a propylene chain connecting the atoms to which $R^4$ and $R^5$ are attached; $R^{10}$ and $R^{11}$ taken together are a propylene chain connecting the atoms to which $R^{10}$ and $R^{11}$ are attached; $R^6$ and $R^7$ taken together are a propylene chain connecting the atoms to which $R^6$ and $R^7$ are attached; and $R^8$ and $R^9$ taken together are a propylene chain connecting the atoms to which $R^8$ and $R^9$ are attached. In some embodiments, $R^5$, $R^6$, $R^9$, and $R^{10}$ are each methyl.

In some embodiments, Q is an acid-labile hydroxyl protecting group. In some embodiments, Q is a trityl or dimethoxytrityl group.

In some embodiments, $C_2$-$C_6$ alkylene or —(OCH$_2$CH$_2$)$_m$—, wherein m is an integer ranging from 2 to 6. In some embodiments, $L^3$ and $L^4$ are —CH$_2$CH$_2$—. In some embodiments, X is:

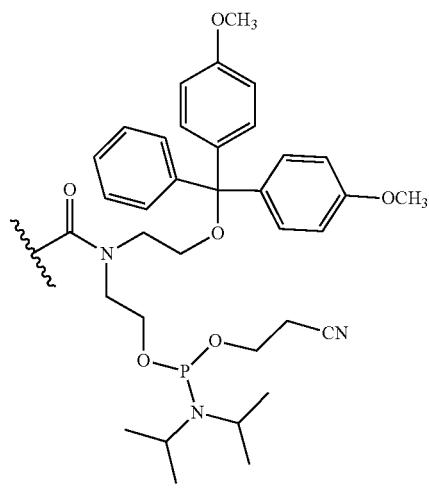

or

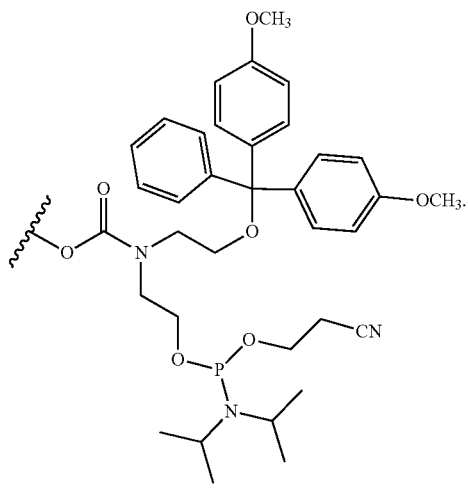

In some embodiments, the compound has a structure represented by Formula IA:

(IA)

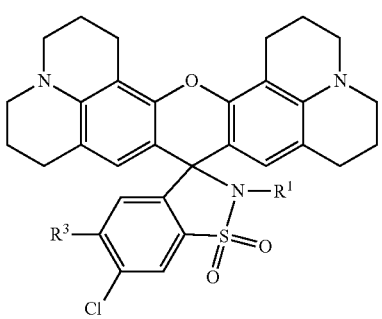

or a stereoisomer, tautomer, or salt thereof, wherein $R^1$ is $L^1X$ and $R^3$ is H or halogen. In some embodiments, X is —OP(OCH$_2$CH$_2$CN)N(i-Pr)$_2$.

In some embodiments, the compound is:

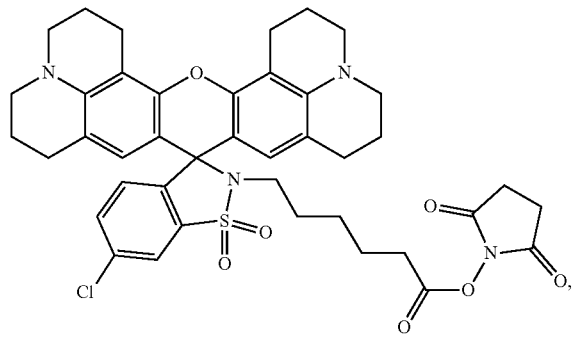 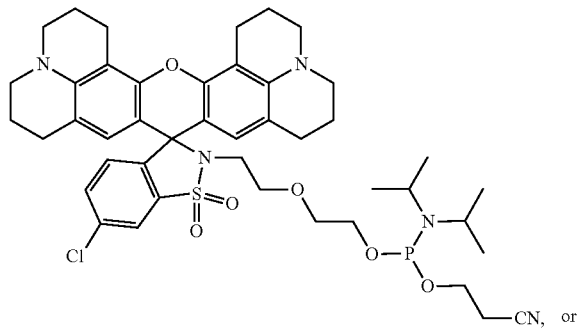

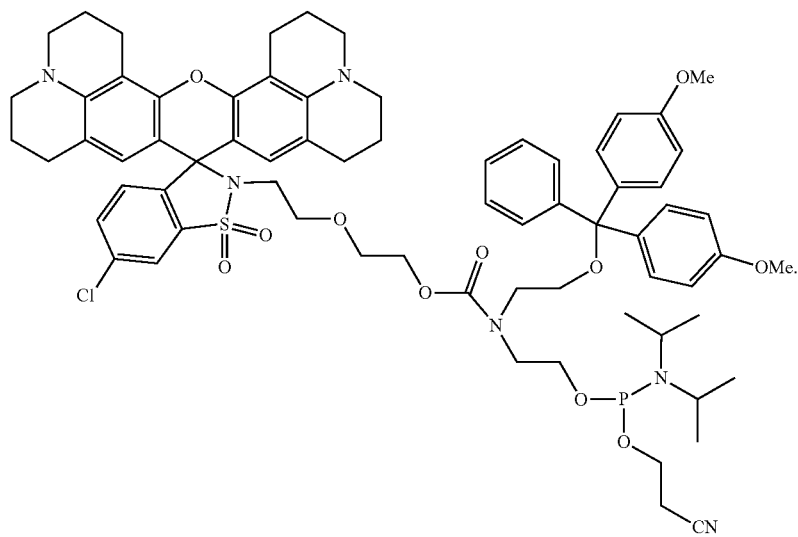

In a second aspect, provided herein is a compound represented by Formula II:

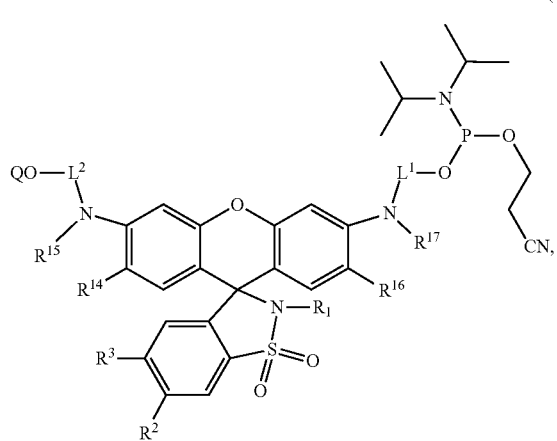

(II)

or a stereoisomer, tautomer, or salt thereof, wherein:
$R^1$ is $C_1$-$C_6$ alkyl;
$R^2$ is H, halogen, or $SO_2NH_2$,
$R^3$ is H or halogen;
$R^{14}$ and $R^{16}$ when taken alone are independently H, halogen, or optionally substituted $C_1$-$C_6$ alkyl;
$R^{15}$ and $R^{17}$ when taken alone are independently H or optionally substituted $C_1$-$C_6$ alkyl;
$R^{14}$ and $R^{15}$ when taken together form an optionally substituted $C_2$-$C_3$ alkylene chain connecting the atoms to which $R^{14}$ and $R^{15}$ attached;
$R^{16}$ and $R^{17}$ when taken together form an optionally substituted $C_2$-$C_3$ alkylene chain connecting the atoms to which $R^{16}$ and $R^{17}$ are attached;
Q is a hydroxyl protecting group; and
$L^1$ and $L^2$ are independently an optionally substituted $C_2$-$C_{10}$ alkylene or optionally substituted $C_2$-$C_{20}$ heteroalkylene.

In some embodiments, $R^3$ is H. In some embodiments, $R^2$ is H. In some embodiments, $R^2$ is Cl.

In some embodiments, the compound is represented by Formula (IIA):

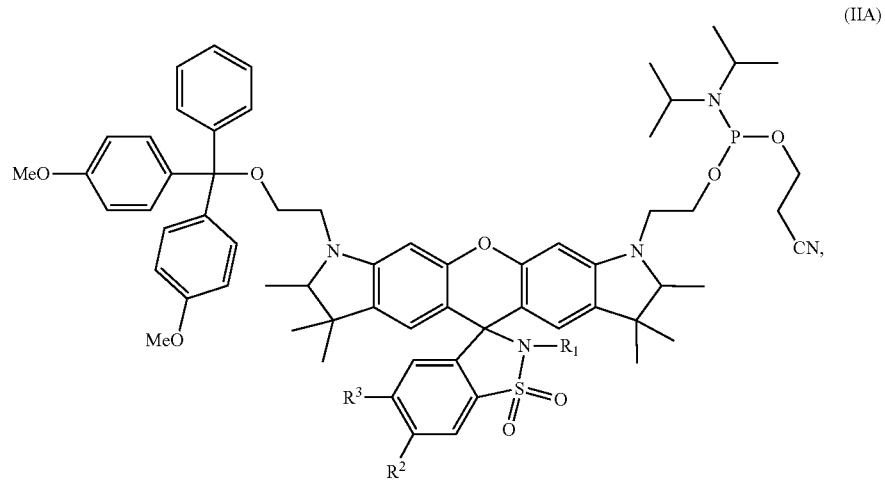
or a stereoisomer, tautomer, or salt thereof, wherein:
$R^1$ is $C_1$-$C_6$ alkyl;
$R^2$ is H, halogen, or $SO_2NH_2$; and
$R^3$ is H or halogen.
In some embodiments, the compound is:
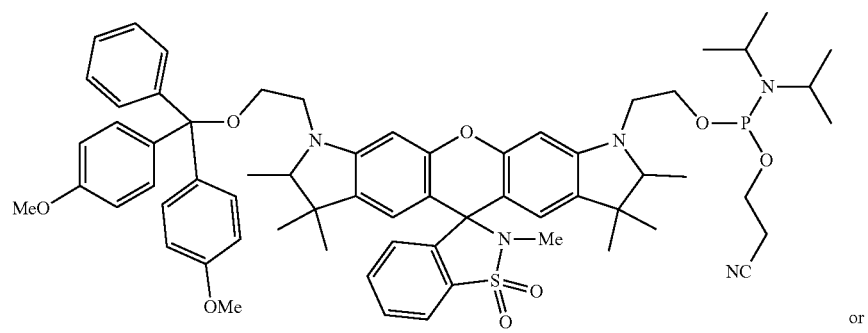
or
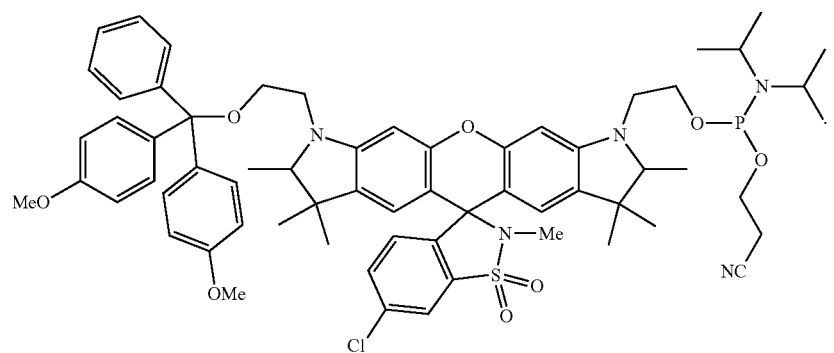
In a third aspect, provided herein is a compound having a structure of Formula (III):

(III)

[Structure of Formula (III): a xanthene-based dye with substituents R⁵,R⁶-N on left ring, R⁷, R⁸, R⁴ on aromatic positions, O bridging the xanthene, R⁹,R¹⁰-N on right ring, R¹ substituent, and a spiro-linked benzosulfonamide ring bearing R², R³ substituents with N-(CH₂)ₙ-Y side chain]

or a stereoisomer, tautomer, or salt thereof, wherein:

$R^2$ is H, halogen or $SO_2NH_2$;

$R^3$ is halogen or H;

$R^4$, $R^7$, $R^8$, and $R^{11}$ when taken alone are independently H, halogen, or optionally substituted $C_1$-$C_6$ alkyl, $R^5$, $R^6$, $R^9$ and $R^{10}$ when taken alone are independently H or optionally substituted $C_1$-$C_6$ alkyl;

$R^4$ and $R^5$ when taken together are an optionally substituted $C_2$-$C_3$ alkylene chain connecting the atoms to which $R^4$ and $R^5$ are attached;

$R^6$ and $R^7$ when taken together are an optionally substituted $C_2$-$C_3$ alkylene chain connecting the atoms to which $R^6$ and $R^7$ are attached;

$R^8$ and $R^9$ when taken together are an optionally substituted $C_2$-$C_3$ alkylene chain connecting the atoms to which $R^8$ and $R^9$ are attached;

$R^{10}$ and $R^{11}$ when taken together are an optionally substituted $C_2$-$C_3$ alkylene chain connecting the atoms to which $R^{10}$ and $R^{11}$ are attached;

$R^5$ and $R^6$, when taken together with the nitrogen atom to which $R^5$ and $R^6$ are attached, form a 5-membered or a 6-membered unsaturated ring;

$R^9$ and $R^{10}$, when taken together with the nitrogen atom to which $R^9$ and $R^{10}$ are attached, form a 5-membered or a 6-membered unsaturated ring;

n is an integer from 1 to 9;

Y is:

[Structure: cytidine analog with NH₂-substituted pyrimidine, 5-position alkyne linked to propanamide attached via NH to wavy bond; deoxyribose sugar with QO- at 5' and 3'-O-phosphoramidite bearing OCH₂CH₂CN and N(R¹²)(R¹³)]

or

[Structure: thymidine-like analog with 5-alkynyl propanamide linker attached via NH to wavy bond; deoxyribose with QO- at 5' and 3'-O-phosphoramidite bearing OCH₂CH₂CN and N(R¹²)(R¹³)]

wherein:

Q is a hydroxyl protecting group; and $R^{12}$ and $R^{13}$ are independently optionally substituted $C_1$-$C_6$ alkyl.

In some embodiments, $R^2$ is Cl and $R^3$ is H.

In some embodiments, $R^4$ and $R^5$ taken together are an optionally substituted $C_3$ alkylene chain connecting the atoms to which $R^4$ and $R^5$ are attached; $R^{10}$ and $R^{11}$ taken together are an optionally substituted $C_3$ alkylene chain connecting the atoms to which $R^{10}$ and $R^{11}$ are attached; $R^6$ and $R^7$ taken together are an optionally substituted $C_3$ alkylene chain connecting the atoms to which $R^6$ and $R^7$ are attached; and $R^8$ and $R^9$ taken together are an optionally substituted $C_3$ alkylene chain connecting the atoms to which $R^8$ and $R^9$ are attached. In some embodiments, $R^4$ and $R^5$ taken together are a propylene chain connecting the atoms to which $R^4$ and $R^5$ are attached; $R^{10}$ and $R^{11}$ taken together are a propylene chain connecting the atoms to which $R^{10}$ and $R^{11}$ are attached; $R^6$ and $R^7$ taken together are a propylene chain connecting the atoms to which $R^6$ and $R^7$ are attached; and $R^8$ and $R^9$ taken together are a propylene chain connecting the atoms to which $R^8$ and $R^9$ are attached.

In some embodiments, Q is an acid-labile hydroxyl protecting group. In some embodiments, Q is a trityl or dimethoxytrityl group. In yet other embodiments, $R^{12}$ and $R^{13}$ are each isopropyl.

In some embodiments, the compound is:

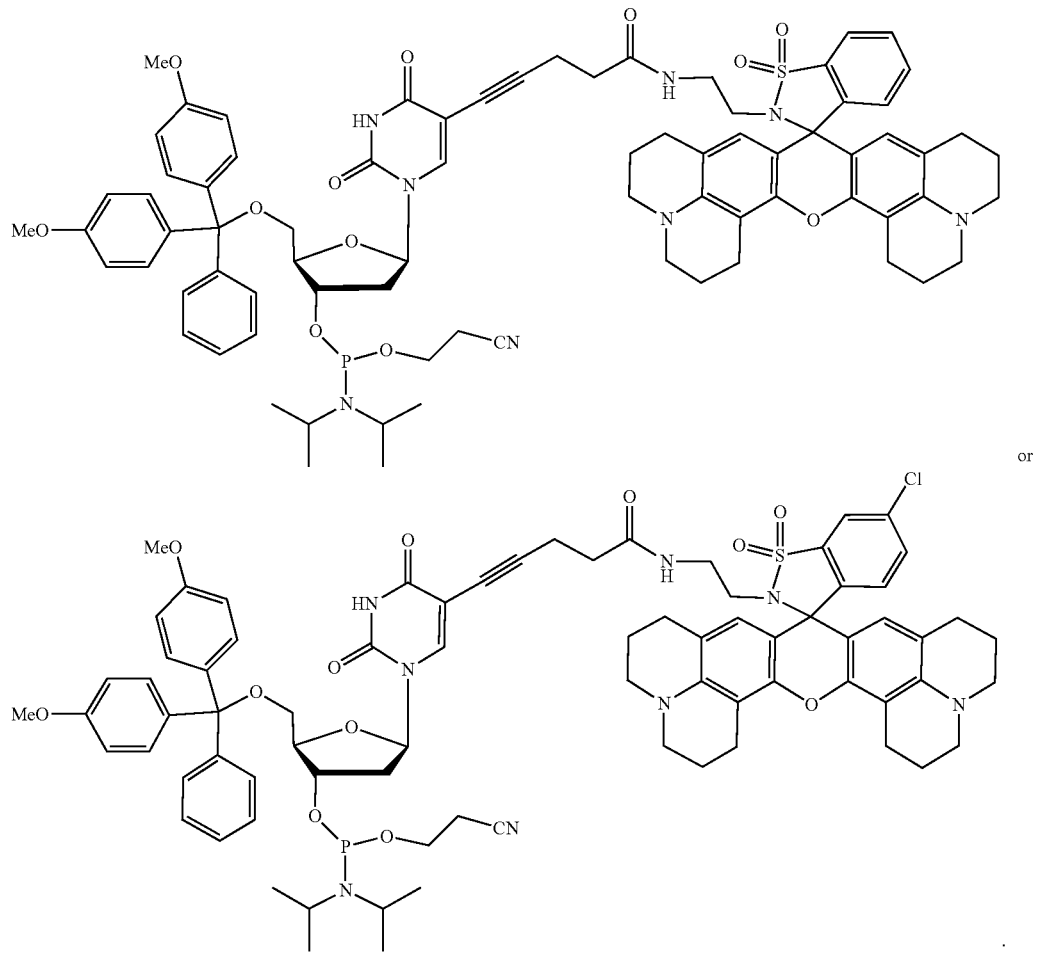

or

In a fourth aspect, provided herein is a compound represented by Formula VI:

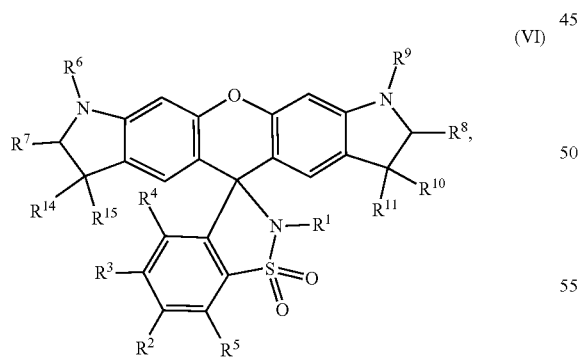
(VI)

or a stereoisomer, tautomer, or salt thereof, wherein:
$R^1$ is $L^1$-X;
$R^2$, $R^3$, $R^4$, and $R^5$ are independently H, halogen, $C_1$-$C_6$ alkyl, or $SO_2NH_2$;
$R^6$ and $R^9$ are independently H or optionally substituted $C_1$-$C_6$ alkyl;
$R^7$, $R^8$, $R^{10}$, $R^{11}$, $R^{14}$, and $R^{15}$ are independently H or optionally substituted $C_1$-$C_6$ alkyl;

$L^1$ is an optionally substituted $C_2$-$C_{10}$ alkylene or optionally substituted $C_2$-$C_{20}$ heteroalkylene;
X is an activated ester, $N_3$, propynyl, maleimido, or —O—P(OCH$_2$CH$_2$CN)NR$^{12}$R$^{13}$, or X is:

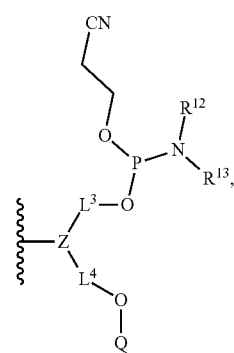

wherein
$L^3$ and $L^4$ are independently an optionally substituted $C_2$-$C_{10}$ alkylene or optionally substituted $C_2$-$C_{30}$ heteroalkylene;
Q is a hydroxyl protecting group;
Z is CH, N, NHC(O)N, or OC(O)N; and $R^{12}$ and $R^{13}$ are independently optionally substituted $C_1$-$C_6$ alkyl.

In some embodiments of Formula VI, $R^7$, $R^8$, $R^{10}$, $R^{11}$, $R^{14}$, and $R^{15}$ are methyl. In certain embodiments, X is —OP(OCH$_2$CH$_2$CN)N(i-Pr)$_2$. In some embodiments, $L^1$ is a PEG$_{2-10}$ linker, and in other embodiments, $L^1$ is —CH$_2$CH$_2$OCH$_2$CH$_2$—. In certain embodiments, $R^2$, $R^3$, $R^4$, and $R^5$ are H.

In some embodiments, $R^6$ is a $C_1$-$C_6$ alkyl optionally substituted with OH or C1-C6 acyloxy, for example, $R^6$ is an ethyl substituted with OH or OAc. In some embodiments, $R^9$ is a $C_1$-$C_6$ alkyl optionally substituted with OH or $C_1$-$C_6$ acyloxy, for example, $R^9$ is an ethyl substituted with OH or OAc.

In some embodiments of Formula VI, the compound is:

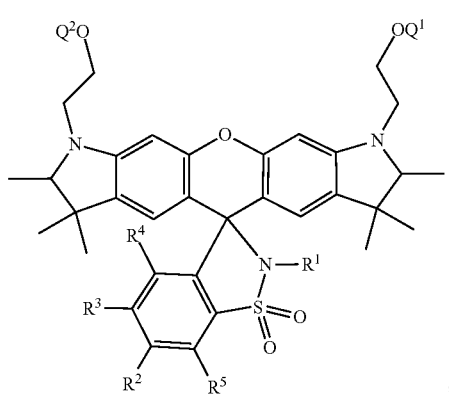

or a stereoisomer, tautomer, or salt thereof, wherein:

$R^1$, $R^2$, $R^3$, $R^4$, and $R^5$ are as described for above for Formula VI; and $Q^1$ and $Q^2$ are independently H or C1-C6 acyl.

In some embodiments, $R^2$, $R^3$, $R^4$, and $R^5$ are H. In some embodiments, $Q^1$ and $Q^2$ are acetyl.

In some embodiments of Formula VI, the compound is:

wherein $R^1$ is as defined above for Formula VI.

In some embodiments of Formula VI, the compound is:

In a fifth aspect, provided herein is a labeled polynucleotide comprising a compound of formula IV:

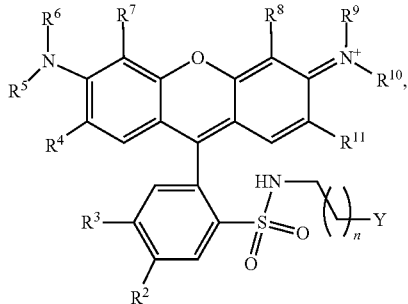

(IV)

or a stereoisomer, tautomer, or salt thereof, wherein:

$R^2$ is halogen or $SO_2NH_2$;

$R^3$ is H or halogen;

$R^4$, $R^7$, $R^8$, and $R^{11}$ when taken alone are independently H, halogen, or optionally substituted $C_1$-$C_6$ alkyl, $R^5$, $R^6$, $R^9$, and $R^{10}$ when taken alone are independently H or optionally substituted $C_1$-$C_6$ alkyl;

$R^4$ and $R^5$ when taken together are an optionally substituted $C_2$-$C_3$ alkylene chain connecting the atoms to which $R^4$ and $R^5$ are attached;

$R^6$ and $R^7$ when taken together are an optionally substituted $C_2$-$C_3$ alkylene chain connecting the atoms to which $R^6$ and $R^7$ are attached;

$R^8$ and $R^9$ when taken together are an optionally substituted $C_2$-$C_3$ alkylene chain connecting the atoms to which $R^8$ and $R^9$ are attached;

$R^{10}$ and $R^{11}$ when taken together are an optionally substituted $C_2$-$C_3$ alkylene chain connecting the atoms to which $R^{10}$ and $R^{11}$ are attached;

$R^5$ and $R^6$, when taken together with the nitrogen atom to which $R^5$ and $R^6$ are attached, form a 5-membered or a 6-membered unsaturated ring;

$R^9$ and $R^{10}$, when taken together with the nitrogen atom to which $R^9$ and $R^{10}$ are attached, form a 5-membered or a 6-membered unsaturated ring;

n is an integer from 1 to 9;

Y is:

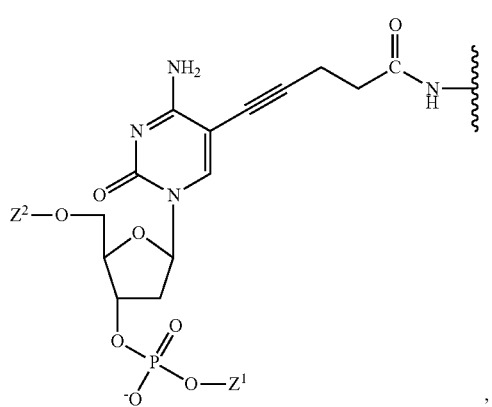

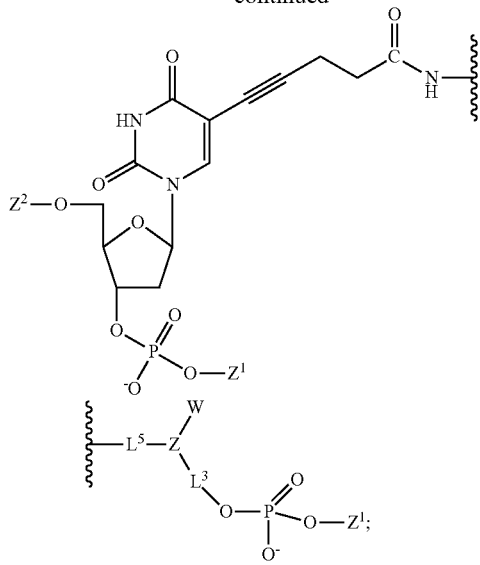

, or wherein:

the wavy line is the point of attachment to Formula III;

$R^{12}$ and $R^{13}$ are independently optionally substituted $C_1$-$C_6$ alkyl;

W is H or $L^4$-O-$Z^2$;

$L^3$, $L^4$, and $L^5$ are independently an optionally substituted $C_2$-$C_{10}$ alkylene or optionally substituted $C_2$-$C_{30}$ heteroalkylene;

Z is CH, N, NHC(O)N, or OC(O)N;

$Z^1$ is a nucleotide or oligonucleotide; and $Z^2$ is a nucleotide, oligonucleotide, or H.

In some embodiments, $R^2$ is Cl and $R^3$ is H. In other embodiments, $R^4$ and $R^5$ are an optionally substituted $C_3$ alkylene chain connecting the atoms to which $R^4$ and $R^5$ are attached; $R^{10}$ and $R^{11}$ are an optionally substituted $C_3$ alkylene chain connecting the atoms to which $R^{10}$ and $R^{11}$ are attached; $R^6$ and $R^7$ are an optionally substituted $C_3$ alkylene chain connecting the atoms to which $R^6$ and $R^7$ are attached; and $R^8$ and $R^9$ are an optionally substituted $C_3$ alkylene chain connecting the atoms to which $R^8$ and $R^9$ are attached.

In some embodiments, the labeled polynucleotide is a 5'-nuclease PCR probe. In some embodiments, the labeled polynucleotide further comprises a fluorescence quencher.

In some embodiments, the labeled polynucleotide is attached to a solid support. In some embodiments, the solid support is a controlled pore glass bead, polystyrene bead, magnetic bead, or microwell plate.

In a fifth aspect, provided herein is a method for preparing a labeled conjugate of a ligand comprising contacting a ligand with a compound disclosed herein in a suitable solvent under conditions sufficient to covalently attach the compound to the ligand thereby forming the labeled conjugate.

In some embodiments, the ligand is a polynucleotide, a protein, a peptide, a polysaccharide, a polymer with an ethylenic backbone, or a solid support. In some embodiments, the ligand is a polynucleotide. In other embodiments, the conditions sufficient to covalently attach the compound to the ligand are automated phosphoramidite oligonucleotide synthesis conditions.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
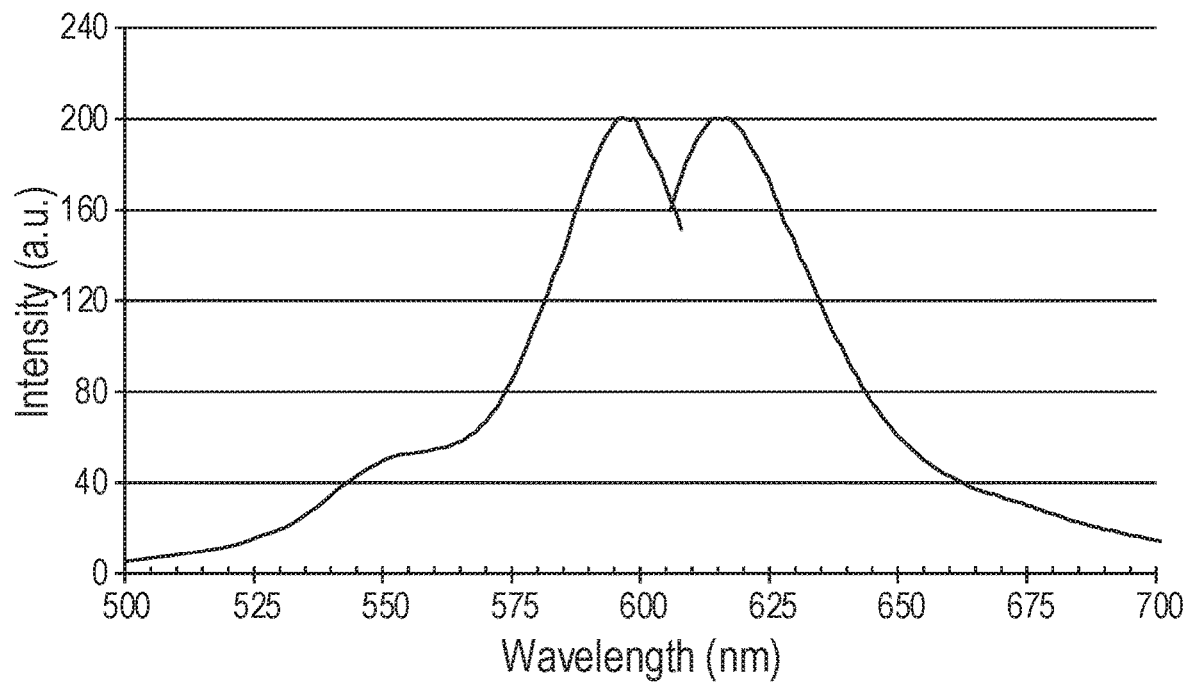
FIG. 1A is the excitation and emission spectra an exemplary polynucleotide SEQ ID NO: 1 labeled with Texas Red® dye: (Tx Red)-TCAGAGTACCTGAAACA; (Oligo A) Ex/Em max=598 nm/616 nm. In this figure, the x-axis is nm, and the y-axis is fluorescence units.

Provided herein are sulforhodamine dye phosphoramidites that can be incorporated into oligonucleotides via standard automated oligonucleotide synthesis. Additionally, sulforhodamine dyes comprising other reactive groups are provided.

Throughout the present specification and the accompanying claims, the words "comprise" and "include" and variations thereof such as "comprises," "comprising," "includes," and "including" are intended to convey the possible inclusion of other elements or integers not specifically recited, where the context allows. As used herein, the term "consisting of" is intended to mean including and limited to whatever follows the phrase "consisting of." Thus, the phrase "consisting of" indicates that the listed elements are required or mandatory and that no other elements may be present. The term "consisting essentially of" means that the composition, method or structure may include additional ingredients, steps and/or parts, but only if the additional ingredients, steps and/or parts do not materially alter the basic and novel characteristics of the claimed composition, method or structure.

The terms "a" and "an" and "the" and similar terms are to be construed to cover both the singular and the plural, unless otherwise indicated herein or clearly contradicted by context.

All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise indicated, nucleic acids or oligonucleotides are written left to right in 5' to 3' orientation.

As used herein, the term "amplification" refers to any means by which at least a partial sequence of at least one target nucleic acid or its sequence complement is produced, typically in a template-dependent manner, including without limitation, a broad range of techniques for amplifying nucleic acid sequences, either linearly or exponentially. Non-limiting exemplary amplification methods include polymerase chain reaction (PCR), reverse-transcriptase PCR, real-time PCR, nested PCR, multiplex PCR, quantitative PCR (Q-PCR), nucleic acid sequence based amplification (NASBA), transcription mediated amplification (TMA), ligase chain reaction (LCR), rolling circle amplification (RCA), strand displacement amplification (SDA), ligase detection reaction (LDR), multiplex ligation-dependent probe amplification (MLPA), ligation followed by Q-replicase amplification, primer extension, strand displacement amplification (SDA), hyperbranched strand displacement amplification, multiple displacement amplification (MDA), nucleic acid strand-based amplification (NASBA), two-step multiplexed amplifications, digital amplification, and the like. Descriptions of such techniques can be found in, among other sources, Ausubel et al.; PCR Primer: A Laboratory Manual, Diffenbach, Ed., Cold Spring Harbor Press (1995); The Electronic Protocol Book, Chang Bioscience (2002); The Nucleic Acid Protocols Handbook, R. Rapley, ed., Humana Press, Totowa, N.J. (2002); and Innis et al, PCR Protocols: A Guide to Methods and Applications, Academic Press (1990).

As used herein, the term "base" means a nitrogen-containing heterocyclic moiety capable of forming hydrogen bonds, e.g., Watson-Crick type hydrogen bonds, with a complementary nucleotide base or nucleotide base analog, e.g. a purine, a 7-deazapurine, or a pyrimidine. Typical bases are the naturally occurring bases adenine, cytosine, guanine, thymine, and uracil. Bases also include analogs of naturally occurring bases such as deazaadenine, 7-deaza-8-azaadenine, 7-deazaguanine, 7-deaza-8-azaguanine, inosine, nebularine, nitropyrrole, nitroindole, 2-amino-purine, 2,6-diamino-purine, hypoxanthine, 5-methylcytosine, isocytosine, pseudoisocytosine, 5-bromouracil, 5-propynyluracil, 6-aminopurine, 2-chloro-6-aminopurine, xanthine, hypoxanthine, etc.

As used herein, the term "complementary" refers to the ability of polynucleotide sequences to hybridize to and from base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. The percentage of "complementarity" of a probe sequence to a target sequence is the percentage "identity" of the probe sequence to the sequence of the target or to the complement of the sequence of the target. In determining the degree of "complementarity" between a probe and a target sequence, the degree of "complementarity" is expressed as the percentage identity between the sequence of the probe and the sequence of the target sequence or the complement of the sequence of the target sequence that best aligns therewith. An exemplary probe is a polynucleotide as described herein.

As used herein, the term "duplex" refers to a double-stranded hybridization complex formed by annealing (hybridizing) complementary (or partially complementary) single-stranded polynucleotides, e.g., DNA, RNA, LNA, or peptide nucleic acid (PNA).

As used herein, "fluorescence quenching" refers to any process that decreases the fluorescence intensity of a fluorescent sample, i.e., a fluorescent polynucleotide probe. A variety of molecular interactions can result in quenching. Non-limiting examples include excited-state reactions, molecular rearrangements, energy transfer, ground-state complex formation, and collisional quenching.

As used herein, "halogen" means F, Cl, Br, or I.

The terms "hybridize" and "hybridization" are used herein with reference to "specific hybridization" which is the binding, duplexing, or annealing of a nucleic acid molecule preferentially to a particular nucleotide sequence, in some embodiments, under stringent conditions. The term "stringent conditions" refers to conditions under which a probe will hybridize preferentially to its target sequence, and to a lesser extent to, or not at all to, other sequences. "Stringent hybridization" and "stringent hybridization wash conditions" in the context of nucleic acid hybridization are sequence-dependent and are different under different environmental parameters. An extensive guide to the hybridization of nucleic acids is found in, e.g., Tijssen (1993) Laboratory Techniques in Biochemistry and Molecular Biology-Hybridization with Nucleic Acid Probes part I, Ch. 2, "Overview of principles of hybridization and the strategy of nucleic acid probe assays," Elsevier, NY. The degree of hybridization of a polynucleotide to a target sequence, also known as hybridization strength, is determined by methods that are well-known in the art. A preferred method is to determine the T m of a given hybrid duplex. This can be accomplished by subjecting a formed duplex in solution to gradually increasing temperature and monitoring the denaturation of the duplex, for example, by absorbance of ultraviolet light, which increases with the unstacking of base pairs that accompanies denaturation. T m is generally defined as the temperature at which half of the DNA strands are in the single-stranded (ssDNA) state. $T_m$ depends on various parameters such as the length of the hybridized complementary strand sequence, their specific nucleotide sequences, base compositions, base modifications, and the concentrations of the complementary strands.

As used herein, the terms "label" and "detectable label" are used interchangeably and refer to a moiety that, when attached to a biomolecule, a nucleoside, a nucleotide, or a polynucleotide, renders such biomolecule, nucleoside, nucleotide, or polynucleotide detectable by suitable detection means. Exemplary labels include fluorophores, chromophores, radioisotopes, spin-labels, enzyme labels, chemiluminescent labels, electrochemiluminescent compounds, magnetic labels, microspheres, colloidal metal, immunologic labels, ligands, enzymes, and the like.

As used herein, the terms "modified nucleotide base" or "modified base" refer to a base that does not have the structure of a naturally occurring base and thus, is non-naturally occurring. As used herein, the terms "modified sugar" refers to a sugar or sugar analog that does not have the structure of a naturally occurring sugar, e.g. ribose or deoxyribose sugar, and thus is non-naturally occurring.

As used herein, the term "naturally-occurring" in the context of nucleic acid molecules refers to an RNA or DNA molecule (single-stranded or double-stranded) having a nucleotide sequence that occurs in nature and comprising only components, such as bases, sugars, nucleosides, and nucleotides that occur in nature.

As used herein, the term "nucleoside" refers to a molecule consisting of a nitrogenous base of the type mentioned herein that is bound to a sugar of the types mentioned herein, for example, to ribose or deoxyribose sugar via a beta-glycosidic linkage. Examples of nucleosides include adenosine, cytidine, guanosine, thymidine, uridine, and inosine.

As used herein, the term "nucleotide" means a phosphate ester of a nucleoside, either as an independent monomer or as a subunit within a polynucleotide. Nucleotide monomers include for example nucleotide 5'-monophosphate, 5'-diphosphate, 5'-triphosphate, and 3'-monophosphate. Nucleotide triphosphates are sometimes denoted as "NTP", "dNTP" (2'-deoxypentose) or "ddNTP" (2',3'-dideoxypentose) to particularly point out the structural features of the ribose sugar. "Nucleotide 5'-triphosphate" refers to a nucleotide with a triphosphate ester group at the 5' position. The triphosphate ester group may include sulfur substitutions for one or more phosphate oxygen atoms, e.g. alpha-thionucleotide 5'-triphosphates. A nucleotide monophosphate, diphosphate or triphosphate may serve as the substrate for a nucleic acid processing enzyme that catalyzes modifications of nucleic acids or nucleic acid intermediates.

As used herein, the term "oligonucleotide" broadly refers to a single stranded chain composed primarily or entirely of about 2 to about 300 naturally occurring or modified nucleotide monomer units, e.g., of deoxyribose or ribose sugar rings substituted with A, C, G, T, or U bases and which are linked by conventional phosphate backbone moieties. More particularly, the term refers to a single stranded chain of deoxyribonucleotides, in the size range described above. In some embodiments, an oligonucleotide can comprise one or more modified bases and/or sugars. In addition to nucleotide monomer units, an oligonucleotide can incorporate one or more detectable labels and/or one or more reactive groups.

As used herein, the term "plurality" means more than one.

As used herein, the term "polynucleotide" generally refers to an oligonucleotide that comprises about 10 to about 300 nucleotide monomer units. In addition to nucleotide monomer units, a polynucleotide can incorporate one or more detectable labels and/or one or more reactive groups.

As used herein, the term "primer" refers to a polynucleotide or modified polynucleotide that is effective as a starting point to synthesize a polynucleotide strand that is complementary to a target nucleic acid strand. For example, primers for use in PCR comprise a forward and reverse primer wherein the forward primer contains a sequence complementary to a region of a target nucleic acid strand and guides synthesis of a complementary strand. A reverse primer contains a sequence complementary to the opposite stand and guides synthesis along the opposite strand of the target nucleic acid strand.

As used herein, the term "probe" refers to a labeled oligonucleotide or labeled modified oligonucleotide containing a sequence complementary to a region of a target nucleic acid sequence, allowing the probe to form a duplex with the target sequence and generate a detectable signal indicating the presence of the region of the target sequence. A detectable signal is generated during or after hybridization, either directly or indirectly. In some applications, such as during primer extension in 5'-nuclease PCR, the probes lack an extendable 3' hydroxyl group to prevent polymerase-mediated extension of the probe. In certain embodiments, probes include TaqMan® probes, TaqMan MGB® probes, Pleiades® probes, molecular beacons (e.g., those disclosed in Tyagi, Sanjay & Kramer, Fred. (2012) Molecular Beacons in Diagnostics. F1000 medicine reports. 4. 10. 10.3410/M4-10), and the like.

As used herein, the terms "protecting group," "protective group", or "protected form" refer to a labile chemical modification of a functional group (e.g., hydroxyl) meant to preserve its functionality and/or to obtain chemoselectivity in a subsequent chemical reaction. A protecting group is removed from the final product by a deprotective treatment (e.g., treatment with acid).

As used herein, the term "solid support" refers to any insoluble material including particles (e.g., beads), fibers, monoliths, membranes, filters, plastic strips, arrays, microwell plates, and the like. In some embodiments, solid supports are solid supports suitable for automated phosphoramidite oligonucleotide synthesis, such as polystyrene and controlled pore glass (CPG).

Sulforhodamine Dyes and Phosphoramidites Thereof

In one aspect, provided herein are sulforhodamine dyes comprising one or more reactive groups, e.g., a phosphoramidite group.

In certain embodiments, the dyes disclosed herein comprise a sultam moiety. In some embodiments, the dyes disclosed herein can exist in open or closed form, as shown below for one exemplary compound:

referring to the dyes disclosed herein, the term "sulforhodamine dye" includes both open fluorescent forms and their corresponding closed forms even though only the open forms are fluorescent.

Such phenomenon of the colored-to-colorless transition that is associated with the reversible open-to-closed, pH-dependent interconversion of sultams derived from sulforhodamine dyes is known in the art (See e.g., Corrie J. E. T. and Munasinghe V. R. *Dyes and Pigments* 79 (2008): 76-82.) Certain reactive derivatives of sulforhodamine dyes used for labeling biological molecules, such as sulforhodamine B chloride, are generally available from commercial suppliers as a mixture of two sulfonyl chloride isomers, ortho and para isomers, but only the isomer with its sulfonyl chloride ortho to the xanthylium system can form a cyclic sulfonamide (sultam) compound that undergoes the ring-chain process shown above. Thus, it has been reported that the ortho isomers of such dyes are generally not desirable for biological applications because fluorescence of the ortho-isomers is pH-dependent (See e.g., Corrie J. E. T. et al. *Bioconjugate Chem.* 12 (2001): 186-194.). Surprisingly, the inventors discovered that polynucleotide conjugates of the dyes of the present disclosure, unlike the conjugate of the dyes disclosed in the art, have fluorescence that is not pH-dependent in the pH range relevant for PCR applications, e.g., from about 6.5 to about 8.5, and can be quenched well with conventional quenchers, such as BHQ-2 quencher (Biosearch), to produce high end-point fluorescence (EPF). As used herein, end-point fluorescence is a difference between the fluorescence of a quenched probe and a cleaved probe or a difference between the fluorescence of a quenched probe and a hybridized probe.

In certain embodiments, the "open" form of the sulforhodamine dyes disclosed herein surprisingly has spectral properties, such as emission and absorption maxima, comparable to or matching those of Sulforhodamine 101 dye or a TAMRA dye. However, unlike Sulforhodamine 101-type dyes that comprise polar sulfonic acid groups and thus cannot be prepared in the form of phosphoramidite reagents, the sulforhodamine dyes disclosed herein are non-polar in their closed (sultam) form and easily dissolve in organic solvents compatible with automated phosphoramidite synthesis and/or bioconjugation conditions. This advantageous

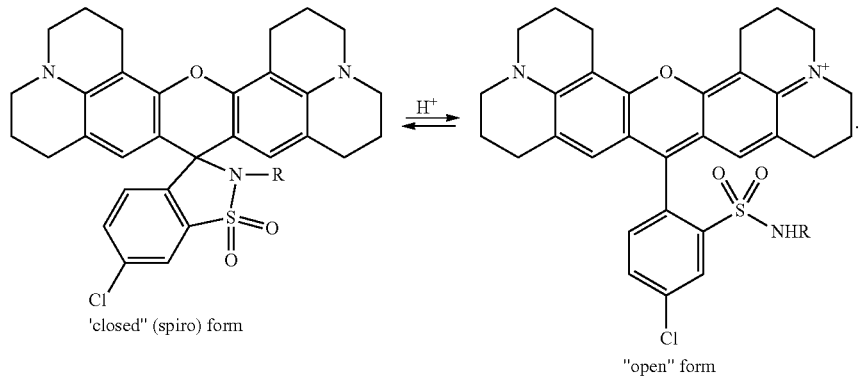

"closed" (spiro) form

"open" form

In their cyclic or "closed" form, the sulforhodamine dyes of the disclosure and phosphoramidites thereof are colorless and non-fluorescent. However, upon protonation, e.g., exposure to acidic conditions, the cyclic form can convert to the "open" form which is fluorescent. As used herein, when property of the dyes disclosed herein also allows ease of purification by conventional laboratory techniques such as silica gel column chromatography.

In some embodiments, the dyes have a structure represented by Formula I:

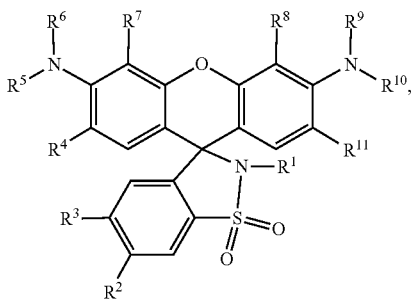

(I)

or a stereoisomer, tautomer, or salt thereof, wherein:

$R^1$ is $C_1$-$C_6$ alkyl or $L^1$-X;

$R^2$ is halogen or $SO_2NH_2$, $R^3$ is H or halogen;

$R^4$, $R^7$, $R^8$, and $R^{11}$ when taken alone are independently H, halogen, or optionally substituted $C_1$-$C_6$ alkyl, $R^5$, $R^6$, $R^9$, and $R^{10}$ when taken alone are independently H or optionally substituted $C_1$-$C_6$ alkyl;

$R^4$ and $R^5$ when taken together are an optionally substituted $C_2$-$C_3$ alkylene chain connecting the atoms to which $R^4$ and $R^5$ are attached;

$R^6$ and $R^7$ when taken together are an optionally substituted $C_2$-$C_3$ alkylene chain connecting the atoms to which $R^6$ and $R^7$ are attached;

$R^8$ and $R^9$ when taken together are an optionally substituted $C_2$-$C_3$ alkylene chain connecting the atoms to which $R^8$ and $R^9$ are attached;

$R^{10}$ and $R^{11}$ when taken together are an optionally substituted $C_2$-$C_3$ alkylene chain connecting the atoms to which $R^{10}$ and $R^{11}$ are attached;

$R^5$ and $R^6$, when taken together with the nitrogen atom to which $R^5$ and $R^6$ are attached, form a 5-membered or a 6-membered unsaturated ring;

$R^9$ and $R^{10}$, when taken together with the nitrogen atom to which $R^9$ and $R^{10}$ are attached, form a 5-membered or a 6-membered unsaturated ring;

$L^1$ is an optionally substituted $C_2$-$C_{10}$ alkylene or optionally substituted $C_2$-$C_{20}$ heteroalkylene;

X is an activated ester, $N_3$, propynyl, maleimido, or —O—P(OCH$_2$CH$_2$CN)NR$^{12}$R$^{13}$ or X is:

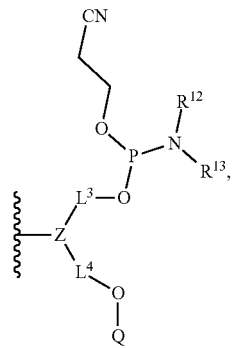

wherein $L^3$ and $L^4$ are independently an optionally substituted $C_2$-$C_{10}$ alkylene or optionally substituted $C_2$-$C_{30}$ heteroalkylene;

Q is a hydroxyl protecting group;

Z is CH, N, NHC(O)N, or OC(O)N; and $R^{12}$ and $R^{13}$ are independently optionally substituted $C_1$-$C_6$ alkyl.

In some embodiments, Formula I comprises one reactive group. In other embodiments, Formula I comprises two orthogonally reactive groups. In yet other embodiments, in addition to a reactive group such as phosphoramidite group, Formula I comprises a hydroxyl group protected with an acid-labile protective group, such as trityl or dimethoxytrityl group.

In certain embodiments of Formula I, $R^2$ is Cl and $R^3$ is H. In other embodiments, $R^4$ and $R^5$ form an optionally substituted $C_3$ alkylene chain connecting the atoms to which $R^4$ and $R^5$ are attached; $R^{11}$ and $R^{10}$ form an optionally substituted $C_3$ alkylene chain connecting the atoms to which $R^{11}$ and $R^{10}$ are attached; $R^6$ and $R^7$ form an optionally substituted $C_3$ alkylene chain connecting the to which $R^6$ and $R^7$ are attached; and $R^8$ and $R^9$ form an optionally substituted $C_3$ alkylene chain connecting the atoms to which $R^8$ and $R^9$ are attached. In some embodiments, $R^1$ is $L^1X$. In other embodiments, $R^1$ is methyl or ethyl. In some embodiments, the $C_3$ alkylene is propylene.

When the reactive moiety is a phosphoramidite, X is $OP(OCH_2CH_2CN)N(i-Pr)_2$. $L^1$ can comprise one or more heteroatoms selected from N, O, S, P, and combinations thereof. In some embodiments, $L^1$ is a PEG$_{2-10}$ linker. In other embodiments, $L^1$ is —CH$_2$CH$_2$OCH$_2$CH$_2$—.

In certain embodiments, $R^5$, $R^6$, $R^9$, and $R^{10}$ are $C_1$-$C_3$ alkyl, e.g., methyl.

In some embodiments, $L^3$ and $L^4$ are independently $C_2$-$C_6$ alkylene or —(OCH$_2$CH$_2$)$_m$— wherein m is an integer ranging from 2 to 6. In other embodiments, $L^3$ and $L^4$ are —CH$_2$CH$_2$—.

In certain embodiments, X is:

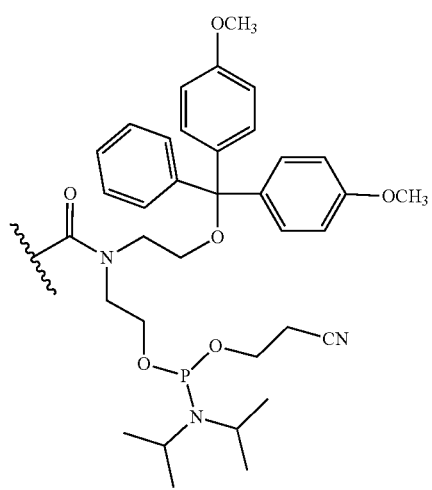

or

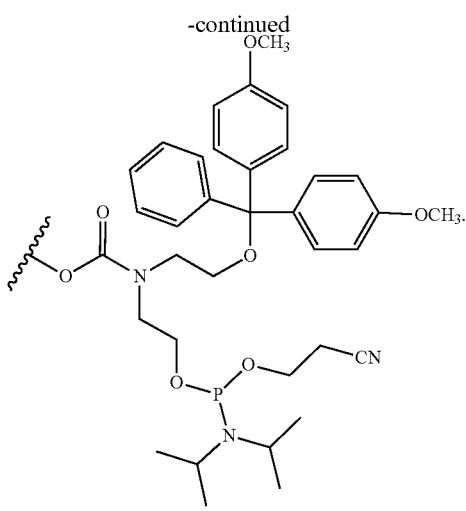

In Formulae shown herein, Q denotes a hydroxyl protecting group. Examples of such protective groups are known in the art (See, e.g., Peter G. M. Wuts, Greene's protective groups in organic synthesis (2006)). Suitable hydroxyl protecting groups include base-labile and acid-labile groups. In some embodiments, Q is a hydroxyl protective group that is compatible with the automated phosphoramidite oligonucleotide synthesis conditions, such as a trityl or dimethoxytrityl group.

Sulforhodamine dyes comprising other reactive moieties or groups are also within the scope of this disclosure; for example, reactive groups that can form chemical bonds with primary amines. These include isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, nitrophenyl esters, and fluorophenyl esters. Preferably, the reactive group is an activated ester. As used herein, an "activated ester" is an ester of a carboxylic acid that can react with an amino group with the formation of an amide. Activated esters include N-hydroxysuccinimide (NHS) esters, pentafluorophenyl esters, tetrafluorophenyl esters, and p-nitrophenyl esters. Activated esters that are generated in situ (e.g., by addition of an activating agent such as a carbodiimide to a carboxylic acid) are also included herein.

In some embodiments, the sulforhodamine dye has a structure represented by Formula IA:

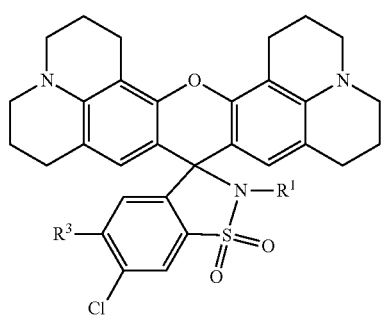

(IA)

or a stereoisomer, tautomer, or salt thereof, wherein $R^1$ is $L^1X$ and $R^3$ is H or halogen. In some embodiments of Formula IA, $R^1$ is $CH_2CH_2OCH_2CH_2OP(OCH_2CH_2CN)N(i-Pr)_2$.

In some embodiments, the sulforhodamine dye phosphoramidite is represented by Formula II:

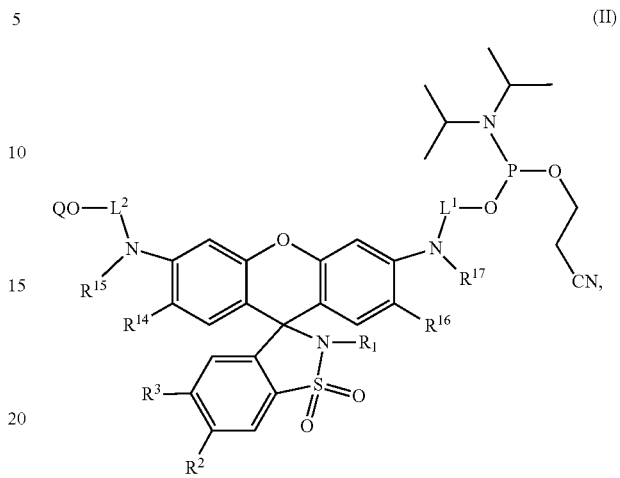

(II)

wherein:

$R^1$ is $C_1$-$C_6$ alkyl;

$R^2$ is H, halogen, or $SO_2NH_2$, $R^3$ is H or halogen;

$R^{14}$ and $R^{16}$, taken alone, are independently H, halogen, or optionally substituted $C_1$-$C_6$ alkyl;

$R^{15}$ and $R^{17}$, taken alone, are independently H or optionally substituted $C_1$-$C_6$ alkyl;

or $R^{14}$ and $R^{15}$, taken together, form an optionally substituted $C_2$-$C_3$ alkylene chain connecting the atoms to which $R^{14}$ and $R^{15}$ are attached;

$R^{16}$ and $R^{17}$, taken together, form an optionally substituted $C_2$-$C_3$ alkylene chain connecting the atoms to which $R^{16}$ and $R^1$ are attached;

Q is a hydroxyl protecting group; and $L^1$ and $L^2$ are independently an optionally substituted $C_2$-$C_{10}$ alkylene or optionally substituted $C_2$-$C_{20}$ heteroalkylene.

In some embodiments of Formula II, $R^3$ is H. In other embodiments, $R^2$ is H. In yet other embodiments, $R^2$ is Cl.

In other embodiments, $R^{14}$ and $R^{15}$ form a $C_2$ alkylene chain, optionally substituted with 1, 2, or 3 methyl groups, connecting the atoms to which $R^{14}$ and $R^{15}$ are attached; and yet other embodiments, $R^{16}$ and $R^{17}$ form a $C_2$ alkylene chain, optionally substituted with 1, 2, or 3 methyl groups, connecting the atoms to which $R^{16}$ and $R^{17}$ are attached. In certain embodiments, $R^{14}$ and $R^{15}$ form an ethylene chain substituted with 3 methyl groups and $R^{16}$ and $R^{17}$ form an ethylene chain substituted with 3 methyl groups.

In certain embodiments, $R^{14}$ and $R^{15}$ taken together and $R^{16}$ and $R^{17}$, taken together are:

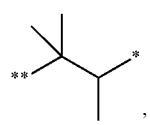

wherein * denotes the point of attachment to the nitrogen atom, and ** denotes the point of attachment to the aromatic carbon atom.

In certain embodiments, the compound is represented by Formula (IIA):
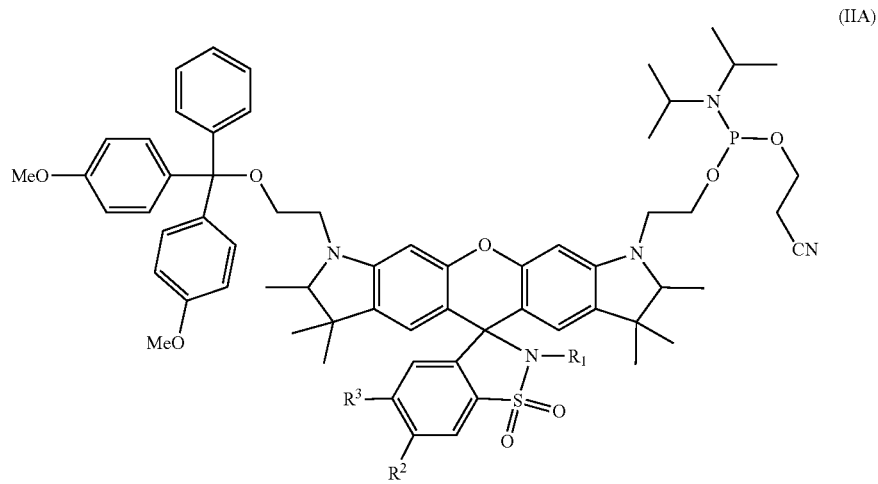
or a stereoisomer, tautomer, or salt thereof.
In particular embodiments, the compound is:
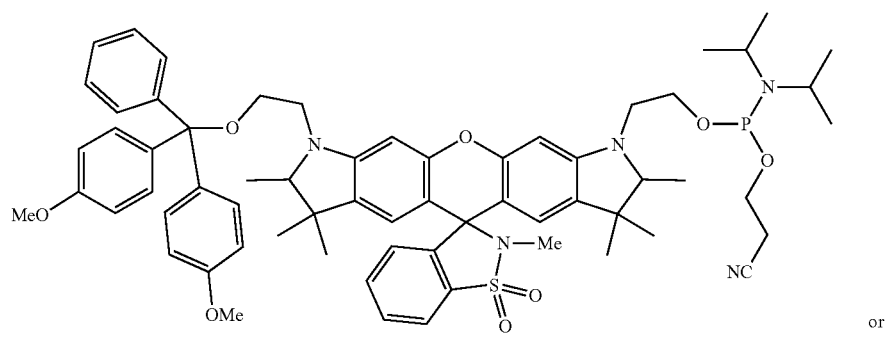
or
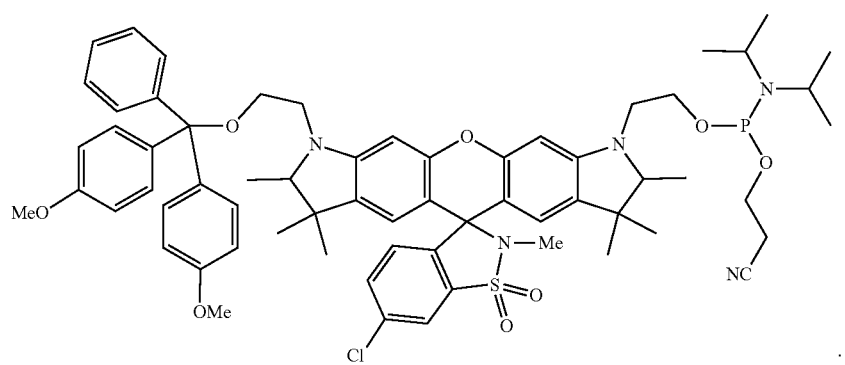

In some embodiments, the sulforhodamine dye phosphoramidites are compounds represented by Formula (III):

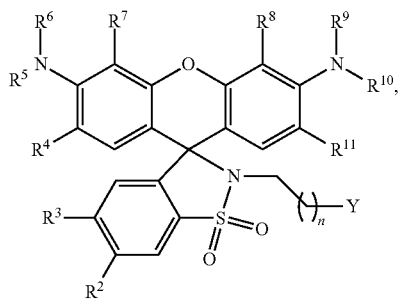

(III)

or a stereoisomer, tautomer, or salt thereof, wherein:

$R^2$ is H, halogen, or $SO_2NH_2$;

$R^3$ is halogen or H;

$R^4$, $R^7$, $R^8$, and $R^{11}$ when taken alone are independently H, halogen, or optionally substituted $C_1$-$C_6$ alkyl, $R^5$, $R^6$, $R^9$, and $R^{10}$ when taken alone are independently H or optionally substituted $C_1$-$C_6$ alkyl;

$R^4$ and $R^5$ when taken together are an optionally substituted $C_2$-$C_3$ alkylene chain connecting the atoms to which $R^4$ and $R^5$ are attached;

$R^6$ and $R^7$ when taken together are an optionally substituted $C_2$-$C_3$ alkylene chain connecting the atoms to which $R^6$ and $R^7$ are attached;

$R^8$ and $R^9$ when taken together are an optionally substituted $C_2$-$C_3$ alkylene chain connecting the atoms to which $R^8$ and $R^9$ are attached;

$R^{10}$ and $R^{11}$ when taken together are an optionally substituted $C_2$-$C_3$ alkylene chain connecting the atoms to which $R^{10}$ and $R^{11}$ are attached;

$R^5$ and $R^6$, when taken together with the nitrogen atom to which $R^5$ and $R^6$ are attached, form a 5-membered or a 6-membered unsaturated ring;

$R^9$ and $R^{10}$, when taken together with the nitrogen atom to which $R^9$ and $R^{10}$ are attached, form a 5-membered or a 6-membered unsaturated ring;

n is an integer from 1 to 9;

Y is:

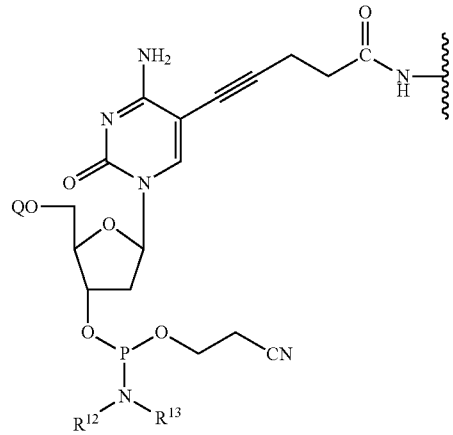

or

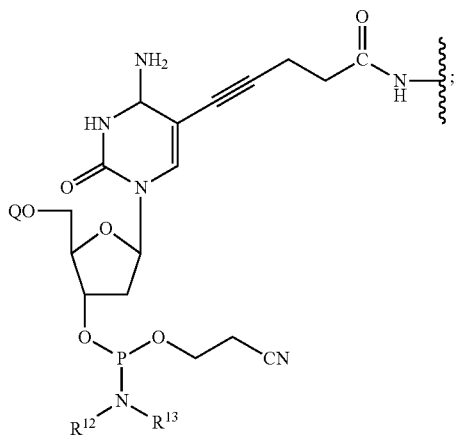

wherein:

Q is a hydroxyl protecting group; and $R^{12}$ and $R^{13}$ are independently optionally substituted $C_1$-$C_6$ alkyl.

In certain embodiments, $R^2$ is Cl and $R^3$ is H. In some embodiments, $R^4$ and $R^5$ form an optionally substituted $C_3$ alkylene chain connecting the atoms to which each is attached; $R^{11}$ and $R^{10}$ form an optionally substituted $C_3$ alkylene chain connecting the atoms to which each is attached; $R^6$ and $R^7$ form an optionally substituted $C_3$ alkylene chain connecting the atoms to which each is attached; and $R^8$ and $R^9$ form an optionally substituted $C_3$ alkylene chain connecting the atoms to which each is attached.

In certain embodiments, the compound is:

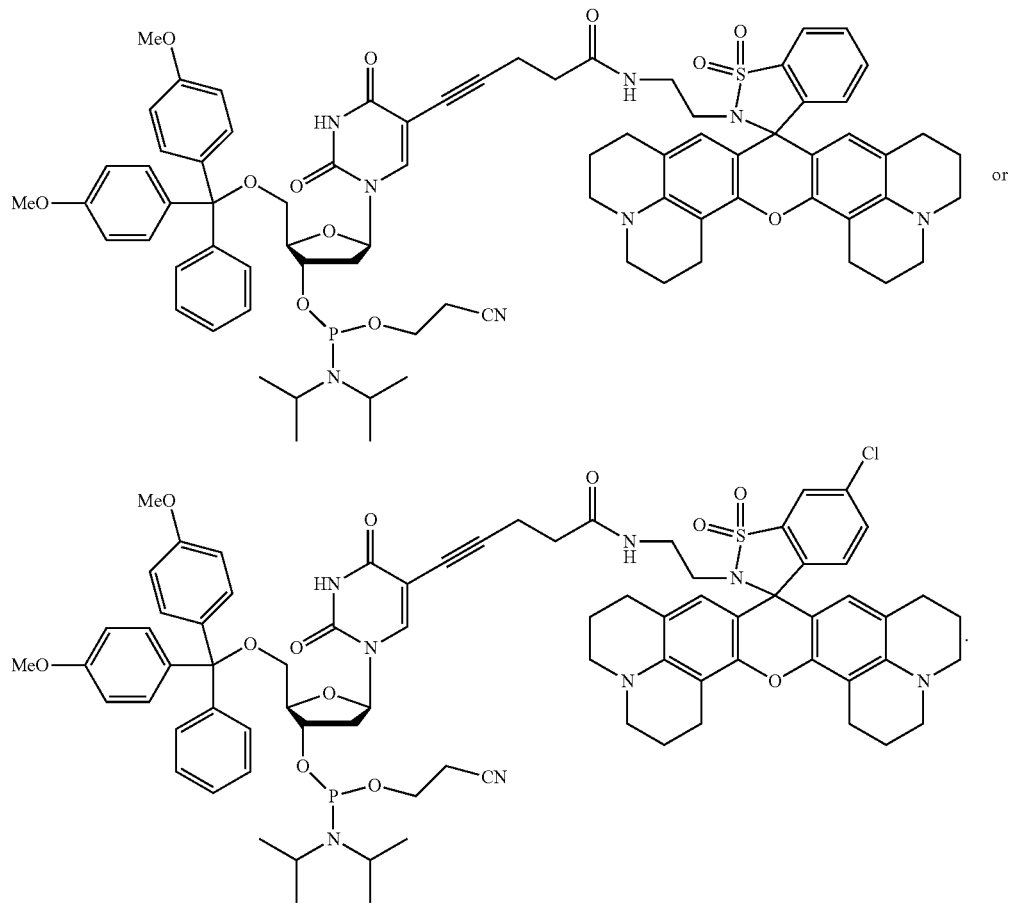

or

In some embodiments, the sulforhodamine dye is a compound represented by Formula VI:

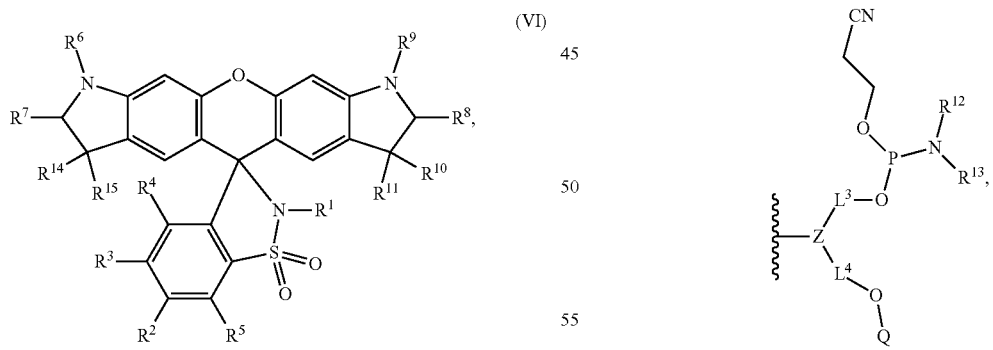

(VI)

or a stereoisomer, tautomer, or salt thereof, wherein:
$R^1$ is $L^1$-X;
$R^2$, $R^3$, $R^4$, and $R^5$ are independently H, halogen, $C_1$-$C_6$ alkyl, or $SO_2NH_2$;
$R^6$ and $R^9$ are independently H or optionally substituted $C_1$-$C_6$ alkyl;
$R^7$, $R^8$, $R^{10}$, $R^{11}$, $R^{14}$, and $R^{15}$ are independently H or optionally substituted $C_1$-$C_6$ alkyl;
$L^1$ is an optionally substituted $C_2$-$C_{10}$ alkylene or optionally substituted $C_2$-$C_{20}$ heteroalkylene;

X is an activated ester, $N_3$, propynyl, maleimido, or —O—P(OCH$_2$CH$_2$CN)NR$^{12}$R$^{13}$, or X is:

wherein $L^3$ and $L^4$ are independently an optionally substituted $C_2$-$C_{10}$ alkylene or optionally substituted $C_2$-$C_{30}$ heteroalkylene;
Q is a hydroxyl protecting group;
Z is CH, N, NHC(O)N, or OC(O)N; and
$R^{12}$ and $R^{13}$ are independently optionally substituted $C_1$-$C_6$ alkyl.

In some embodiments of Formula VI, $R^7$, $R^8$, $R^{10}$, $R^{11}$, $R^{14}$, and $R^{15}$ are methyl. In certain embodiments of Formula VI, X is —OP(OCH$_2$CH$_2$CN)N(i-Pr)$_2$.

In some embodiments of Formula VI, $L^1$ is a PEG$_{2-10}$ linker. In other embodiments of Formula VI, $L^1$ is —CH$_2$CH$_2$OCH$_2$CH$_2$—.

In some embodiments of Formula VI, $R^2$, $R^3$, $R^4$, and $R^5$ are H. In particular embodiments of Formula VI, $R^6$ is a C$_1$-C$_6$ alkyl optionally substituted with OH or C$_1$-C$_6$ acyloxy. In certain embodiments of Formula VI, $R^9$ is a C$_1$-C$_6$ alkyl optionally substituted with OH or C1-C6 acyloxy.

In certain embodiments of Formula VI, $R^6$ is an ethyl substituted with OH or OAc. In some embodiments of Formula VI, $R^9$ is an ethyl substituted with OH or OAc.

or a stereoisomer, tautomer, or salt thereof, wherein:
$R^1$, $R^2$, $R^3$, $R^4$, and $R^5$ are as described for compound of Formula VI; and
$Q^1$ and $Q^2$ are independently H or C1-C6 acyl.
In some embodiments, the compound is:

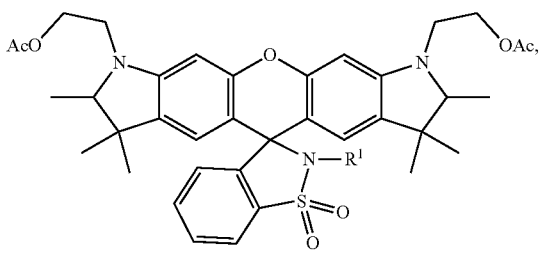

wherein $R^1$ is as defined for compound of Formula VI.
In particular embodiments, the compound is:

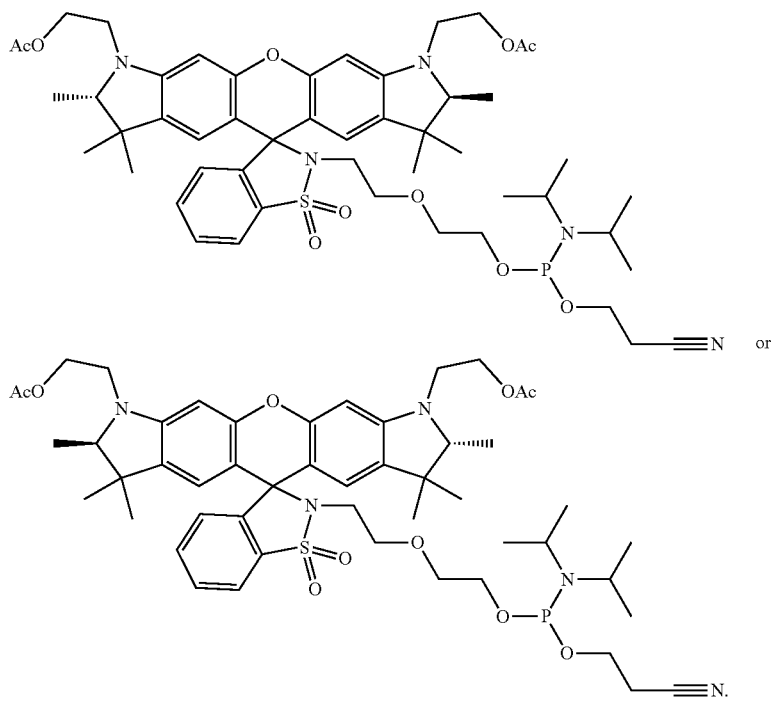

In some embodiments of Formula VI, the compound is:

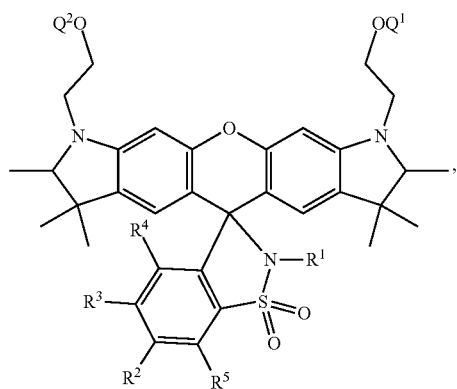

As used herein, the terms "alkyl," "alkenyl," and "alkynyl" include straight-chain, branched-chain, and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C, as C$_1$-C$_{10}$, C-C10, or C1-10.

The terms "heteroalkyl," "heteroalkenyl," and "heteroalkynyl," as used herein, mean the corresponding hydrocarbons wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as e.g. C3-C10, represent the sum of the number of carbon atoms in the cycle or chain and the number of such heteroatoms that are included as replacements for carbon atoms in the cycle or chain being described.

Typically, the alkyl, alkenyl, and alkynyl substituents contain 1-10 carbon atoms (alkyl) or 2-10 carbon atoms (alkenyl or alkynyl). Preferably, they contain 1-8 carbon atoms (alkyl) or 2-8 carbon atoms (alkenyl or alkynyl). Sometimes they refer to as "lower alkyl," meaning that they contain 1-6 carbon atoms (alkyl) or 2-6 carbon atoms (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

As used herein, the terms "alkylene," "alkenylene," and "alkynylene" include straight-chain, branched-chain, and cyclic divalent hydrocarbyl radicals, and combinations thereof.

Alkyl, alkenyl, and alkynyl groups can be optionally substituted to the extent that such substitution makes sense chemically. Typical substituents include, but are not limited to, halogens (F, Cl, Br, I), =O, =N—CN, =N—OR, =NR, OR, NR', SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, $C_1$-$C_8$ alkyl, $C_2$-$C_8$ heteroalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each R is optionally substituted with halogens (F, Cl, Br, I), =O, =N—CN, =N—OR', =NR, OR', NR'$_2$, SR', $SO_2R'$, $SO_2NR'_2$, NR'$SO_2R'$, NR'CONR'$_2$, NR'C(O)OR', NR'C(O)R', CN, C(O)OR', C(O)NR'$_2$, OC(O)R', C(O)R', and $NO_2$, wherein each R is independently H, $C_1$-$C_8$ alkyl, $C_2$-$C_8$ heteroalkyl, $C_1$-$C_8$ acyl, $C_2$-$C_8$ heteroacyl, $C_6$-$C_{10}$ aryl, or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl, or $C_5$-$C_{10}$ heteroaryl, each of which can be substituted by the substituents that are appropriate for the particular group.

While "alkyl" as used herein includes cycloalkyl and cycloalkylalkyl groups, the term "cycloalkyl" is used herein to describe a carbocyclic non-aromatic group that is connected via a ring carbon atom, and "cycloalkylalkyl" is used to describe a carbocyclic non-aromatic group that is connected to the molecule through an alkyl linker. Similarly, "heterocyclyl" is used to identify a non-aromatic cyclic group that contains at least one heteroatom as a ring member and that is connected to the molecule via a ring atom, which may be C or N; and "heterocyclylalkyl" may be used to describe such a group that is connected to another molecule through an alkylene linker. As used herein, these terms also include rings that contain a double bond or two, as long as the ring is not aromatic.

"Aromatic" or "aryl" substituent or moiety refers to a monocyclic or fused bicyclic moiety having the well-known characteristics of aromaticity; examples include phenyl and naphthyl. Similarly, the terms "heteroaromatic" and "heteroaryl" refer to such monocyclic or fused bicyclic ring systems which contain as ring members one or more heteroatoms. Suitable heteroatoms include N, O, and S, inclusion of which permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably, the monocyclic heteroaryls contain 5-6 ring members, and the bicyclic heteroaryls contain 8-10 ring members.

Aryl and heteroaryl moieties can be substituted with a variety of substituents including $C_1$-$C_8$ alkyl, $C_2$-$C_8$ alkenyl, $C_2$-$C_8$ alkynyl, $C_5$-$C_{12}$ aryl, $C_1$-$C_8$ acyl, and heteroforms of these, each of which can itself be further substituted; other substituents for aryl and heteroaryl moieties include halogens (F, Cl, Br, I), OR, $NR_2$, SR, $SO_2R$, $SO_2NR^2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, $C_5$-$C_{10}$ heteroaryl, $C_7$-$C_{12}$ arylalkyl, or $C_6$-$C_{12}$ heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

"Optionally substituted," as used herein, indicates that the particular group being described may have one or more hydrogen substituents replaced by a non-hydrogen substituent. In some optionally substituted groups or moieties, all hydrogen substituents are replaced by a non-hydrogen substituent, e.g., $C_1$-$C_6$ alkyl, $C_2$-$C_6$ heteroalkyl, alkynyl, halogens (F, Cl, Br, I), $N_3$, OR, $NR_2$, SR, $SO_2R$, $SO_2NR^2$, $NRSO_2R$, $NRCONR_2$, NRC(O)OR, NRC(O)R, CN, C(O)OR, C(O)$NR_2$, OC(O)R, C(O)R, oxo, and $NO_2$, wherein each R is independently H, $C_1$-$C_6$ alkyl, or $C_2$-$C_6$ heteroalkyl. Where an optional substituent is attached via a double bond, such as a carbonyl oxygen or oxo (=O), the group takes up two available valences, so the total number of substituents that may be included is reduced according to the number of available valences.

Salts, stereoisomers, and tautomers of the sulforhodamine compounds disclosed herein, such as compounds of formulae I, IA, II, IIA, and III, are also within the scope of this disclosure. As used herein, "stereoisomer" or "stereoisomers" refer to compounds that differ in the chirality of one or more stereocenters. Stereoisomers include enantiomers and diastereomers. As used herein, "tautomer" refers to alternate forms of a compound that differ in the position of a proton, such as enol-keto and imine-enamine tautomers. As used herein, "salt" of a compound refers to an ion of the compound ionically association with a counterion. A salt of a compound can be formed by the neutralization reaction of an acid and a base. Salts can be derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate. Although structures of the compounds disclosed herein can be shown in only one resonance form, it is understood that all resonance forms are included.

Synthesis of the sulforhodamine compounds disclosed herein, e.g., compounds of Formulae I, IA, II, IIA, III, and VI can be achieved in any suitable manner using techniques and methods known in the art. See, e.g., Beija M. et al, *Chem. Soc. Rev.*, (2009): 38, 2410-2433; Kreimerman et al, *Current Radiopharmaceuticals*, (2017): 10, 212-220; Corrie J. E. T. and Munasinghe V. R. *Dyes and Pigments* 79 (2008): 76-82; Corrie J. E. T. et al. *Bioconjugate Chem.* 12 (2001): 186-194. Examples 1-9 shown below illustrate synthesis of some exemplary compounds of the disclosure.

Labeled Polynucleotides

In another aspect, provided herein are sulforhodamine dye-labeled polynucleotides prepared by an automated oligonucleotide synthesis from the phosphoramidite sulforhodamine dyes disclosed herein. As used herein, "sulforhodamine dye-labeled polynucleotide" refers to a polynucleotide that prepared by an automated oligonucleotide synthesis from the phosphoramidite sulforhodamine dyes disclosed herein and incorporates a sulforhodamine dye moiety in either open or closed form.

In some embodiments, provided herein is a labeled polynucleotide comprising a compound of formula IV:

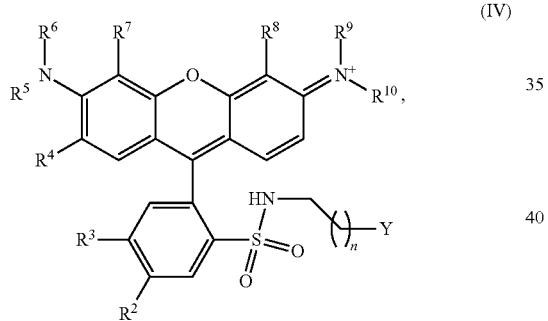

(IV)

or a stereoisomer, tautomer, or salt thereof, wherein:
$R^2$ is H, halogen, or $SO_2NH_2$;
$R^3$ is H or halogen;
$R^4$, $R^7$, $R^8$, and $R^{11}$ when taken alone are independently H, halogen, or optionally substituted $C_1$-$C_6$ alkyl,
$R^5$, $R^6$, $R^9$ and $R^{10}$ when taken alone are independently H or optionally substituted $C_1$-$C_6$ alkyl;
$R^4$ and $R^5$ when taken together are an optionally substituted $C_2$-$C_3$ alkylene chain connecting the atoms to which $R^4$ and $R^5$ are attached;
$R^6$ and $R^7$ when taken together are an optionally substituted $C_2$-$C_3$ alkylene chain connecting the atoms to which $R^6$ and $R^7$ are attached;
$R^8$ and $R^9$ when taken together are an optionally substituted $C_2$-$C_3$ alkylene chain connecting the atoms to which $R^8$ and $R^9$ are attached;
$R^{10}$ and $R^{11}$ when taken together are an optionally substituted $C_2$-$C_3$ alkylene chain connecting the atoms to which $R^{10}$ and $R^{11}$ are attached;
$R^5$ and $R^6$, when taken together with the nitrogen atom to which $R^5$ and $R^6$ are attached, form a 5-membered or a 6-membered unsaturated ring;

$R^9$ and $R^{10}$, when taken together with the nitrogen atom to which $R^9$ and $R^{10}$ are attached, form a 5-membered or a 6-membered unsaturated ring;
n is an integer from 1 to 9;
Y is:

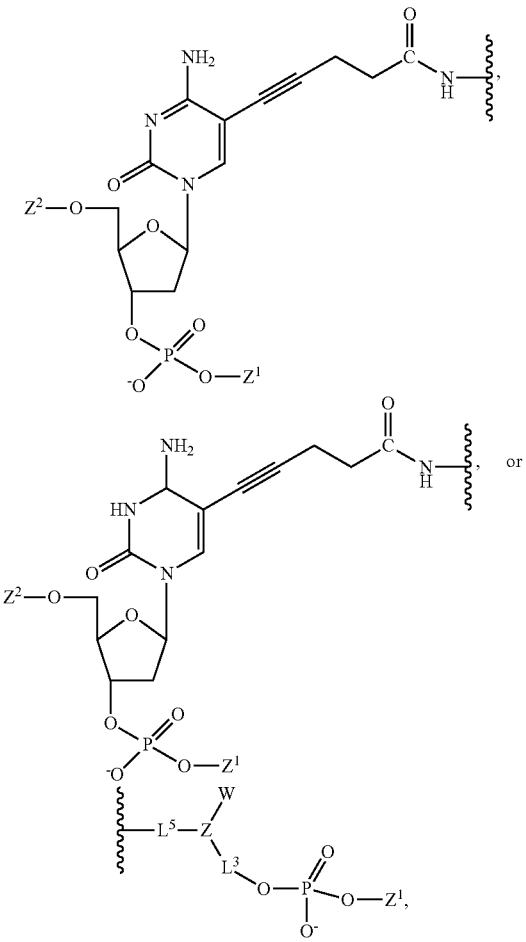

wherein:
the wavy line is the point of attachment to Formula IV;
$L^3$, $L^4$, and $L^5$ are independently an optionally substituted $C_2$-$C_{10}$ alkylene or optionally substituted $C_2$-$C_{30}$ heteroalkylene;
Z is CH, N, NHC(O)N, or OC(O)N;
$R^{12}$ and $R^{13}$ are independently optionally substituted $C_1$-$C_6$ alkyl;
W is H or $L^4$-O-$Z^2$;
$Z^1$ is a nucleotide or oligonucleotide; and
$Z^2$ is a nucleotide, oligonucleotide, or H.

In some embodiments, $R^4$ and $R^5$ form an optionally substituted $C_3$ alkylene chain connecting the atoms to which each is attached; $R^{11}$ and $R^{10}$ form an optionally substituted $C_3$ alkylene chain connecting the atoms to which each is attached; $R^6$ and $R^7$ form an optionally substituted $C_3$ alkylene chain connecting the atoms to which each is attached; and $R^8$ and $R^9$ form an optionally substituted $C_3$ alkylene chain connecting the atoms to which each is attached. In certain embodiments, $R^2$ is Cl and $R^3$ is H.

$L^3$ can comprise one or more heteroatoms selected from N, O, S, P, and combinations thereof. In some embodiments of Formula IV, $L^3$ is —(OCH$_2$CH$_2$)$_n$—, wherein n is an integer from 1 to 5.

In some embodiments, provided herein is a labeled polynucleotide comprising a compound of formulae VA or VB:

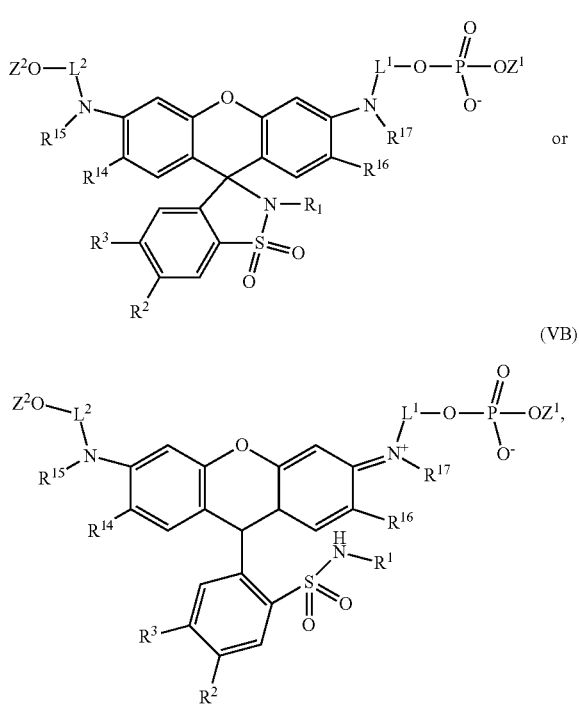

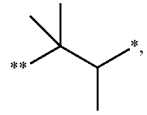

wherein * denotes the point of attachment to the nitrogen atom, and ** denotes the point of attachment to the aromatic carbon atom.

Labeled polynucleotides disclosed herein can comprise one or more additional compounds. In some embodiments of the present disclosure, a polynucleotide comprises a minor groove binder. In some embodiments, a polynucleotide comprises an intercalator.

Typically, a polynucleotide labeled with the dyes disclosed herein is a polynucleotide wherein the backbone comprises 2'-deoxyribose or ribose. However, a labeled polynucleotide can comprise one or more modifications. In some embodiments, a polynucleotide comprises a sugar modification, e.g., a modified sugar. Various sugar modifications are useful. Some non-limiting sugar modifications include arabinose, d-arabino-hexitol, 2-fluoroarabinose, xylulose, hexose, or a bicyclic sugar.

A labeled polynucleotide of the disclosure can comprise one or more backbone modifications. In some embodiments, the polynucleotide comprises a backbone modification. In some embodiments, a backbone modification is selected from the group consisting of a modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, and a combination of two or more of any of the foregoing. In a particular embodiment of the present disclosure, the backbone modification is a modified sugar phosphate backbone.

Labeled polynucleotides disclosed herein can comprise one or more modified or unnatural bases. Modified bases include modified thymine and cytosine bases (e.g, those disclosed in U.S. Pat. Nos. 9,598,455 and 9,598,456), 2,6-diaminopurine bases, universal bases, and the like. Labeled polynucleotides disclosed herein can comprise non-nucleoside segments or non-nucleoside monomers (e.g., linkers such as poly(ethyleneglycol) linkers).

In some embodiments, the polynucleotide disclosed herein is probe, e.g. a 5'-nuclease PCR probe. In certain embodiments, the polynucleotide further comprises one or more additional labels, for example, a fluorescence quencher. As one of ordinary skill in the art will appreciate, the location of a label within the oligonucleotide can vary and is not limited to the disclosure herein.

In some embodiments, provided herein is a modified polynucleotide which comprises a sulforhodamine dye moiety as a fluorophore on one end of its sequence and a fluorescence quencher on the other end of its sequence, so that the fluorescence quencher suppresses the fluorescence signal of the fluorophore in the intact probe (i.e., the oligonucleotide being used as a probe) via an energy transfer mechanism such as fluorescence resonance energy transfer or a stereoisomer, tautomer, or salt thereof, wherein:
$R^1$ is an optionally substituted $C_1$-$C_6$ alkyl;
$R^2$ is H, halogen, or $SO_2NH_2$,
$R^3$ is H or halogen;
$R^{14}$ and $R^{16}$, when taken alone, are independently H, halogen, or optionally substituted $C_1$-$C_6$ alkyl;
$R^{15}$ and $R^{17}$, when taken alone, are independently H or optionally substituted $C_1$-$C_6$ alkyl;
$R^{14}$ and $R^{15}$, when taken together, form an optionally substituted $C_2$-$C_3$ alkylene chain connecting the atoms to which $R^{14}$ and $R^{15}$ are attached;
$R^{16}$ and $R^{17}$, when taken together, form an optionally substituted $C_2$-$C_3$ alkylene chain connecting the atoms to which $R^{16}$ and $R^{17}$ are attached;
$L^1$ and $L^2$ are independently an optionally substituted $C_2$-$C_{10}$ alkylene or optionally substituted $C_2$-$C_{20}$ heteroalkylene;
$Z^1$ is a nucleotide or oligonucleotide; and
$Z^2$ is a nucleotide, oligonucleotide, or H.

In some embodiments of formulae VA or VB, $R^3$ is H. In other embodiments, $R^2$ is H. In yet other embodiments, $R^2$ is Cl.

In other embodiments of formulae VA or VB, $R^{14}$ and $R^{15}$ form a $C_2$ alkylene chain, optionally substituted with 1, 2, or 3 methyl groups, connecting the atoms to which $R^{14}$ and $R^{15}$ are attached; and yet other embodiments, $R^{16}$ and $R^{17}$ form a $C_2$ alkylene chain, optionally substituted with 1, 2, or 3 methyl groups, connecting the atoms to which $R^{16}$ and $R^{17}$ are attached. In certain embodiments, $R^{14}$ and $R^{15}$ form an ethylene chain substituted with 3 methyl groups and $R^{16}$ and $R^{17}$ form an ethylene chain substituted with 3 methyl groups.

In certain embodiments of formulae VA or VB, $R^{14}$ and $R^{15}$ taken together and $R^{16}$ and $R^{17}$, taken together are:

("FRET"). When a polymerase extends a primer along a template to which the probe has also hybridized, the 5'-nuclease activity of the polymerase cleaves the probe, thereby allowing the fluorophore to diffuse away from the fluorescence quencher so that the fluorescent signal is now detected. The signal increases with each PCR cycle proportionally to the amount of probe that is cleaved, and thus, proportionally to the amount of amplification product (e.g., amplicon, target sequence). This allows direct detection and quantification of the target DNA sequence.

In some embodiments, the sulforhodamine dye moiety is attached to a base that is at least one nucleotide position away from the end of the sequence of the labeled polynucleotide and the fluorescence quencher is attached to a base that is at least one nucleotide position away from the other end of the modified polynucleotide. In some embodiments, the fluorophore, e.g., the sulforhodamine dye moiety, and the fluorescence quencher are located internally within a probe. As one of ordinary skill in the art will appreciate, the location of the fluorophore and/or the fluorescence quencher within a probe can vary and is not limited.

In some embodiments, the fluorophore, e.g., the sulforhodamine dye moiety, and fluorescence quencher are not at the ends of a FRET probe. In some embodiments, the emission spectrum of the sulforhodamine dye overlaps considerably with the absorption spectrum of the fluorescence quencher. However, such spectral overlap is less important or not required when quenching involves a collisional mechanism, or the overlap is increased, for example, due to reaction conditions or probe structure.

A great deal of practical guidance available in the art for selecting appropriate fluorophore-quencher pairs for particular probes. See, for example, FLUORESCENCE SPECTROSCOPY (Marcel Dekker, New York, 1971). Quenchers useful for inclusion in probes disclosed herein include bis-azoquenchers (e.g., those disclosed in U.S. Pat. No. 6,790,945), quenchers available from Biosearch Technologies, Inc. (Black Hole™ Quenchers: BHQ-1, BHQ-2, and BHQ-3), TAMRA, carboxytetramethyl rhodamine, 4-((4-(dimethylamino)phenyl)azo)benzoic acid (Dabcyl), Zen® quencher, Blackberry® quencher, 2,3-Dichloro-5,6-dicyano-1,4-benzoquinone (DDQ)-I, and 2-[6-(1,3-dihydro-2H-isoindol-2-yl)-9-[2-[(4-[(2,5-dioxopyrrolidin-1-yl)o-xy] carbonyl piperidin-1-yl]sulfo-nyl]phenyl]-3H-xanthen-3-ylidene]-2,3-dihydro-1H-isoindolium chloride (QSY 21) and other known in the art quenchers.

In yet another aspect, disclosed herein is a method for preparing a labeled conjugate of a ligand, comprising contacting a ligand with a sulforhodamine dye compounds provided herein in a suitable solvent under conditions sufficient to covalently attach the compound to the ligand thereby forming the dye-labeled conjugate. Suitable ligands include biomolecules (e.g., a polynucleotide, a protein, an antibody, a peptide, or a polysaccharide), synthetic polymers (e.g. a polymer with an ethylenic backbone, such as polyacrylic acid), and solid supports (e.g., controlled pore glass or polystyrene).

In some embodiments, the ligand is a polynucleotide. In certain embodiments, the conditions sufficient to covalently attach the compound of the present disclosure to the ligand, i.e., oligonucleotide or polynucleotide, are automated phosphoramidite oligonucleotide synthesis conditions. Automated phosphoramidite oligonucleotide synthesis conditions used to synthesize and deprotect synthetic oligonucleotides are well-known in the art, and are described, for example, in Current Protocols in Nucleic Acid Chemistry, Vol. I, Beaucage et al., Eds., John Wiley & Sons, 2002, the disclosure of which are incorporated herein by reference.

The phosphoramidite method of oligonucleotide, e.g., DNA, synthesis is considered as the standard synthesis method used in most automated synthesizers. Building blocks used for synthesis are commonly referred to as nucleotide building blocks, monomers, or nucleoside phosphoramidites, which are activated nucleoside derivatives (phosphoramidites). An acid-cleavable protecting group, typically, the dimethoxytrityl (DMT) group, is used to protect the 5'-end of the nucleoside and a β-cyanoethyl group is used to protect the 3'-phosphite moiety. A monomer may also include additional groups that serve to protect other moieties, e.g., reactive primary amines in the nucleobases. The protecting groups are selected to prevent branching or other undesirable side reactions from occurring during synthesis. Skilled artisans will be readily able to select protecting groups having properties suitable for use under specific synthesis and deprotection and/or cleavage conditions. A wide variety of amine protecting groups are taught, for example in, Greene & Wuts, "Protective Groups In Organic Chemistry," 3d Edition, John Wiley & Sons, 1999 (hereinafter "Green & Wuts").

Typically, oligonucleotides are synthesized on solid supports, e.g., control pore glass (CPG)- or polystyrene-filled column, a membrane, or a similar material. An oligonucleotide is usually synthesized from the 3' to the 5'-end. The first nucleotide building block or monomer is usually anchored to the support, typically, via a linker, such as a long chain alkylamine-controlled pore glass (LCAA-CPG).

In some embodiments, synthesis methods that employ phosphoramidite reagents involve multiple rounds of: (i) DMT deprotection to reveal a free hydroxyl, which can be effected, for example, by treatment with 2.5% or 3% di- or tri-chloroacetic acid in dichloromethane; (ii) coupling of nucleoside or other phosphoramidite reagents to the free hydroxyl, which can be carried out, for example, in acetonitrile containing tetrazole (e.g., 0.45 M or 0.5 M tetrazole); (iii) oxidation, which can be carried out, for example, by treatment with $I_2$/2,6-lutidine/$H_2O$; and capping, which can be carried out, for example, by treatment with 6.5% acetic anhydride in tetrahydrofuran (THF) activated with 10% 1-methylimidazole (NMI) in THF.

Other conditions for carrying out the various steps in the synthesis are also known in the art and can be used herein. For example, phosphoramidite coupling can be carried out in acetonitrile containing 0.25 M 5-ethylthio-1H-tetrazole, 0.25 M 4,5-dicyanoimidazole (DCI) or 0.25 M 5-benzylthio-1H-tetrazole (BTT). Oxidation can be carried out with 0.1 M, 0.05 M or 0.02 M $I_2$ in THF/$H_2O$/pyridine (7:2:1). Capping can be carried out by treatment with THF/lutidine/acetic anhydride followed by treatment with 16% NMI in THF.

Removal of any protecting groups and cleavage from the synthesis reagent is typically achieved by treatment with concentrated ammonium hydroxide at 60° C. for 1-12 hours, although nucleoside phosphoramidites protected with groups that can be removed under milder conditions, such as by treatment with concentrated ammonium hydroxide at room temperature for 4-17 hours or treatment with 0.05 M potassium carbonate in methanol, or treatment with 25% t-butylamine in water/EtOH, are also known and can be used.

The term "cleavage" in reference to solid phase oligonucleotide synthesis means breaking the bond which attaches an oligonucleotide to a solid phase support. In some embodiments, cleavage involves hydrolysis of a succinate ester bond between the 3' hydroxyl of an attached oligonucleotide and the solid phase support.

The term "deprotection" as used herein means removing protection groups from the exocyclic amines of the heterocyclic bases of an oligonucleotide. Usually, deprotection involves hydrolysis of an amide moiety consisting of an exocyclic amine and an amino protection group, e.g. benzoyl or isobutyryl. Various techniques and methods of deprotection are known in the art.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

The invention is illustrated by the following Examples. These Examples are included for illustrative purposes only, and are not intended to limit the invention.

EXAMPLES

Proton ($^1$H, 400 MHz) and phosphorous ($^{31}$P, 160 MHz) nuclear magnetic resonance (NMR) spectra were obtained on a Bruker Biospin 400 instrument. NMR samples were prepared in DMSO-$d_6$ and CD$_3$CN and residual protonated solvent was used as an internal chemical shift standard. LCMS data were obtained by electrospray ionization (ESI) on Agilent 1200 series (LC/MSD Trap XCT Plus) and Agilent 1260 infinity (6130 Quadrupole LC/MS) instruments. Automated chromatography on silica gel 60 was carried out using Biotage Isolera LS and Teledyne ISCO Torrent® Combi Flash instruments. Analytical thin layer chromatography was conducted on aluminum-backed silica gel 60 F254, and plates were visualized under a UV lamp (254 and 365 nm). All reagents were from commercial sources unless indicated otherwise.

Example 1: Synthesis of Sulforhodamine Dye 51

This example describes synthesis of an exemplary sulforhodamine dye S1 which comprises a phosphoramidite group. This dye is suitable for incorporation into the 5' end of an oligonucleotide via standard automated oligonucleotide synthesis.

Compound S1 was prepared according to the procedure outlined in Scheme 1.

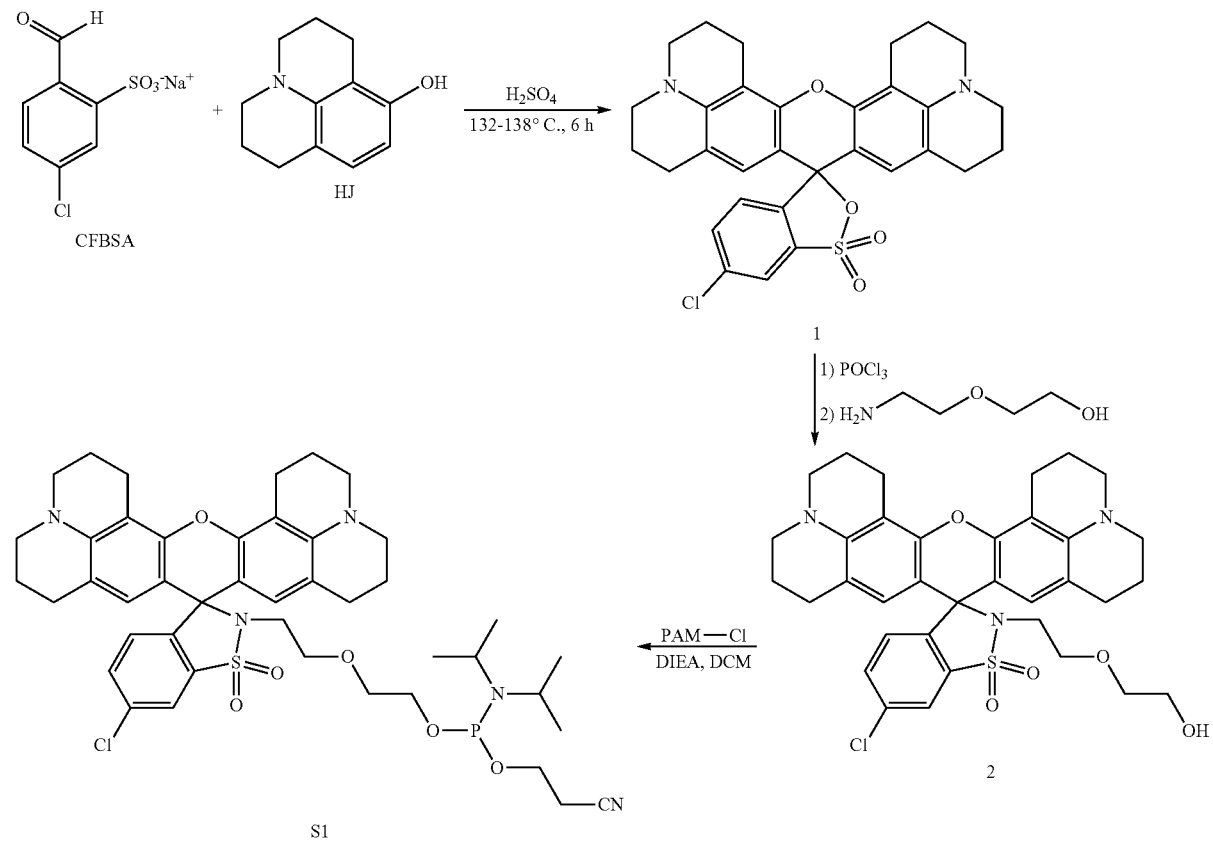

Scheme 1

Compound 1

A dry mixture of compounds CFBSA (4.0 g, 1 eq) and 8-hydroxyjulolidine (HJ, 6.2 g, 2 eq) was added portion wise to an aqueous sulfuric acid solution (60%, 32 mL) in a multiport vessel (≥3; any ports not in use were open to the atmosphere) at 132-138° C. The reaction progress was monitored using HPLC. When the reaction was completed (7-16 hr), the reaction mixture was allowed to cool to room temperature and then it was poured into dilute cold aqueous NaOH (110 mL) solution. After pH adjustment to 8.5-11, the product of the cyclocondensation reaction (Compound 1) was isolated by filtration and then was dried in a vacuum oven at 45-50° C. for >16 h. The product was then dissolved in 130 mL of dichloromethane (DCM), and the solution was filtered. Concentration of the DCM layer afforded Compound 1 (6 g, 65%) which was used in the next step without additional purification. LCMS: m/z 561.5; [M+H] $^1$H NMR (DMSO-d$_6$, 400 MHz): δ7.94 (d, 1H, J=2.4 Hz), 7.60 (dd, 1H, J=8.0, 2.4 Hz), 7.10 (d, 1H, J=8.0 Hz), 6.59 (s, 2H), 3.58 (m, 8H), 2.98 (m, 4H), 2.52 (m, 4H), 1.99 (m, 4H), 1.83 (m, 4H).

Compound 2

Compound 1 (8 g, 14.3 mmol) was suspended in anhydrous DCM (120 mL) at room temperature (RT) and treated with POCl$_3$ (13.1 mL, 10 eq) overnight. The reaction progress/completion was followed by TLC (10% MeOH/DCM). When the reaction was complete, the mixture was concentrated under vacuum, and the resulting foam was dried under vacuum for 90-150 min at 40° C. The foam was then dissolved in anhydrous dichloromethane (150 mL) under argon. The reaction solution was cooled to 0-5° C. and treated with N,N-diisopropylethylamine (DIEA) (25 mL, 10 eq) and 2-aminoethoxyethanol (AEE) (7.2 mL, 5 eq) while maintaining the temperature below 8° C. The reaction was stirred while allowing to warm up to RT over 1-2 h, then stirred at RT overnight. The reaction progress was monitored by TLC (10% MeOH/DCM). The reaction mixture was diluted with DCM (250 mL) and washed with 1 N HCl (2×185 mL), brine (1×200 mL) and dried over Na$_2$SO$_4$. Filtration, concentration and purification using silica gel column purification afforded pure Compound 2 (3.74 g, 40% yield). LCMS: m/z 648.5 [M+H]; $^1$H NMR (DMSO-d$_6$, 400 MHz): δ 8.19 (d, 1H, J=2.0 Hz), 7.60 (dd, 1H, J=8.0, 2.0 Hz), 6.95 (1H, d, J=8 Hz), 6.28 (s, 2H), 4.4 (t, 1H, J=5.6 Hz), 3.30 (m, 3H), 3.15 (m, 12H), 2.90 (t, 2H, J=6.8 Hz), 2.82 (m, 4H), 2.51 (m, 4H), 1.96 (m, 4H), 1.81 (m, 4H).

Compound S1

Compound 2 (2.8 g, 4.3 mmol) was placed in a 3-necked round-bottom flask and dried under high vacuum (≤2 mBar) for at least 90 min. The dried compound was then dissolved in anhydrous DCM (88 mL) under argon. The reaction mixture was cooled to 0-5° C., and DIEA (7.5 mL, 10 eq) was added followed by drop-wise addition of 2-cyanoethyl N,N-diisopropylchlorophosphoramidite (PAM-Cl) (1.2 mL, 1.4 eq) while maintaining the internal temperature at 0-5° C. The reaction was stirred while allowing warm up to RT until completion (2-3 h). The reaction was diluted with DCM (88 mL) and washed with NaHCO$_3$ (2×45 mL) and brine (45 mL), and the organic layer was dried over Na$_2$SO$_4$. Filtration, concentration, and silica gel column purification of crude product afforded the pure product as a pink solid (1.75 g, 48% yield). LCMS: m/z 848.2 [M+H]; $^{31}$P NMR (CD3CN, 160 MHz): δ 148.25; $^1$H NMR (DMSO-d$_6$, 400 MHz): δ 8.18 (d, 1H, J=2 Hz), 7.59 (dd, 1H, J=8.4, 2.0 Hz), 6.96 (d, 1H, J=8 Hz), 6.27 (s, 2H), 3.66 (m, 2H), 3.27 (t, 2H, J=5.2 Hz), 3.20 (t, 1H, J=6.8 Hz), 3.10-3.20 (m, 8H), 2.90 (t, 2H, 6.8 Hz), 2.82 (t, 4H, J=6.4 Hz), 2.70 (t, 2H, J=7.0 Hz)), 2.40-2.51 (m, 4H), 1.95 (m, 4H), 1.78 (m, 4H), 1.13 (d, 6H, J=8 Hz), 1.05 (d, 6H, J=8 Hz).

Example 2: Synthesis of Sulforhodamine Dye S2

This example describes synthesis of an exemplary sulforhodamine dye S2 which comprises a phosphoramidite group and a hydroxyl group protected with dimethoxytrityl group. This dye is suitable for incorporation into the 5'-end or in a middle position of an oligonucleotide via standard automated oligonucleotide synthesis.

Compound S2 was prepared according to the procedure outlined in Scheme 2.

Scheme 2

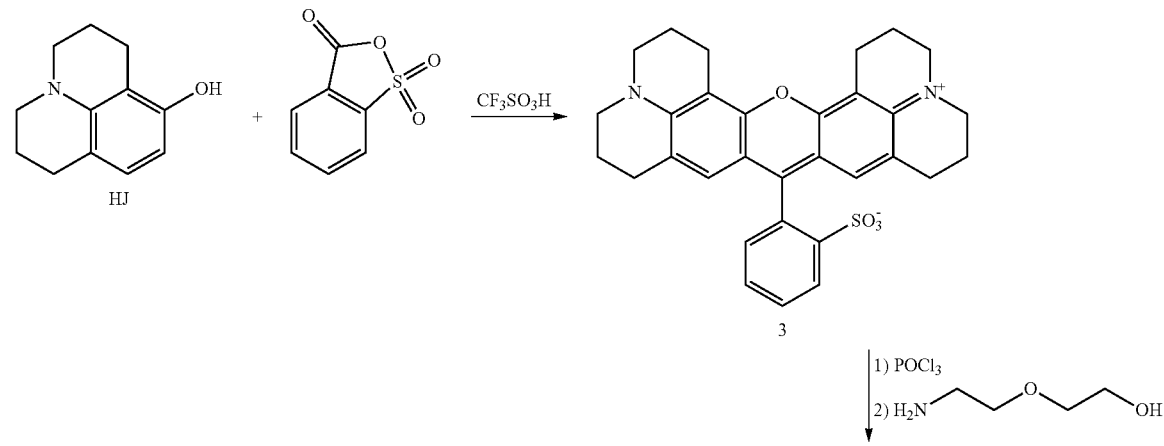

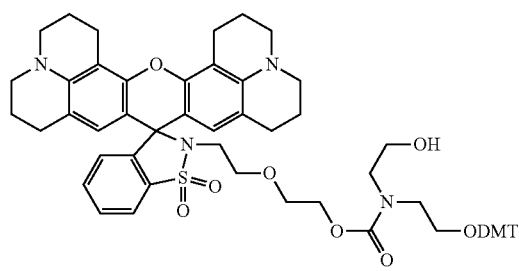

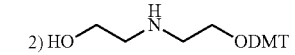

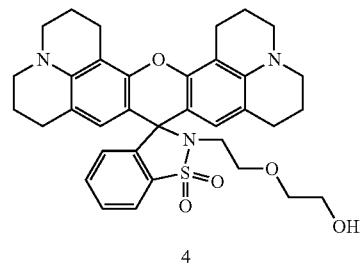

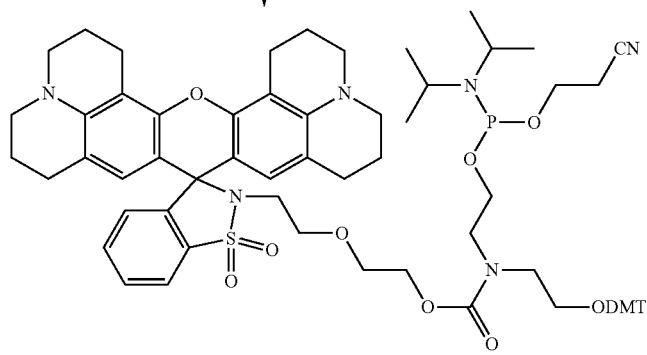

Compound 3

Trifluoromethane sulfonic acid (50 mL) in a 150 mL round bottom flask was cooled to 0° C. under argon atmosphere. 8-Hydroxyjulolidine (HJ) (15.0 g, 79.3 mmol) was added portion wise over 20 minutes, and the mixture was allowed to warm to RT then stirred at RT until the 8-hydroxyjulolidine dissolved completely. 2-Sulfobenzoic acid cyclic anhydride (10.95 g, 59.5 mmol) was added in one portion. The mixture was heated to 110° C. and stirred for 18 h then cooled to RT. The reaction mixture was added dropwise to a mixture of 3M NaOAc (300 mL) and crushed ice (200 mL). To the resulting mixture, DCM was added (500 mL), and the mixture was transferred to a separatory funnel. The organic layer was collected and washed with water and brine. The combined aqueous layers were back-extracted with DCM, and all organic layers were combined. After drying over $Na_2SO_4$, the solution was filtered, and DCM was removed under vacuum. The product was purified by chromatography on silica gel (3"×7" bed) using 2% to 10% water/acetonitrile (ACN). A dark red impurity comes off the column with the solvent front. $R_f$ of product on TLC is 0.4 in 10% water/ACN. Concentration of product-containing fractions afforded the Compound 3 (8.34 g, 40%). $^1$H NMR (DMSO-$d_6$, 400 MHz): δ 7.80 (d, 1H, J=6.8 Hz), 7.60 (t, 1H, J=7.6 Hz), 7.51 (t, 1H, J=7.4 Hz), 7.09 (d, 1H, J=7.4 Hz) 6.58 (s, 2H), 3.49 (m, 8H), 2.98 (m, 4H), 2.62 (m, 4H), 2.02 (m, 4H), 1.83 (m, 4H); LCMS: m/z 527.5 [M+H].

Compound 4

Under argon, Compound 3 (6.50 g, 12.3 mmol) was dissolved in 60 mL of anhydrous DCM, and $POCl_3$ (5.00 mL, 53.6 mmol) was added. The mixture was stirred at RT for 24 h. DCM was removed under reduced pressure at RT, and then the excess $POCl_3$ was removed under reduced pressure at 60° C. to yield a foam. The foam was dissolved in 150 mL of anhydrous DCM under argon, and the solution was cooled to 0° C. Diisopropylethylamine (22.0 mL, 124 mmol) was added, the mixture was again cooled to 0° C., and 2-(2-aminoethoxy)ethanol (6.20 mL, 62.2 mmol) was added. The reaction mixture was allowed to warm to RT and stirred for 2.5 h. The reaction was quenched by addition of enough methanol to dissolve all solids. The mixture was washed with saturated $NaHCO_3$, water, and brine. The organic layer was dried over $Na_2SO_4$. The product was chromatographed on silica gel (3"×6"), 30% EtOAc/hexanes to 60% EtOAc/hexanes containing 10% triethylamine (TEA), to yield 4.56 g (60%) of Compound 4. $^1$H NMR (DMSO-$d_6$, 400 MHz): δ 7.94 (dd, 1H, J=3.6, 2.8 Hz), 7.58 (dd, 2H, J=5.6, 3.2 Hz), 6.93 (dd, 1H, J=6.4, 3.2 Hz), 6.27 (s, 2H), 4.4 (t, 1H, J=5.6 Hz), 3.31 (m, 2H), 3.07-3.20 (m, 12H), 2.89 (t, 2H J=7.2 Hz), 2.83 (t, 4H, J=6.4 Hz)), 2.45 (m, 4H), 1.95 (m, 4H), 1.79 (m, 4H). LCMS: m/z 614.5 [M+H].

Compound 5

Under argon, Compound 4 (1.58 g, 2.57 mmol) was dissolved in 50 mL of anhydrous DCM, and TEA (3.60 mL, 25.8 mmol) was added, followed by p-nitrophenylchlororformate (777 mg, 3.85 mmol). The resulting mixture was stirred at RT for 18 h. Mono-DMT-diethanolamine (2.09 g, 5.13 mmol) was added, and stirring at RT continued for another 24 h. The mixture was washed with saturated $NaHCO_3$, water, and brine and dried over $Na_2SO_4$. Purification of the product by chromatography on silica gel, 40% EtOAc/hexanes to 70% EtOAc/hexanes containing 10% TEA, yielded 1.78 g (66%) of Compound 5. $^1$H NMR (DMSO-$d_6$, 400 MHz): δ 7.85 (m, 1H), 7.42 (m, 4H), 7.29 (m, 7H), 6.99 (m, 1H), 6.82 (d, 4H, J=8.8 Hz), 6.44 (s, 2H), 4.10 (m, 1H), 4.05 (m, 1H), 3.79 (s, 6H), 3.76 (m, 1H), 3.66 (m, 1H), 3.57-3.21 (m, 10H), 3.18-3.02 (m, 11H), 2.89 (t, 4H, J=6.5 Hz), 2.54 (m, 4H), 2.04 (m, 4H), 1.87 (m, 4H). LCMS: m/z 1047.7 [M+H].

Compound S2

Under argon, Compound 5 (300 mg, 0.287 mmol) was dissolved in 20 mL of anhydrous DCM. DIEA (0.500 mL, 2.87 mmol) was added, followed by PAM-Cl (0.080 mL, 0.389 mmol). The mixture was stirred at RT for 4 h, and then washed with saturated NaHCO$_3$, water, and brine. The organic layer was dried over Na$_2$SO$_4$. Chromatography on silica gel (20% EtOAc/hexanes to 40% EtOAc/hexanes containing 5% TEA) yielded 0.213 g (60%) of Compound S2. $^1$H NMR (CD$_3$CN, 400 MHz): δ 7.82 (d, 1H, J=7.6 Hz), 7.42 (m, 4H), 7.24 (m, 7H), 6.82 (m, 5H), 6.36 (s, 2H), 3.93 (m, 1H), 3.87 (m, 1H), 3.72 (s, 6H), 3.65 (m, 4H), 3.45 (m, 1H), 3.40 (m, 1H), 3.34 (m, 1H), 3.27 (m, 1H), 3.19 (m, 1H), 3.13 (m, 1H), 3.06 (m, 10H), 2.92 (m, 1H), 2.82 (m, 4H), 2.60 (m, 1H), 2.48 (m, 2H), 2.41 (m, 2H), 1.96 (m, 4H), 1.77 (m, 4H), 1.19 (m, 12H). 31P NMR (CD$_3$CN, 160 MHz): δ 147.5.

Example 3. Synthesis of Sulforhodamine Dye S3

This example describes synthesis of an exemplary sulforhodamine dye S3 which comprises an NHS ester. This dye is suitable for fluorescent labeling of biomolecules, for example, peptides, via conjugation reaction with an amino group.

Compound S3 was prepared according to the procedure outlined in Scheme 3.

and the intermediate was re-dissolved in anhydrous DCM (100 mL). The solution was cooled to 0° C. under argon. DIEA (18.5 mL, 106 mmol) was added, followed by methyl-6-aminocaproate-HCl (4.83 g, 26.6 mmol). The reaction mixture was allowed to warm to RT and stirred for 2 h, then washed with water (3×) and brine. The organic layer was dried over Na$_2$SO$_4$. The product was purified by chromatography on silica gel using 40% EtOAc/hexanes with 10% TEA. The product in the cyclized form which forms under basic conditions is colorless; TLC spots slowly turn pink as TEA evaporates. Purification yielded 1.30 g (37%) of Compound 6 as a light blue foam. $^1$H NMR (CDCl$_3$, 400 MHz): δ 7.87 (d, 1H, J=6.8 Hz), 7.46 (m, 2H), 7.00 (m, 1H), 6.44 (s, 2H), 3.66 (s, 3H), 3.16 (m, 8H), 2.91 (m, 6H), 2.58 (s, 4H), 2.14 (m, 2H), 2.07 (m, 4H), 1.89 (m, 4H), 1.39 (m, 4H), 1.15 (m, 2H). LCMS: m/z 654.3 [M+H].

Compound 7

Compound 6 (1.30 g, 1.99 mmol) was dissolved in acetonitrile (60 mL), water (15 mL), and 4.5 mL of concentrated HCl. The solution was heated at 80° C. for 18 h, and then diluted with DCM, washed with saturated NaHCO$_3$, water, and brine. The organic layer was dried over Na$_2$SO$_4$ to yield 1.21 g of crude Compound 7 that was used in the next step without further purification. LCMS: m/z 640.3 [M+H].

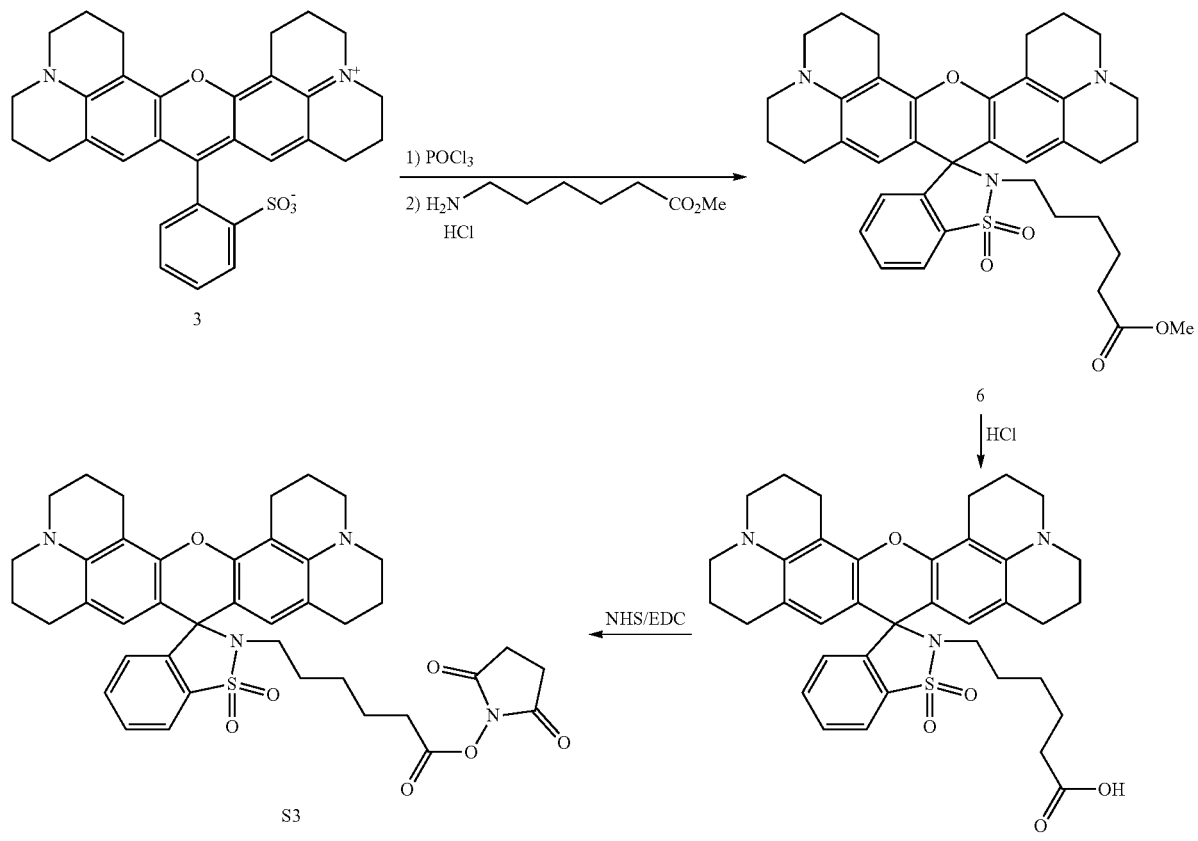

Scheme 3

Compound 6

Compound 3 (2.87 g, 5.28 mmol) was dissolved in 50 mL of anhydrous DCM under argon, and POCl$_3$ (2.5 mL, 26.8 mmol) was added. The resulting mixture was stirred at RT overnight. DCM and POCl$_3$ were removed under vacuum, Compound S3

Compound 7 (1.21 g, 1.89 mmol) was dissolved in 25 ml of anhydrous dimethylformamide (DMF) under argon. N-hydroxysuccinimide (435 mg, 3.78 mmol) and N-(dimethylaminopropyl)-N'-ethylcarbodiimide (EDC) (725 mg, 3.78 mmol) were added. The mixture was stirred at RT overnight, and then DMF was removed under vacuum. The residue was dissolved in DCM, and the solution was washed with 1 N HCl, water, and brine. The organic layer was dried over Na$_2$SO$_4$. Chromatography on silica gel with 5% HOAc and 1% MeOH to 5% MeOH in DCM yielded 880 mg (63%) of Compound S3. $^1$H NMR (DMSO-d$_6$, 400 MHz): δ 7.92 (m, 1H), 7.58 (m, 2H), 6.95 (m, 1H), 6.24 (s, 2H), 3.11 (m, 8H), 2.84 (m, 6H), 2.82 (s, 4H), 2.46 (m, 4H), 1.94 (m, 6H), 1.79 (m, 4H), 1.21 (m, 4H), 1.12 (m, 2H). LCMS: m/z 737.3 [M+H].

Example 4: Synthesis of Sulforhodamine Dye S4

Another exemplary dye S4 comprising an activated ester derivative can be readily prepared according to the procedure outlined in Scheme 4 using the reaction conditions described above for Compound S3.

hexanoate hydrochloride (6.5 g, 0.0360 mole) was added portionwise over 10 min After 1 h, the ice bath was removed, and the reaction mixture was allowed to stir to room temperature over 16 h. The reaction mixture was diluted with DCM (125 mL) and was washed with 1N HCl (2×90 mL) and brine (1×120 mL) and then dried over sodium sulfate. Filtration, concentration and silica gel column purification (ethyl acetate/heptane/TEA, 30:10:60) afforded the product (2.4 g, ~49% yield) as a gold-colored solid. LCMS: m/z 688.5 [M+H] $^1$H NMR (CDCl3, 400 MHz): δ7.83 (d, 1H, J=1.6 Hz), 7.4 (dd, 1H, J=8.4, 2.0 Hz), 6.95 (d, 1H, J=8.4 Hz), 6.42 (s, 2H), 3.65 (s, 3H), 3.16 (m, 8H), 2.89 (m, 6H), 2.58 (m, 4H), 2.14 (t, 2H, J=8 Hz), 2.06 (m, 4H), 1.91 (m, 4H), 1.40 (m, 4H), 1.15 (m, 2H).

Compound S4

Compound 8 (0.60 g, 0.00087 mole) was suspended in acetonitrile (30 mL) with stirring. DI (deionized) water (7 mL) was added and the suspension was stirred for few

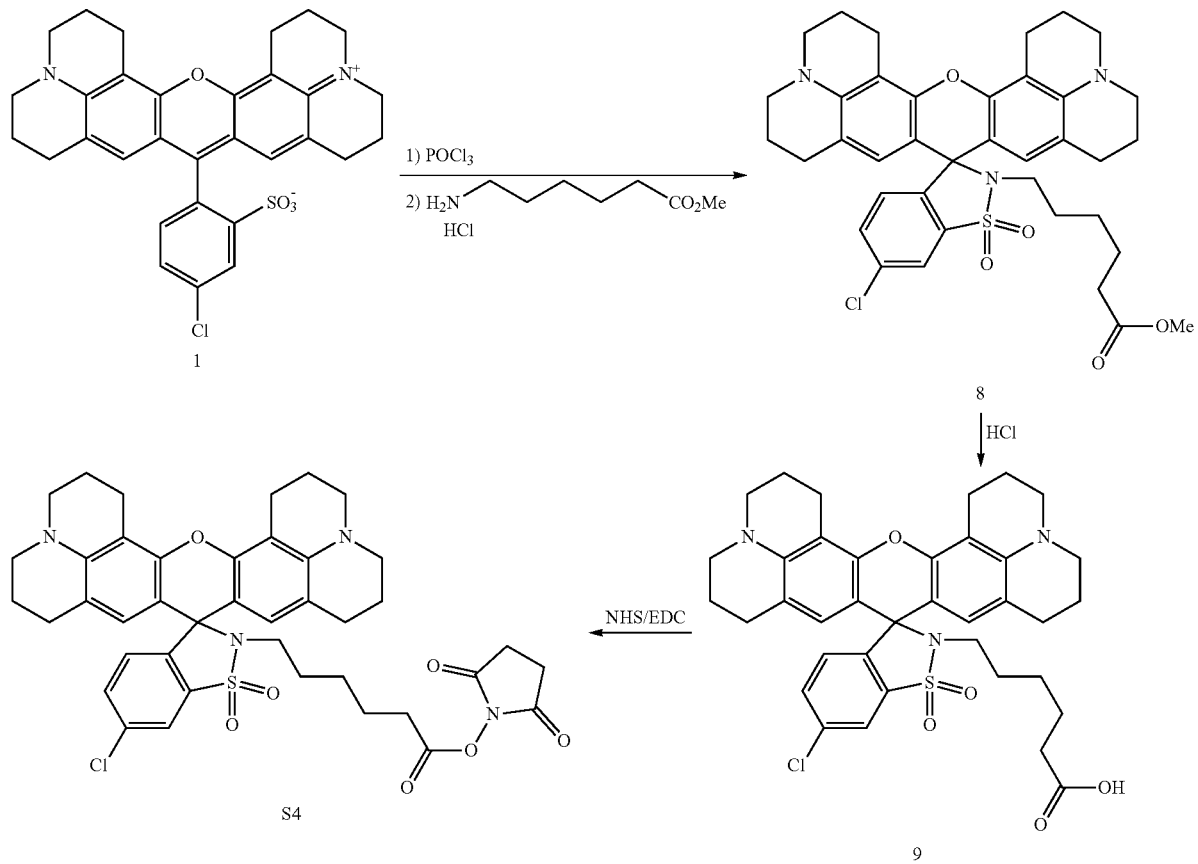

Scheme 4

Compound 8

Compound 1 (4.0 g, 0.0071 mole) was dissolved in anhydrous DCM (60 mL) under argon atmosphere. Neat phosphorous oxychloride (6.5 mL, 0.071 mole) was added in one portion, and the reaction was stirred at room temperature for 23 h. The solvents were removed on a rotary evaporator and the resultant foam was dried at 5 mbar for 2 h. To the foam, anhydrous DCM (75 mL) was added under argon atmosphere and the reaction flask was placed in an ice/water bath. N,N-Diisopropylethylamine (18.5 mL, 0.107 mole) was slowly added at 0-5° C. Solid methyl 6-aminominutes. Concentrated hydrochloric acid (3 mL) was added dropwise which produced red/purple solution. The solution was heated at gentle reflux for 2-3 h then was allowed to stir to room temperature over 15 h. The reaction mixture volume (purple in color) was halved by evaporation on the rotary evaporator and the product was precipitated by pouring the reaction solution into DI water (75 mL) at room temperature. The suspension was filtered, the cake was washed with additional DI water (15 mL) and was dried in a vacuum oven at 40-50° C. and <2 mbar vacuum for 20 h to give 0.54 g (93% yield) of Compound 9 as a purple powder which was used as is in the next step.

Compound 9 obtained above (0.2 g, 0.000296 mole) was placed into a 10 mL round bottom flask and was dissolved in anhydrous DMF (3.0 mL) under argon atmosphere. To the resulting purple solution, N-hydroxysuccinimide (0.04 g. 0.00034 mole, 1.15 eqv) and EDC (0.075 g, 0.00039 mole, 1.3 eq) were added, and the reaction was stirred at ambient temperature for 21 h. The reaction mixture was diluted with DCM (40 mL) and washed with water (20 mL) and dried over $Na_2SO_4$. The solvent was evaporated and the residue was purified by column chromatography using 5-15% MeOH/DCM to afford 0.14 g (61% yield) of Compound S4. LCMS: m/z 771.6 [M+H] $^1$H NMR (DMSO-d6, 400 MHz): δ 8.17 (d, 1H, J=2.0 Hz), 7.60 (dd, 1H, J=8.4, 2.0 Hz), 6.98 (d, 1H, J=8.4 Hz), 6.24 (s, 2H), 3.13 (m, 8H), 2.82 (m, 6H), 2.74 (m, 2H), 2.55 (m, 4H), 2.41 (t, 2H, J=7.8 Hz), 1.94 (m, 4H), 1.79 (m, 4H), 1.10-1.35 (m, 8H)

Example 5: Synthesis of Sulforhodamine Dye S5

This example describes synthesis of an exemplary sulforhodamine dye S5 which comprises a phosphoramidite group. This dye is suitable for incorporation at the 5'-end of an oligonucleotide via standard automated oligonucleotide synthesis.

Compound S5 was prepared according to the procedure outlined in Scheme 5.

Compound 10

Water (27 mL) was cooled to 0° C., and 41 mL of conc. $H_2O_4$ was slowly added. The solution was heated to 160° C. Thoroughly premixed 2-formylbenzenesulfonic acid (5.03 g, 24.2 mmol) and 3-(dimethylamino)phenol (6.63 g, 48.3 mmol) was added portionwise over 1 minute to the sulfuric acid solution. The solution was stirred at 160° C. for 8 hr under air, then cooled to RT and stirred for another 8 h. Cold water (300 mL, ca. 0° C.) was mixed with 100 mL of 10 M NaOH. The crude reaction mixture was added dropwise to the NaOH solution, keeping the temperature below 25° C. Once the reaction mixture was added, more 10 M NaOH was added until pH was about 8.5. The mixture was stirred at RT overnight. The solids were collected by vacuum filtration and dried under high vacuum over KOH to yield 10.6 g of crude material that contained approximately 50% inorganic salts. A 3.57 g portion of the crude material was chromatographed on a silica gel column (2"×7") using a MeOH/DCM solvent gradient (4% to 10% MeOH). A mixture of isomers was produced, with the desired isomer eluting first. 780 mg (22%) of Compound 10 was obtained. LCMS: m/z 423.4 [M+H].

Compound 11

To Compound 10 (740 mg, 1.75 mmol) in 75 mL of anhydrous DCM under argon $POCl_3$ (1.64 mL, 6.50 mmol) was added, and the mixture was stirred at RT for 18 h. DCM was removed under reduced pressure at RT, and then the excess $POCl_3$ was removed under reduced pressure at 60° C.

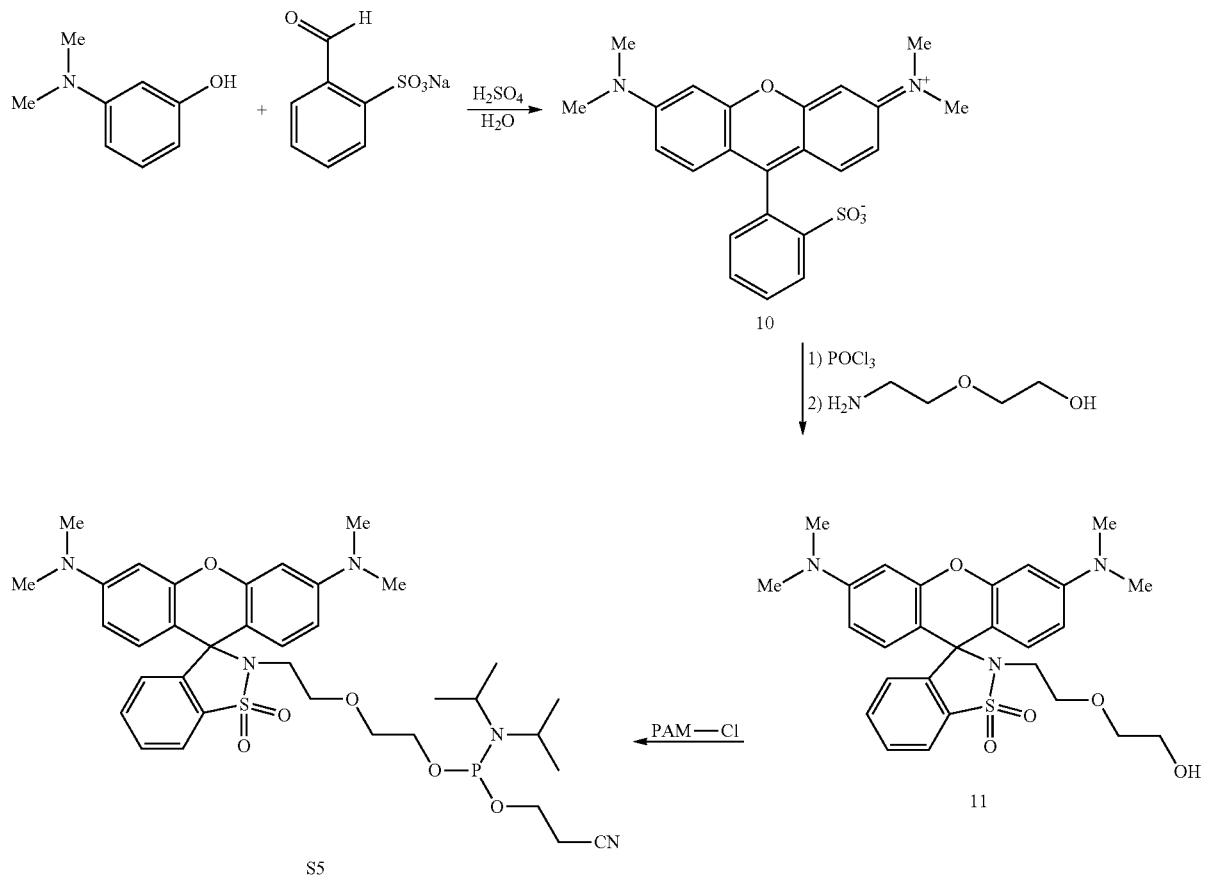

Scheme 5 to yield a foam. The foam was dissolved in 125 mL of anhydrous DCM under argon, and the solution was cooled to 0° C. Triethylamine (3.10 mL, 17.8 mmol) and 2-(2-aminoethoxy)ethanol (0.875 mL, 8.78 mmol) were added. The mixture was allowed to warm up to RT and stirred for 1 h, then washed with water and brine. The organic layer was dried over $Na_2SO_4$. Chromatography on silica gel (1"×7"), 40% EtOAc/hexanes to 60% EtOAc/hexanes containing 10% TEA, yielded 438 mg (49%) of Compound 11. $^1$H NMR (DMSO-$d_6$, 400 MHz): δ 8.00 (m, 1H), 7.61 (m, 2H), 6.96 (m, 1H), 6.71 (s, 1H), 6.69 (s, 1H), 6.53 (m, 2H), 6.43 (d, J=2.5 Hz, 2H), 4.44 (t, J=5.6 Hz, 1H), 3.31 (m, 2H), 3.14 (m, 4H), 2.93 (s, 12H), 2.91 (m, 2H). LCMS: m/z 510.4 [M+H].

Compound S5

Compound 11 (423 mg, 0.830 mmol) was dissolved in 25 mL of anhydrous DCM under argon, and DIEA (0.725 mL, 4.16 mmol) was added followed by PAM-Cl (0.190 mL, 0.924 mmol). The mixture was stirred at RT for 3 h, washed with saturated $NaHCO_3$, water, and brine, and the organic layer was dried over $Na_2SO_4$. Chromatography on silica gel, 20% EtOAc/hexanes to 40% EtOAc/hexanes containing 10% TEA yielded 485 mg (82%) of Compound S5. $^1$H NMR ($CD_3CN$, 400 MHz): δ 7.89 (m, 1H), 7.57 (m, 2H), 6.97 (m, 1H), 6.80 (s, 1H), 6.78 (s, 1H), 6.52 (m, 2H), 6.44 (m, 2H), 3.73 (m, 2H), 3.56 (m, 4H), 3.26 (m, 4H), 2.97 (s, 12H), 2.61 (m, 2H), 1.97 (m, 2H), 1.19 (d, J=6.8 Hz, 6H), 1.12 (d, J=6.8 Hz, 6H) $^{31}$P NMR ($CD_3CN$, 160 MHz): δ 148.1.

Example 6: Synthesis of Sulforhodamine Dye S6

This example describes synthesis of an exemplary sulforhodamine dye S6 which comprises a phosphoramidite group and a hydroxyl group protected with dimethoxytrityl group. This dye is suitable for incorporation at the 5'-end or in a middle position of an oligonucleotide via standard automated oligonucleotide synthesis.

Compound S6 was prepared according to the procedure of Scheme 6.

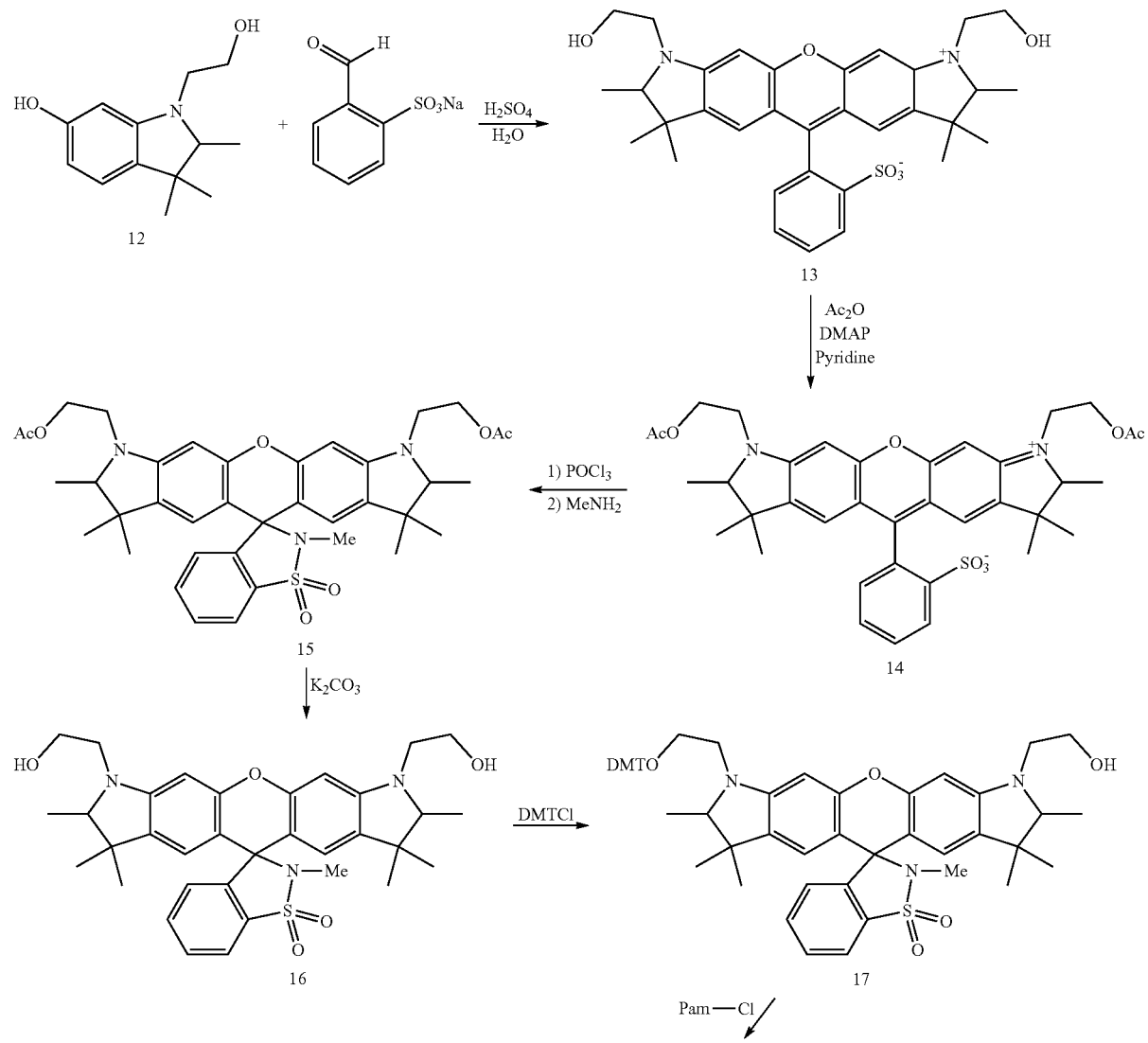

Scheme 6

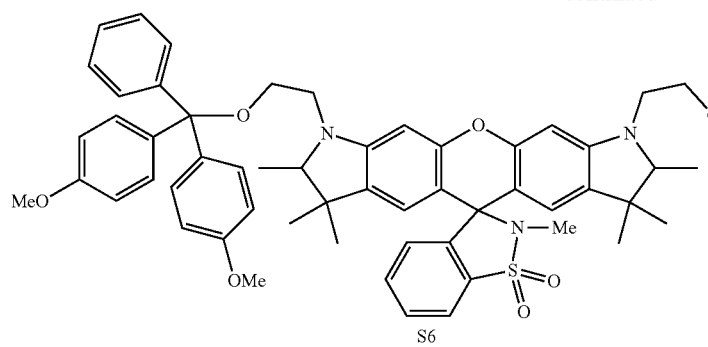

S6

Compound 13

Synthesis of Compound 12 was performed by treatment with ethylene oxide 2,3,3-trimethyl-2,3-dihydro-1H-indol-6-ol in acetic acid (FCH Group, Latvia). Water (27 mL) was cooled to ca 0° C., and conc. $H_2SO_4$ (41 mL) was slowly added. The resulting solution was heated in a 250 mL, 3-neck, round bottom flask to 160° C. Thoroughly premixed 2-formylbenzenesulfonic acid (3.21 g, 15.4 mmol) and Compound 12 (6.82 g, 30.8 mmol) were added portion wise over 1 minute to the sulfuric acid solution. The solution was heated at 160° C. for 6 h open to the air, then cooled to RT and slowly added to 300 mL of cold 5 M NaOH. The pH was adjusted to 9 with $H_2SO_4$. The mixture was extracted with DCM (2×). The combined organic layers were washed with brine and dried over $Na_2SO_4$. The solvent was removed under vacuum, and the crude solids were dried under high vacuum over KOH to yield 2.25 g of crude material. Chromatography on a silica gel column (2"×6") using a ACN/water solvent system (5 to 8% $H_2O$) yielded 526 mg (6%) of Compound 13. $^1H$ NMR (DMSO-$d_6$, 400 MHz): 45€8.03 (d, J=7.5 Hz, 1H), 7.64 (t, J=7.4 Hz, 1H), 7.56 (t, J=7.4 Hz, 1H), 7.15 (m, 1H), 6.82 (s, 2H), 6.64 (s, 2H), 5.01 (s, 2H), 3.76 (m, 8H), 3.48 (m, 2H), 1.11 (m, 18H). LCMS: m/z 591.5 [M+H].

Compound 14

Compound 13 (525 mg, 0.889 mmol) was dissolved in 15 mL of anhydrous pyridine under argon. Acetic anhydride (0.210 mL, 2.22 mmol) and DMAP (11 mg, 0.090 mmol) were added, and the mixture was stirred at RT for 3 h. Pyridine was removed under vacuum, and the residue was purified by chromatography on silica gel (1"×7") using a MeOH/DCM solvent system (2 to 10%) to yield 531 mg (89%) of Compound 14. $^1H$ NMR (DMSO-$d_6$, 400 MHz): δ 8.03 (d, J=7.8 Hz, 1H), 7.66 (t, J=7.4 Hz, 1H), 7.56 (t, J=7.4 Hz, 1H), 7.18 (m, 1H), 6.94 (s, 2H), 6.69 (s, 2H), 4.31 (m, 4H), 3.96 (m, 2H), 3.78 (m, 2H), 3.71 (m, 2H), 1.99 (s, 3H), 1.97 (s, 3H), 1.18 (m, 12H), 0.98 (s, 6H). LCMS: m/z 675.5 [M+H].

Compound 15

Compound 14 (520 mg, 0.771 mmol) was dissolved in 25 mL of anhydrous DCM under argon, and $POCl_3$ (0.360 mL, 3.68 mmol) was added. The reaction mixture was stirred at RT for 5 h, then 2.0 M methylamine in THF (11.6 mL, 23.1 mmol) was added, and the mixture was stirred for 1 h. The mixture was washed with water, saturated $NaHCO_3$, and brine, and the organic layer was dried over $Na_2SO_4$. Chromatography on silica gel (1"×7"), 10% EtOAc/hexanes to 30% EtOAc/hexanes containing 10% TEA yielded 437 mg (82%) of Compound 15. $^1H$ NMR (DMSO-$d_6$, 400 MHz): δ 8.01 (m, 1H), 7.61 (m, 2H), 7.02 (m, 1H), 6.43 (m, 2H), 6.33 (m, 2H), 4.18 (m, 4H), 3.47 (m, 2H), 3.29 (m, 4H), 2.27 (s, 3H), 1.98 (m, 6H), 1.09 (m, 9H), 0.97 (s, 3H), 0.84 (s, 3H), 0.71 (s, 3H). LCMS: m/z 688.5 [M+H].

Compound 16

Compound 15 was dissolved in 20 mL of MeOH, and a solution of $K_2CO_3$ in 5 mL of water was added. The mixture was stirred at RT for 1 h. MeOH was removed under vacuum, the residue was washed with water and brine and dried over $Na_2CO_3$ and under high vacuum to yield 336 mg (90%) of Compound 16 that was used in the next step without further purification. $^1H$ NMR (DMSO-$d_6$, 400 MHz): δ 7.99 (m, 1H), 7.60 (m, 2H), 7.01 (m, 1H), 6.41 (s, 2H), 6.24 (m, 2H), 4.71 (t, J=4.8 Hz, 2H), 3.54 (m, 4H), 3.28 (m, 4H), 3.16 (m, 2H), 2.27 (s, 3H), 1.08 (m, 9H), 0.97 (s, 3H), 0.85 (s, 3H), 0.71 (3H). LCMS: m/z 604.5 [M+H].

Compound 17

Compound 16 (329 mg, 0.545 mmol) was dried by azeotropic evaporation with 12 mL of anhydrous pyridine (2×). The dried material was dissolved in 12 mL of anhydrous pyridine, and DMTCl (258 mg, 0.761 mmol) was added. The mixture was stirred at RT for 18 h, and the reaction was quenched with methanol (2 mL). Solvents were removed under vacuum. Chromatography on silica gel (1"×7"), 30% EtOAc/hexanes to 40% EtOAc/hexanes containing 10% TEA yielded 232 mg (47%) of Compound 17. $^1H$ NMR (DMSO-$d_6$, 400 MHz): δ 8.01 (m, 1H), 7.62 (m, 2H), 7.52 (m, 1H), 7.35 (m, 2H), 7.22 (m, 7H), 7.05 (m, 1H), 6.81 (m, 4H), 6.43 (m, 1H), 6.36 (m, 1H), 6.29 (m, 1H), 4.72 (m, 1H), 3.68 (m, 6H), 3.57 (m, 3H), 3.25 (m, 7H), 2.25 (m, 3H), 1.09 (m, 9H), 0.97 (m, 3H), 0.86 (m, 3H), 0.73 (m, 3H). LCMS: m/z 906.8 [M−H].

Compound S6

To a solution of compound 17 (227 mg, 0.251 mmol) in 20 mL of anhydrous DCM under argon, DIEA (0.218 mL, 1.25 mmol) was added, followed by PAM-Cl (0.075 mL, 0.365 mmol). The mixture was stirred at RT for 2 h and then washed with $NaHCO_3$, water, and brine. The organic layer was dried over $Na_2SO_4$. Chromatography on silica gel, 20% EtOAc/hexanes to 30% EtOAc/hexanes containing 10% TEA, yielded 212 mg (77%) of Compound S6. $^1H$ NMR ($CD_3CN$, 400 MHz): δ 7.91 (m, 1H), 7.57 (m, 2H), 7.41 (m, 2H), 7.28 (m, 7H), 7.03 (m, 1H), 6.81 (m, 4H), 6.56 (m, 2H), 6.32 (m, 2H), 3.79 (m, 2H), 3.72 (m, 6H), 3.58 (m, 4H), 3.41 (m, 2H), 3.33 (m, 2H), 3.22 (m, 2H), 2.53 (m, 2H), 2.32 (m, 3H), 1.11 (m, 21H), 1.03 (m, 3H), 0.93 (m, 3H), 0.80 (m, 3H). $^{31}P$ NMR ($CD_3CN$, 160 MHz): δ 147.3.

Compound S6 was incorporated into the 5'-end of a model oligonucleotide (SEQ. ID No 1). The excitation and emission spectra of the exemplary oligonucleotide are shown in FIG. 3.

Example 7: Synthesis of Sulforhodamine Dye S7

This example describes synthesis of an exemplary sulforhodamine dye S7 which comprises a phosphoramidite group and a hydroxyl group protected with dimethoxytrityl group. This dye is suitable for incorporation at the 5'-end or in a middle position of an oligonucleotide via standard automated oligonucleotide synthesis.

Compound S7 was prepared according to the procedure of Scheme 7.

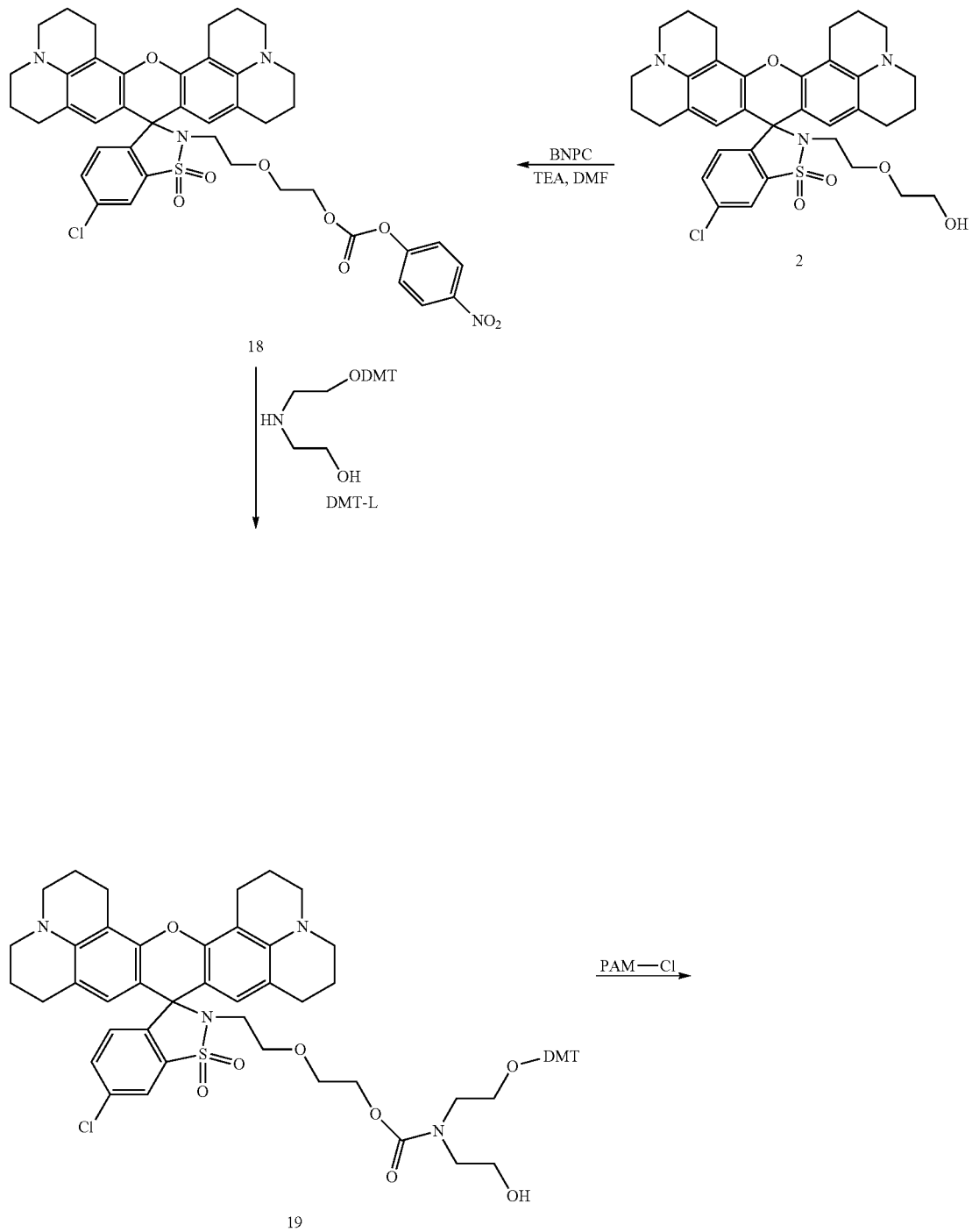

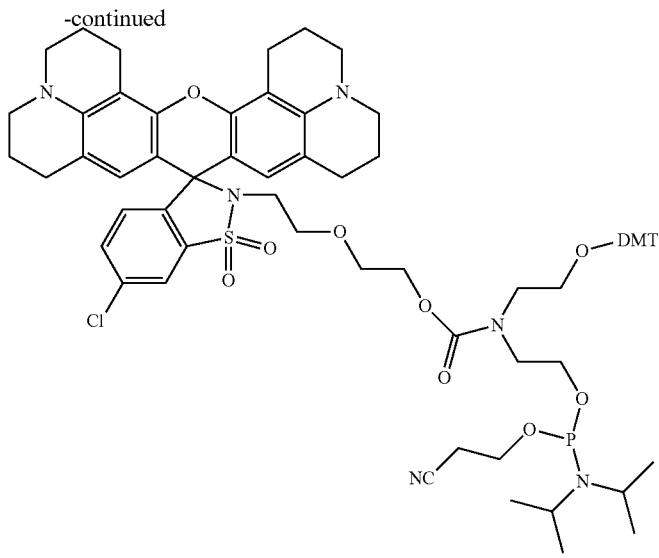

S7

Compound 19

A suspension of Compound 2 (4.9 g, 7.6 mmol) in anhydrous DMF (50 mL) was treated at RT under argon with excess TEA (5.3 mL, 5 eq), followed by bis-nitrophenyl carbonate BNPC (2.8 g, 1.2 eq). The black suspension was heated at 30-35° C. until formation of the intermediate 18 was complete (1.5-3 h after addition of BNPC). Mono-DMT-diethanolamine (DMT-L) (4.6 g, 1.5 eq) was added in one portion, and the reaction mixture was stirred at 30-35° C. (1-3 h) then at RT (>2 h) until the completion of the reaction. The reaction mixture was diluted with EtOAc (530 mL) and was transferred to a separatory funnel. The EtOAc layer was washed with DI water (4×380 mL) and brine (1×380 mL). The EtOAc layer was dried over $Na_2SO_4$, filtered, and evaporated to give crude Compound 19. Silica gel column purification of crude product afforded pure Compound 19 as lavender to purple solid (7.5 g, 91% yield). LCMS: m/z 1082.0 [M+H]. $^1$HNMR (DMSO-d6, 400 MHz): δ 8.18 (d, 1H, J=2 Hz), 7.22 (dd, 1H, J=8.4, 1.6 Hz), 7.16-7.36 (m, 10H), 6.95 (m, 1H), 6.86 (d, 2H, J=8.8 Hz), 6.81 (d, 2H, J=8.8 Hz), 6.28 (s, 2H), 4.60 (m, 1H), 3.90 (m, 1H), 3.80 (m, 1H), 3.70 (m, 6H), 3.40 (m, 3H), 3.30 (m, 3H), 3.16 (m, 2H), 3.07 (m, 12H), 2.90 (m, 1H), 2.80 (m, 1H), 2.78 (m, 4H), 2.44 (m, 4H), 1.92 (m, 4H), 1.75 (m, 4H).

Compound S7

Compound 19 (6.5 g, 6 mmol) was placed in a 3-necked round bottom flask and was dried under high vacuum at ≤2 mBar for ≥90 min. Dried Compound 19 was then dissolved in anhydrous DCM (130 mL) under argon. The reaction flask was cooled to 0-5° C., and DIEA (10.5 mL, 10 eq) was added followed by dropwise addition of N,N-diisopropylchlorophosphoramidite-Cl (PAM-Cl) (1.7 mL, 1.3 eq.) while maintaining the internal temperature at 0-5° C. The reaction was allowed to stir at RT until completion (2-3 h). The reaction was diluted with DCM (130 mL) and washed with $NaHCO_3$ (2×80 mL), brine (150 mL) and dried over $Na_2SO_4$. Filtration, concentration and silica gel column purification of crude product afforded the pure Compound S7 as a pink to lavender solid (6.07 g, 78% yield). LCMS: m/z 1281.2 [M+H]. $^{31}$P NMR (DMSO-d6, 160 MHz): δ 147.57. $^1$H NMR (DMSO-d6, 400 MHz): δ 7.90 (s, 1H), 7.48 (dd, 1H, J=8.4, 2.0 Hz), 7.40 (m, 2H), 7.20-7.30 (m, 7H), 6.82 (m, 5H), 6.35 (s, 2H), 3.93 (m, 1H), 3.87 (m, 1H), 3.76 (m, 8H), 3.62 (m, 4H), 3.46 (m, 2H), 3.41 (m, 1H), 3.33 (m, 1H), 3.25 (m, 1H) 3.19 (m, 1H), 3.13 (m, 11H), 2.98 (m, 1H), 2.84-2.91 (m, 5H), 2.64 (m, 2H), 2.40-2.56 (m, 6H), 1.95 (m, 4H), 1.78 (m, 4H), 1.10-1.23 (m, 12H).

Example 8: Synthesis of Compound S8

This example describes synthesis of an exemplary sulforhodamine dye S8 which comprises a phosphoramidite group and a hydroxyl group protected with dimethoxytrityl group. This dye is suitable for incorporation at the 5'-end or in a middle position of an oligonucleotide via standard automated oligonucleotide synthesis.

Compound S8 was prepared according to the procedure of Scheme 8.

Scheme 8
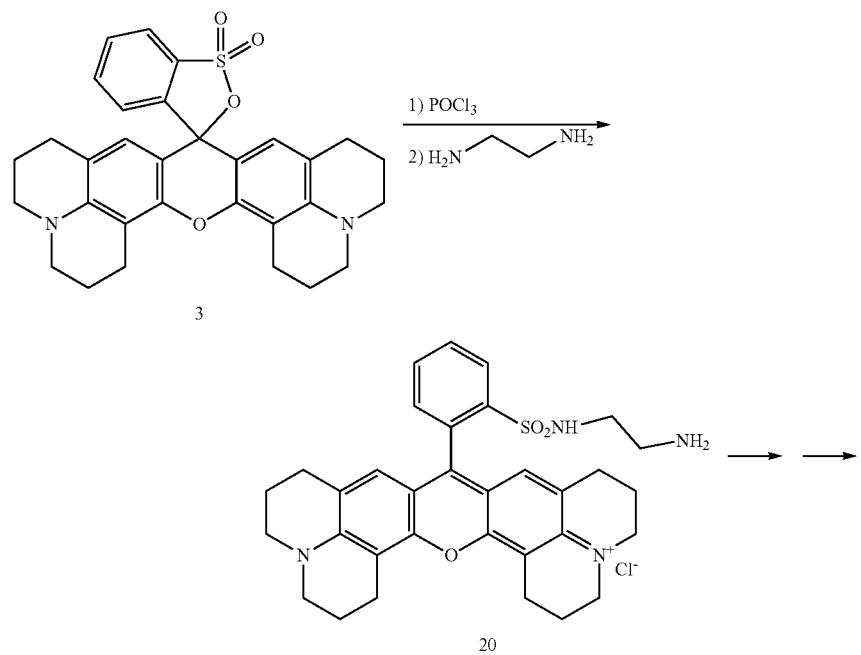
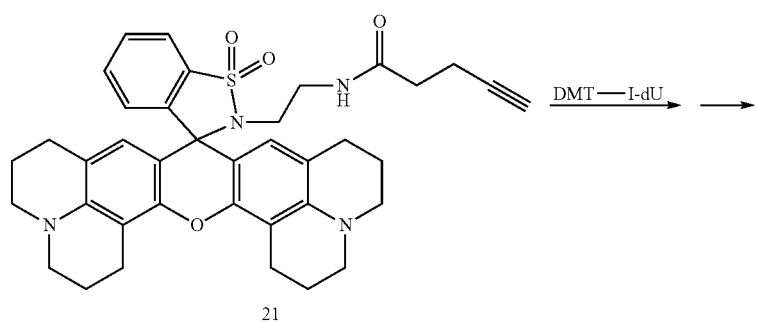
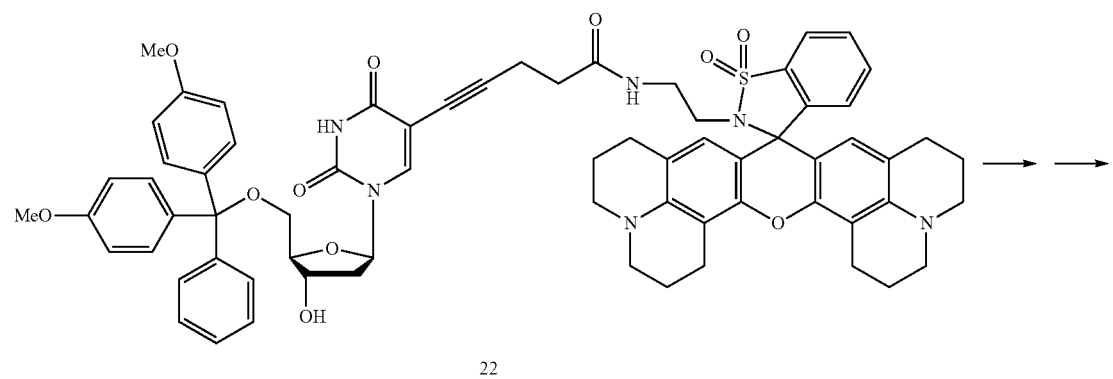

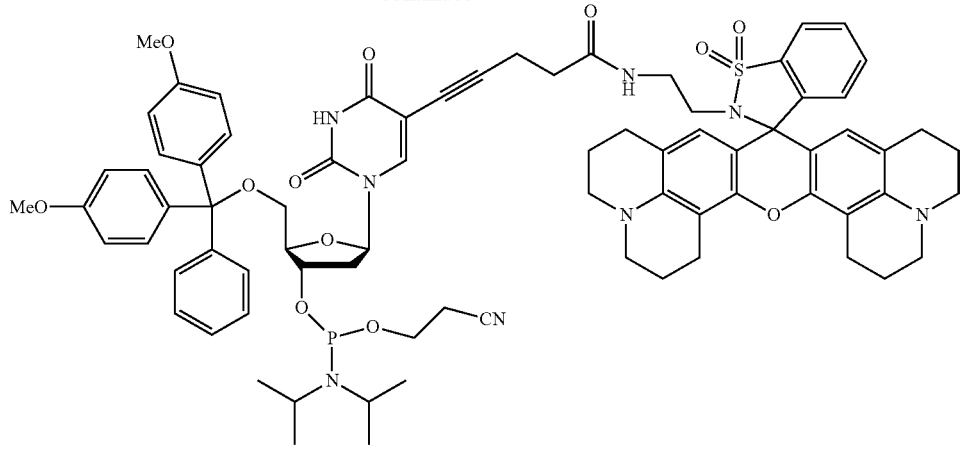

S8

Compound 20

Compound 3 (2.80 g, 1 eq) was dissolved in anhydrous dichloromethane (50 mL) and POCl$_3$ (6.9 mL, 14 eq) was added dropwise at ambient temperature. After 4 hr, the reaction mixture was evaporated to dryness to provide crude intermediate as dark blue solid. Ethylene diamine (EDA, 6.0 mL, 17.0 eq) was dissolved in anhydrous dichloromethane (40 mL), and the solution was cooled to 5° C. The solid was dissolved in anhydrous dichloromethane (20 mL) and added dropwise to the EDA solution. After 17 h at 4° C. the reaction mixture was washed with saturated sodium bicarbonate (2×40 mL) and then with DI water (40 mL). The organic layer was evaporated to dryness to yield Compound 20 (3.08 g, 96%) as dark blue solid. LCMS: m/z 569.4 [M+H$^+$]. Calc-d: 569.25. $^1$H NMR (DMSO-d$_6$, 400 MHz): δ 7.92 (dd, 1H, J=6.0, 2.8 Hz), 7.54-7.56 (m, 2H), 6.90 (dd, 1H, J=6.4, 2.8 Hz), 6.30 (s, 2H), 3.3 (br., 2H), 3.0-3.14 (m, 8H), 2.75-2.88 (m, 6H), 2.35-2.49 (m, 6H), 1.95 (m, 4H), 1.79 (m, 4H).

Compound 21

4-Pentynoic acid (4PA, 0.67 g, 1.1 eq) was dissolved in anhydrous acetonitrile (6.5 mL), and the solution was cooled to 5° C. Diisopropylethylamine (3.3 mL, 3.0 eq) was added followed by pentafluorophenyl trifluoroacetate (PFP-TFA, 1.2 mL, 1.1 eq). The reaction mixture was incubated at ambient temperature for 1 h. Compound 20 (3.1 g, 1.0 eq) was suspended in a mixture of 10 mL N,N-dimethylformamide, 10 mL dichloromethane and 5 mL dimethyl sulfoxide. The suspension was added to the activated 4-pentynoic acid solution and incubated at ambient temperature for 1 h. The reaction mixture was diluted with 50 mL ethyl acetate and washed with saturated sodium bicarbonate (2×30 mL) and then DI water (30 mL). The organic layer was evaporated to dryness. The crude product was purified using silica gel column purification to yield Compound 21 (2.74 g, 68% yield) as blue solid. LCMS: m/z 649.51 [M+H$^+$]. Calc-d: 649.28. $^1$H NMR (DMSO-d$_6$, 400 MHz): δ 7.93-7.96 (m, 1H), 7.65 (t, 1H, J=5.6 Hz), 7.54-7.58 (m, 2H), 6.87-6.90 (m, 1H), 6.32 (s, 2H), 3.05-3.16 (m, 8H), 2.97-3.04 (m, 2H), 2.79-2.88 (m, 6H), 2.72 (t, 1H, J=2.4 Hz), 2.39-2.58 (m, 4H, overlaps with DMSO-d5), 2.20-2.27 (m, 2H), 2.10 (t, 2H, 7.6 Hz), 1.95 (m, 4H), 1.79 (m, 4H).

Compound 22

Compound 21 (2.7 g, 1.0 eq) was dissolved in N,N-dimethylformamide (22.0 mL) and triethylamine (1.7 mL, 3.0 eq) was added. The prepared solution was added under inert atmosphere to the solid mixture of 5-iodo-5'-dimethoxytrityl-2'-deoxyuridine (2.7 g, 1.0 eq; DMT-I-dU), tetrakis(triphenylphosphine)palladium(0) (0.48 g, 0.1 eq) and copper(I) iodide (0.24 g, 0.3 eq), and the reaction mixture was incubated at ambient temperature for 2 h. The reaction mixture was diluted with ethyl acetate (120 mL) and washed with 0.1 M EDTA solution (2×80 mL). The organic layer was dried with anhydrous sodium sulfate (25 g, 18 h), filtered and evaporated to dryness (blue solid). The crude product was purified using silica gel column purification to yield Compound 22 (4.73 g, 97% yield) as blue solid. LCMS: m/z 1177.9 [M+H$^+$]. Calc-d: 1177.47 $^1$H NMR (DMSO-d$_6$, 400 MHz): δ 7.93-7.96 (m, 1H), 7.83 (s, 1H), 7.54-7.58 (m, 2H), 7.49 (t, 1H, J=6.0 Hz), 7.37-7.41 (m, 2H), 7.25-7.31 (m, 6H), 7.18-7.22 (m, 1H), 6.83-6.90 (m, 5H), 6.32 (s, 2H), 6.11 (t, 1H, J=6.8 Hz), 5.33 (s, 1H), 4.27 (m, 1H), 3.91 (m, 1H), 3.71 (s, 6H), 3.21-3.26 (m, 2H), 3.05-3.14 (m, 8H), 2.97-3.04 (m, 2H), 2.77-2.88 (m, 6H), 2.38-2.59 (m, 4H, overlaps with DMSO-d5), 2.14-2.28 (m, 4H), 1.98-2.03 (m, 2H), 1.93 (m, 4H), 1.77 (m, 4H).

Compound S8

Compound 22 (4.6 g, 1.0 eq) was dissolved in anhydrous dichloromethane (27.6 mL) under argon. The reaction flask was cooled to 0-5° C. and diisopropylethylamine (2.0 mL, 3.0 eq) was added followed by dropwise addition of PAM-Cl (1.1 mL, 1.3 eq) while maintaining the internal temperature at 0-5° C. The reaction was allowed to stir at RT for 2 h. The reaction was diluted with ethyl acetate (150 mL), washed with NaHCO$_3$ (2×100 mL), brine (80 mL), dried over anhydrous sodium sulfate (46 g, 20 h), filtered and evaporated to dryness (blue solid). The product was dissolved in 200 mL dichloromethane and purified by precipitation in equal mixture of ether and hexanes (2 L). Filtration and drying afforded the product as a blue solid (1.92 g, 36% yield). LCMS: m/z 1378.3 [M+H$^+$]. $^{31}$P NMR (CD3CN, 160 MHz): two singlets (diastereomers) δ 147.97 ppm and 148.04 ppm. $^1$H NMR (CD3CN, 400 MHz): δ 9.2 (br, 1H), 7.94 and 7.97 (s, 1H), 7.85-7.89 (m, 1H), 7.53-7.59 (m, 2H), 7.42-7.47 (m, 2H), 7.30-7.37 (m, 4H), 7.19-7.29 (m, 3H), 6.80-6.92 (m, 5H), 6.35 (s, 2H), 6.13-6.21 (m, 1H), 5.36-5.41 (m, 1H), 4.55-4.64 (m, 1H), 4.08-4.15 (m, 1H), 3.73-3.75 (m, 6H), 3.55-3.70 (m, 4H), 3.25-3.40 (m, 2H), 3.05-3.16 (m, 8H), 2.93-3.00 (m, 2H), 2.72-2.88 (m, 6H), 2.66 (t, 1H, 6.0 Hz), 2.33-2.59 (m, 7H), 2.15-2.22 (m, 2H), 1.92-2.00 (m, 2H), 1.75-1.88 (m, 6H), 1.14-1.21 (m, 9H), 1.07 and 1.06 (2×s, 3H).

Example 9: Synthesis of Compound S9

This example describes synthesis of an exemplary sulforhodamine dye S9 which comprises a phosphoramidite group and a hydroxyl group protected with dimethoxytrityl group. This dye is suitable for incorporation at the 5'-end or in a middle position of an oligonucleotide via standard automated oligonucleotide synthesis.

Compound S9 is prepared analogously to the preparation of Compound S8 described above according to Scheme 9.

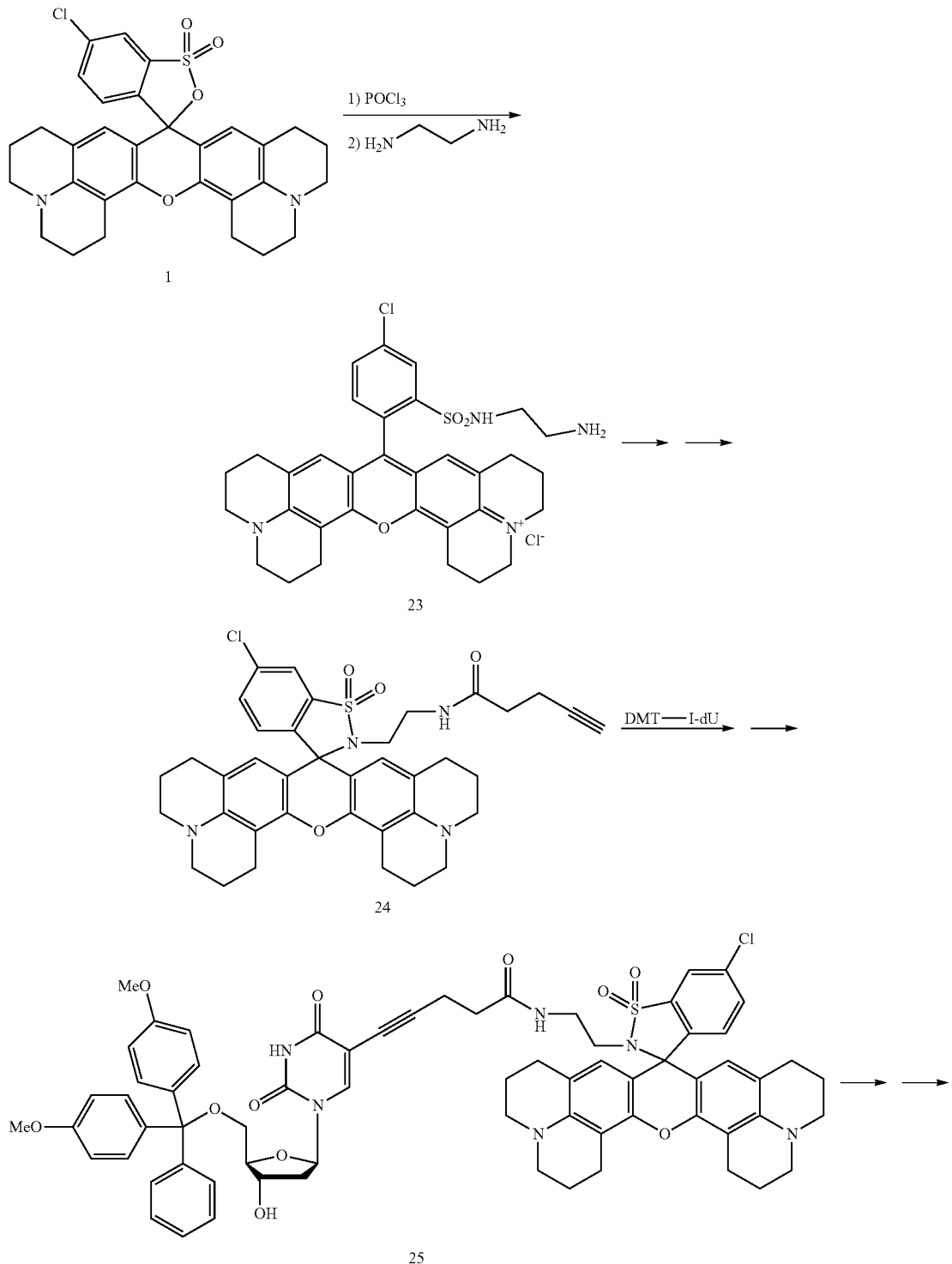

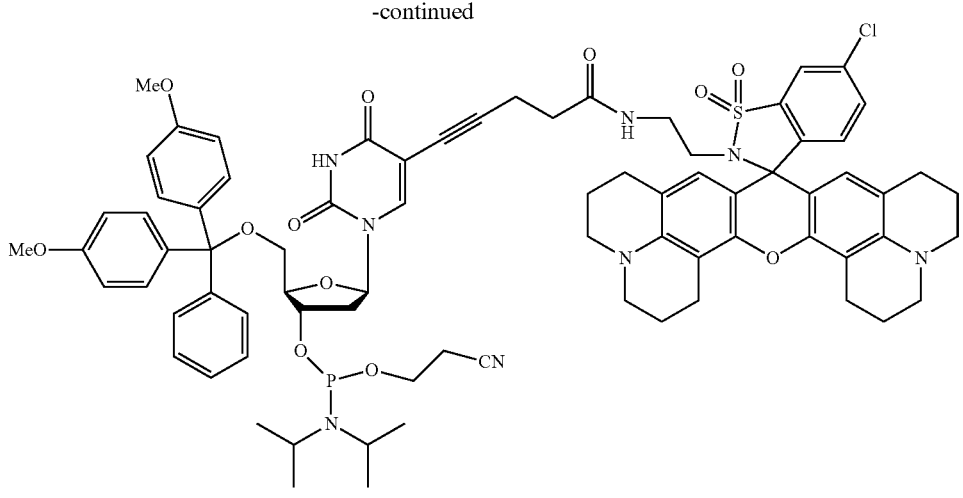

S9

Example 10: Preparation of Fluorescently Labeled Polynucleotides from Sulforhodamine Dye Phosphoramidites Polynucleotides comprising sulforhodamine dyes were synthesized on a MerMade-12 oligonucleotide synthesizer utilizing standard 200 nmol DNA protocol in cycles of DMT removal-coupling-capping-oxidation-capping. Coupling time for sulforhodamine dye phosphoramidites was extended to 6 min.

For polynucleotides containing 5' sulforhodamine dyes, synthesis was completed after the last sulforhodamine dye phosphoramidite coupling cycle. In case of internal incorporation of sulforhodamine dye phosphoramidites, more nucleoside monomers were added after the coupling of the dye. A final DMT group was left on polynucleotide.

Fully assembled polynucleotides were cleaved from solid support and deprotected by 30% ammonium hydroxide at 55° C. for 10-12 h. After the removal of ammonia, oligonucleotides were analyzed and purified by reverse-phase HPLC (RP-HPLC) on C18 Gemini column eluting with a linear gradient of acetonitrile/0.1 M triethylammonium bicarbonate, pH 7. After DMT group removal, polynucleotides were purified for the second time.

Sulforhodamine 101-labeled oligonucleotides were prepared by conjugation of amino-$C_6$-oligo with a commercial Texas Red®-X (NHS ester) reagent (mixed isomers, Thermo Fisher Scientific). All purified polynucleotides were characterized by mass spectroscopy.

5'-Nuclease probes comprising exemplary sulforhodamine dyes were prepared using commercially available BHQ-2 quencher CPG, Glycolate 500 Angstrom column (BioSearch Technologies). A01 denotes 2-amino-dA (2,6-diamino-2'-deoxypurine riboside) which was incorporated using commercially available 2-Amino-dA-CE phosphoramidite (Glen Research, product Catalog Number: 10-1085).

Exemplary oligonucleotides incorporating sulforhodamine dye phosphoramidites and Sulforhodamine 101 (Tx Red)-labeled oligonucleotides are listed in Table 1.

TABLE 1

| Name | 5' Dye | Sequence | 3' Quencher |
|---|---|---|---|
| Oligo A | Tx Red | SEQ ID NO: 1 | N/A |
| Oligo B | (S6) | SEQ ID NO: 1 | N/A |
| Oligo C | (S7) | SEQ ID NO: 1 | N/A |
| Oligo D | Tx Red | SEQ ID NO: 2 | BHQ-2 |
| Oligo E | (S7) | SEQ ID NO: 2 | BHQ-2 |
| Oligo F | Tx Red | SEQ ID NO: 3 | BHQ-2 |
| Oligo G | (S7) | SEQ ID NO: 3 | BHQ-2 |

In Table 1, the dye moieties incorporated at the 5'-end of the polynucleotides have the following structures:

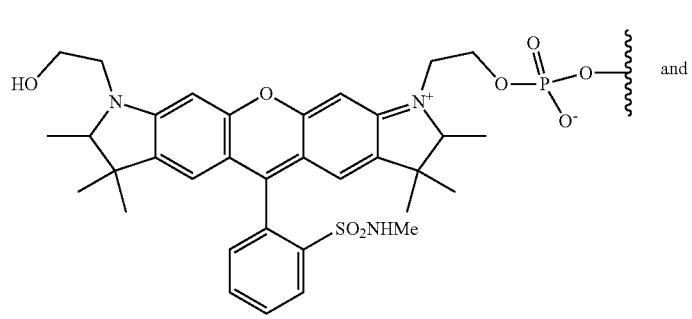

(S6) and

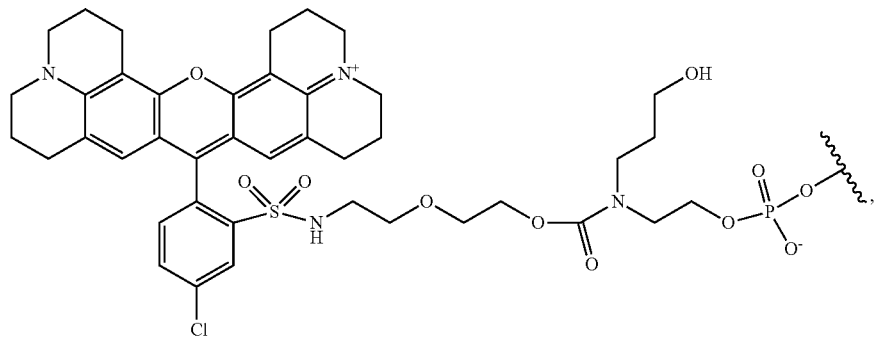

(S7)

and the oligonucleotide sequences are as follows: TCA GAG TAC CTG AAA CA (SEQ ID NO: 1), CC(A01) CGG (A01)GC G(A01)G AC(A01) TCT CGG CC (SEQ ID NO: 2), and CC(A01) G(A01)G CAA ACT GGG CGG C(A01) (SEQ ID NO:3), wherein A01 denotes 2,6-diaminopurine 2'-deoxyriboside.

Figure 1B:
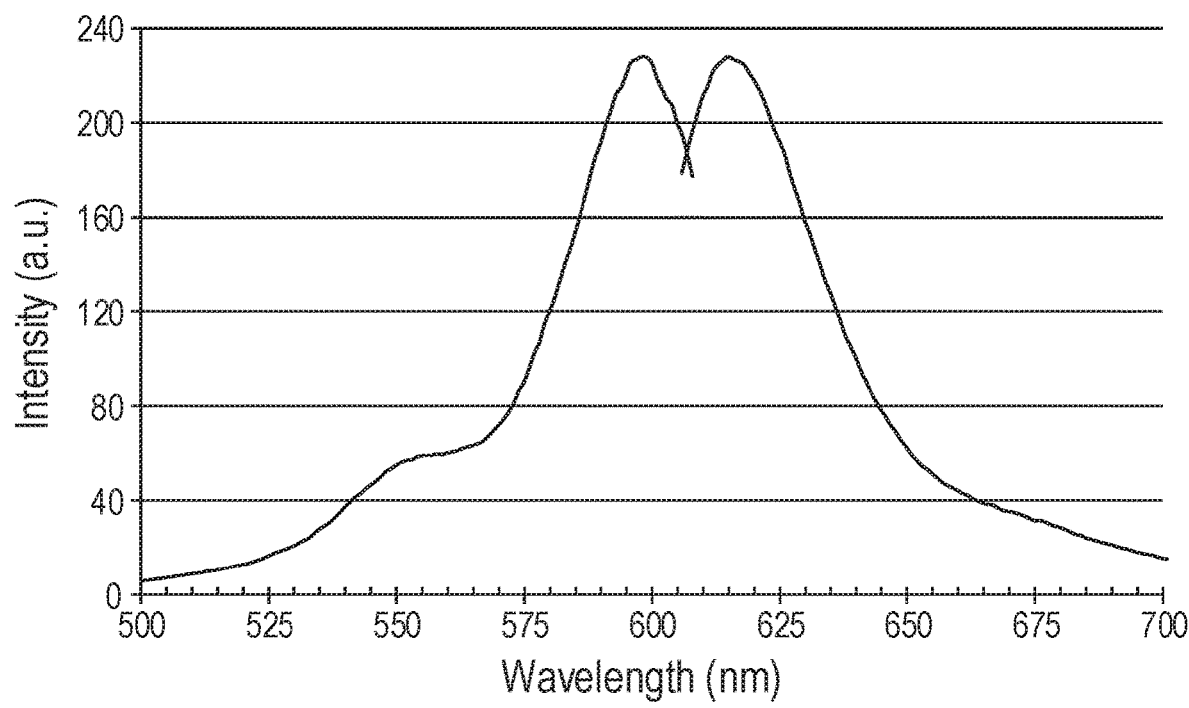
FIG. 1B is the excitation and emission spectra an exemplary polynucleotide SEQ ID NO: 1 labeled with dye S7: (S7)-TCAGAGTACCTGAAACA (Oligo B); Ex/Em=598 nm/616 nm. In this figure, the x-axis is nm, and the y-axis is fluorescence units.
Figure 1C:
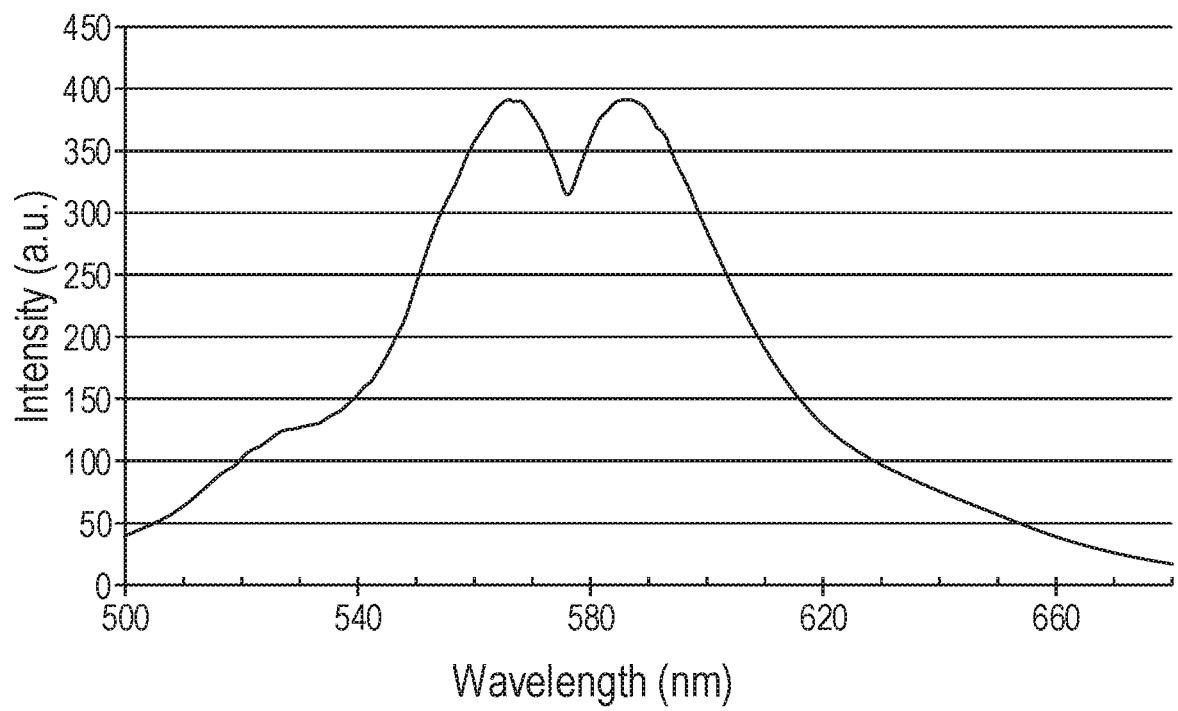
FIG. 1C depicts the excitation and emission spectra an exemplary polynucleotide SEQ ID NO: 1 labeled with sulforhodamine dye S6: (S6)-TCAGAGTACCTGAAACA (Oligo C); Ex/Em max=568/589 nm. In this figure, the x-axis is nm, and the y-axis is fluorescence units.

Excitation and emission spectra of labeled oligonucleotides were recorded on an Agilent Cary fluorimeter (200 nM oligonucleotide, 0.1 M Tris buffer, pH 8). As shown in FIGS. 1A and 1B, the excitation and emission maxima of an exemplary oligonucleotide prepared via automated oligonucleotide synthesis using an exemplary dye phosphoramidite reagent Compound S7 (Oligo C) matches the excitation and emission maxima values of an oligonucleotide comprising Texas Red® dye (Oligo A). As shown in FIG. 1C, the excitation and emission maxima of an exemplary oligonucleotide prepared via automated oligonucleotide synthesis using an exemplary dye phosphoramidite reagent Compound S6 (Oligo B), are close to the literature-reported excitation and emission maxima of TAMRA dye-labeled oligonucleotides.

Example 11: Comparison of Performance of an Exemplary Sulforhodamine Dye and Texas Red® Dye in 5'-Nuclease PCR In this example, 5'-nuclease PCR reactions were performed using cleavable quenched fluorescent probes comprising dyes of the disclosure and a commercially available quencher BHQ-2. The PCR profiles shown in FIGS. 2A and 2B demonstrate that probes comprising dyes of the invention performed efficiently as detection probes.

5'-Nuclease PCR probes comprising dyes of the disclosure were evaluated and compared to Texas Red®-comprising PCR probes. Human genome DNA beta-globulin housekeeping gene was used as the target. The forward and reverse primers had the following sequences:

```
                                   (SEQ. ID NO: 4)
AAA CCT CCA GGC CAG AAA GAG AGA GTA (SEQ. ID NO: 5)
AAA AGG CAT TCC TGA AGC TGA CAG CAT TC (SEQ. ID NO: 6)
AAA ACC TGC CTT CTG CGT GAG ATT CT (SEQ. ID NO: 7)
CTG TAC GAA AAG ACC ACA GGG CCC AT
```

PCR was performed on GeneXpert® (Cepheid) instrument with 4 modules (detection: Tx Red channel, Ex 585 nm, Em 610 nm). Each PCR curve is an average of 4 repeats. The following PCR protocol was used:

Amplicon: length 96 bp, 1,000 copies/reaction;
Nucleotide triphosphate (NTP) concentrations for each of ATP, CTP, GTP, TTP: 0.25 mmol;
Taq polymerase: 3 units/25 uL reaction;
Primer (each) concentrations: 200 nM; and
Probe concentration: 250 nM;
Two cycles of denaturation for 35 sec at 95° C., annealing-extension for 30 sec at 66°; and 45 cycles: denaturation for 8 sec at 95° C., annealing-extension for 30 sec at 66° C.

Figure 2A:
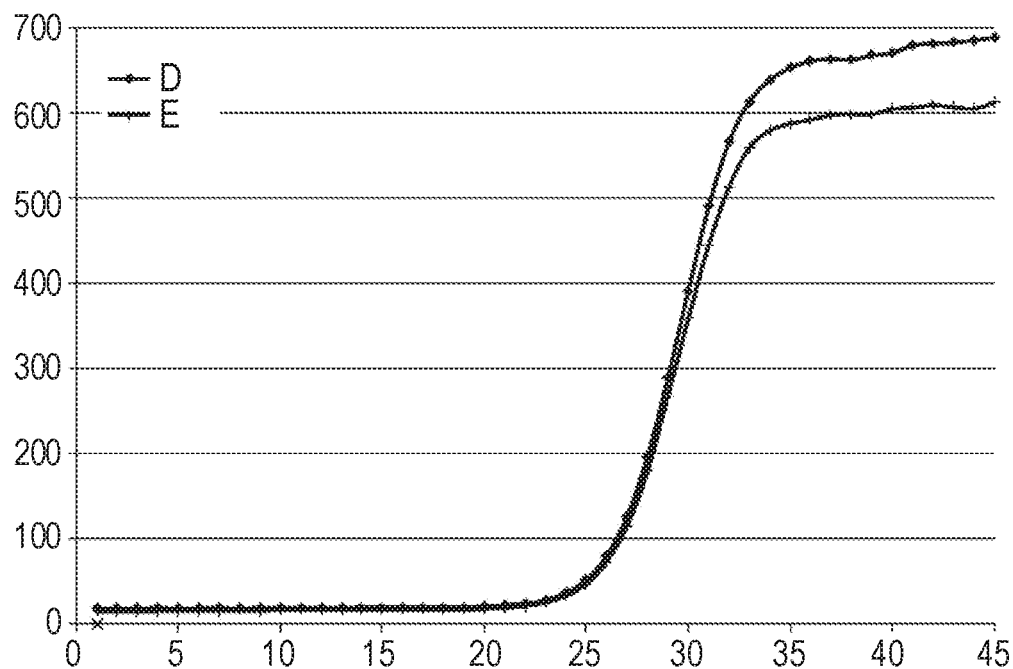
FIG. 2A shows PCR curves comparing performance of probe having SEQ. ID NO: 2 labeled with Texas Red® dye (Oligo D) and probe having SEQ ID NO: 2 labeled with an exemplary dye (Oligo E) in a model PCR reaction using primers SEQ ID NOS: 4 and 5. In this figure, the x-axis is Ct, and the y-axis is fluorescent units.
Figure 2B:
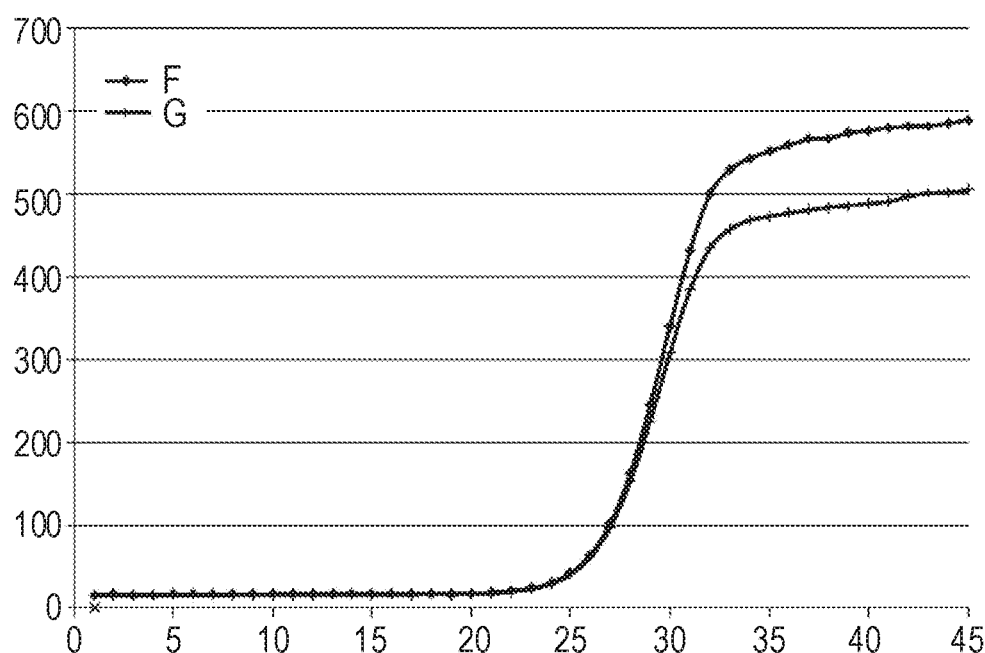
FIG. 2B shows PCR curves comparing performance of Texas Red® dye-labeled probe having SEQ ID NO: 3 labeled with Texas Red® dye (Oligo F) and probe having SEQ. ID NO: 3 labeled with an exemplary dye (Oligo G) in a model PCR reaction using primers SEQ ID NOS: 6 and 7. In this figure, the x-axis is Ct, and the y-axis is fluorescent units.

The resulting PCR data are shown in FIGS. 2A and 2B. As demonstrated by the data, 5' nuclease PCR probes labeled with exemplary dyes of the disclosure have performance comparable with that of with Texas Red®-labeled PCR probes. As can be seen from the data of FIGS. 2A and 2B, probes comprising an exemplary dye S7 demonstrate endpoint similar to those demonstrated by probes labeled with Texas Red®.

Example 12: Synthesis of Compounds S10a and S10b

This example describes synthesis of exemplary sulforhodamine dyes S10a and S10b which comprise a phosphoramidite group. These dyes are suitable for incorporation at the 5'-end position of an oligonucleotide via standard automated oligonucleotide synthesis.

Sulforhodamine dyes, such as compound S10 shown below, prepared from racemic intermediate 12 contain two chiral centers which results in the final dyes existing as a mixture of 4 diastereomers.

S10

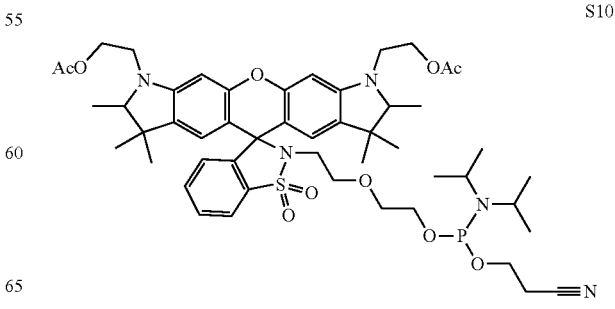

Upon incorporation of such dyes to polynucleotides, e.g., by phosphoramidite synthesis or conjugation, a diastereomeric mixture of fluorescently labeled polynucleotides is produced. Although these polynucleotides have identical optical properties, their purification by HPLC can be difficult due to the polynucleotides eluting as multiple or broad peaks. The use of pure stereoisomers of the dyes can simplify chromatographic purification of such labeled polynucleotides Compound S10a is an example of a sulforhodamine dye synthesized from 12a, a single enantiomer of compound 12, resulting in compound S10a existing as a single diastereomer. Compound 12a can be synthesized from 2,3,3-trimethyl-3H-indole-6-ol (FCH Group, Lativa) via asymmetric transfer hydrogenation (as described in Org. Lett. 2018, 20, 5107-5111) using chiral catalyst RuCl(p-cymene) [(R,R)-Ts-DPEN] (Aldrich cat #703907). Similarly, compound 12b, a stereoisomer of 12a, can be synthesized by a similar procedure using RuCl(p-cymene)) [(S,S)-Ts-DPEN] (Aldrich).

Compound 13a

2-Formylbenzenesulfononic acid sodium salt (1.41 g, 6.77 mmol) and one equivalent of compound 12a (1.50 g, 6.77 mmol) were dissolved in 40 mL of 60% $H_2SO_4$. The solution was heated at 60° C. for 3 h, and another equivalent of compound 12a was added, and the mixture was heated to 100° C. After 72 h, the reaction mixture was cooled to RT, diluted with 40 mL of water, poured into 500 mL of crushed ice, and stirred for 1.5 hours. The resulting solids were collected by filtration. Brine (100 mL) was added to the filtrate, and the filtrate was extracted with dichloromethane (2×). The combined organic layers were dried over $Na_2SO_4$, filtered, and the solvents were removed in vacuo. The material extracted from the organics and the precipitate were combined and purified by chromatography on a silica gel column (2"×7") using a gradient of ACN/water system (4% to 10% $H_2O$) to yield 1.08 g (27%) of Compound 13A. $^1$H NMR (DMSO-$d_6$, 500 MHz): δ 8.03 (d, J=7.8 Hz, 1H), 7.64 (t, J=7.5 Hz, 1H), 7.55 (t, J=7.5 Hz, 1H), 7.15 (d, J=7.5 Hz, 1H), 6.91 (m, 1H), 6.81 (d, J=3.6 Hz, 1H), 6.65 (m, 2H),

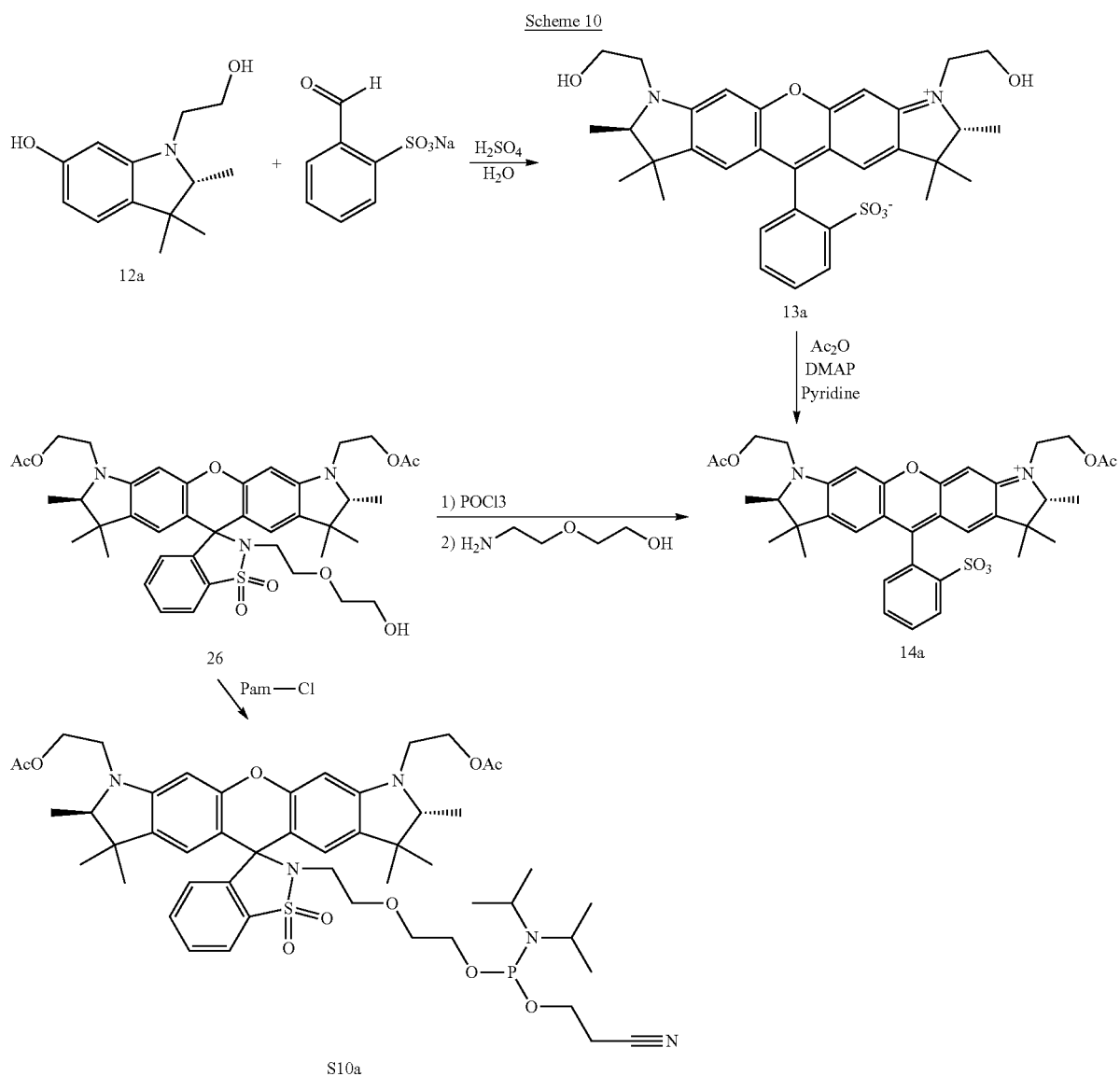

Scheme 10

4.98 (m, 1H), 4.93 (m, 1H), 3.96 (m, 1H), 3.82 (m, 2H), 3.70 (m, 5H), 3.45 (m, 2H), 1.18 (m, 9H), 1.12 (s, 3H), 0.98 (s, 3H), 0.97 (s, 3H). LCMS: m/z 591.5 [M+H].

Compound 14a

Under argon, compound 13a (1.06 g, 1.79 mmol) was dissolved in 25 mL of anhydrous pyridine. Acetic anhydride (0.510 mL, 5.39 mmol) and DMAP (22 mg, 0.180 mmol) were added, and the mixture was stirred at RT for 5 h. Pyridine was removed in vacuo, and the residue was chromatographed on a silica gel column (1.5"×5") using a MeOH/DCM solvent system (4 to 8% MeOH) to yield 475 mg (39%) of compound 14a. $^1$H NMR (DMSO-$d_6$, 500 MHz): δ 8.03 (d, J=7.8 Hz, 1H), 7.65 (t, J=7.4 Hz, 1H), 7.56 (t, J=7.4 Hz, 1H), 7.16 (d, J=7.3 Hz, 1H), 6.93 (d, J=5.3 Hz, 2H), 6.70 (s, 2H), 4.29 (m, 4H), 3.96 (m, 2H), 3.78 (m, 2H), 3.69 (m, 2H), 1.99 (s, 3H), 1.98 (s, 3H), 1.21 (d, J=6.7 Hz, 3H), 1.17 (d, J=6.6 Hz, 3H), 1.15 (s, 3H), 1.12 (s, 3H), 0.99 (s, 3H), 0.98 (s, 3H). LCMS: m/z 675.5 [M+H].

Compound 26

Compound 14a (455 mg, 0.674 mmol) was dissolved in 25 mL of anhydrous DCM under argon, and POCl$_3$ (0.630 mL, 6.76 mmol) was added. The mixture was stirred at RT for 18 h, after which time DCM and POCl$_3$ were removed in vacuo. The resulting oil was dissolved in 25 mL of anhydrous DCM, and the solution was cooled to 0° C., and DIEA (1.15 mL, 6.60 mmol) and 2-(2-aminoethoxy)ethanol (338 uL 3.37 mmol) were added. The mixture was allowed to warm to RT and stirred for 2 h, then extracted with saturated NaHCO$_3$. The extract was dried over Na$_2$SO$_4$. The crude product was chromatographed on silica gel (1"×6" column) using a gradient of MeOH/DCM (2 to 6% MeOH) to yield 382 mg (74%) of compound 26. $^1$H NMR (DMSO-$d_6$, 500 MHz): δ 8.00 (m, 1H), 7.60 (m, 2H), 6.99 (m, 1H), 6.43 (d, J=1.3 Hz, 2H), 6.32 (d, J=5.6 Hz, 2H), 4.41 (t, J=4.78, 1H), 4.16 (m, 4H), 3.29 (m, 2H), 3.15 (m, 6H), 3.09 (m, 4H), 2.90 (m, 2H), 1.98 (m, 6H), 1.09 (m, 9H), 0.97 (s, 3H), 0.85 (s, 3H), 0.72 (s, 3H). LCMS: m/z 762.6 [M+H].

Compound S10a

Compound 26 (367 mg, 0.481 mmol) was dissolved under argon in 20 mL of anhydrous DCM, and DIEA (0.419 mL, 2.41 mmol) was added, followed by N,N-diisopropylamino cyanoethyl phosphonamidic-Cl (0.129 mL, 0.627 mmol). The mixture was stirred at RT for 3 h, then extracted with saturated NaHCO$_3$, water, and brine. The extracts were dried over Na$_2$SO$_4$. Chromatography on silica gel (1"×6" column) with 20% EtOAc/hexanes to 30% EtOAc/hexanes containing 10% TEA yielded 350 mg (78%) of compound S10a. $^1$H NMR (CD$_3$CN, 500 MHz): δ 7.91 (m, 1H), 7.59 (m, 2H), 6.97 (m, 1H), 6.54 (d, J=8.2 Hz, 2H), 6.28 (s, 2H), 4.25 (m, 4H), 3.73 (m, 2H), 3.54 (m, 6H), 3.32 (m, 6H), 3.22 (m, 2H), 2.98 (m, 2H), 2.01 (s, 3H), 2.00 (s, 3H), 1.97 (pentet, J=2.5 Hz, 2H), 1.15 (m, 15H), 1.12 (s, 3H), 1.10 (s, 3H), 1.03 (s, 3H), 0.93 (m, 3H), 0.79 (s, 3H). 31P NMR (CD$_3$CN, 500 MHz): δ 148.2. LCMS: m/z 963.0 [M+H].

Compound S10b can be prepared from intermediate 12b in a similar manner.

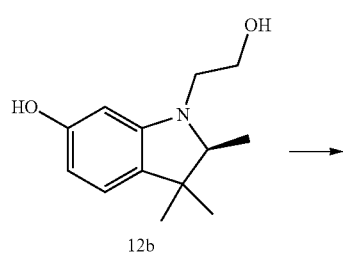

12b

S10b

Figure 3A:
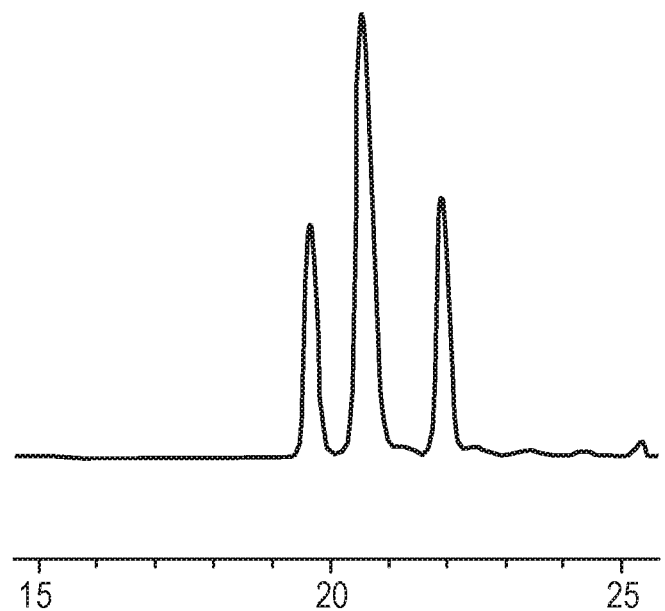
FIGS. 3A and 3B are HPLC traces of exemplary oligonucleotides labeled with racemic exemplary compound S10 (3A) and its isomer S10a (3B). In this figure, the x-axis is minutes, and the y-axis is absorbance at 260 nm.
Figure 3B:
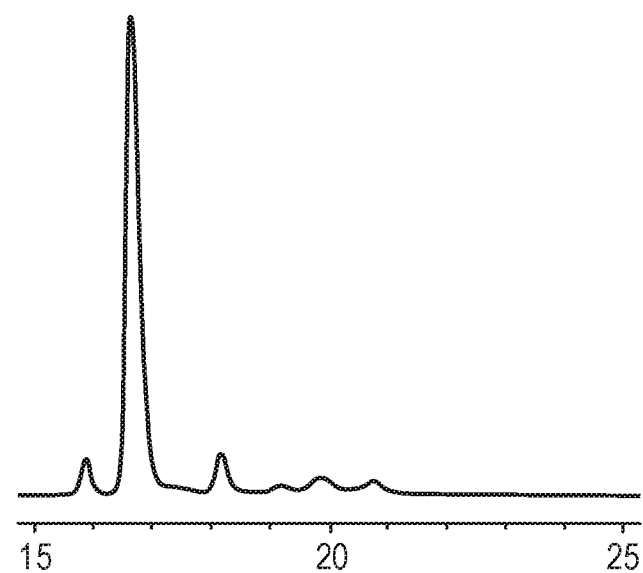

Exemplary labeled polynucleotides of SEQ. ID NO: 1 incorporating dyes S10 and S10a at the 5' ends were prepared by automated oligonucleotide synthesized as described above. The labeled polynucleotide incorporating dye S10 was purified by HPLC on Phenomenex Gemini column (5 μm C18 110 Å) eluting with a gradient of 16-34% ACN in 0.1 M triethylammonium bicarbonate buffer over 20 min. The labeled polynucleotide incorporating dye S10a was purified by HPLC on Phenomenex Gemini column (5 μm C18 110 Å) eluting with a gradient of 18-38% ACN in 0.1 M triethylammonium bicarbonate buffer over 20 min. The HPLC profiles of the two exemplary labeled polynucleotides are shown in FIGS. 3A and 3B.

Figure 1D:
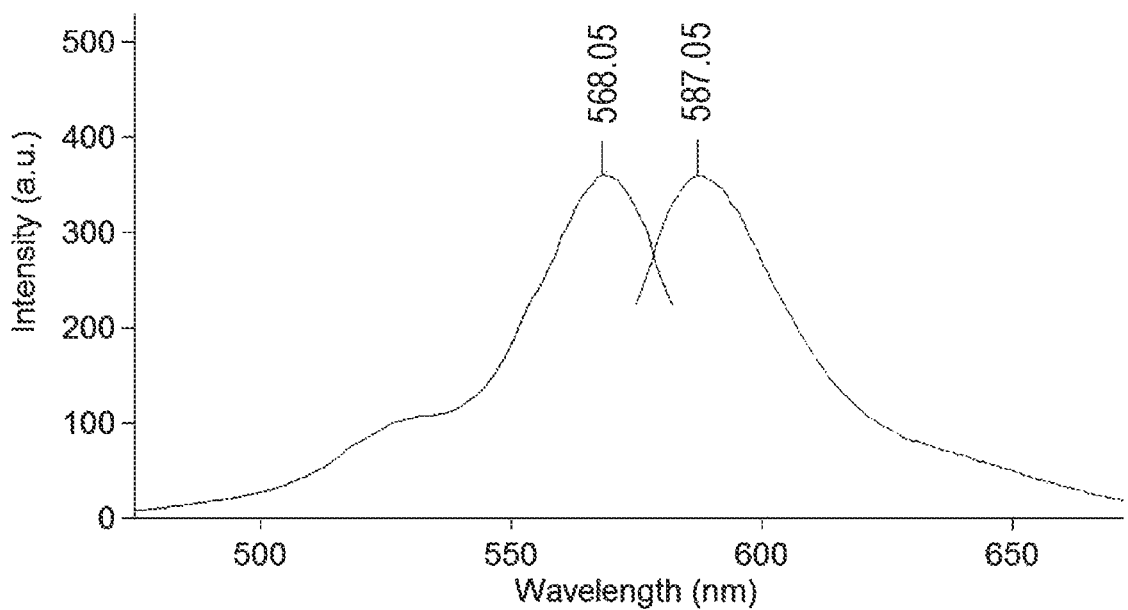
FIG. 1D depicts the excitation and emission spectra an exemplary polynucleotide SEQ ID NO: 1 5'-labeled with sulforhodamine dye S10a; Ex/Em max=568/587 nm.

FIG. 1D shows the emission/excitation spectrum of the S10a-labeled oligonucleotide SEQ. ID NO: 1 demonstrating that S10a could be used as a replacement for TAMRA dye. Moreover, as shown in FIG. 3B, the exemplary S10a-labeled polynucleotide produces predominantly a single peak by HPLC as compared to the multiple peaks produced by the exemplary S10-labeled polynucleotide (FIG. 3A), which simplifies chromatographic purification of such oligonucleotides.

The practice of the present disclosure can employ, unless otherwise indicated herein, conventional techniques of cell biology, molecular biology, microbiology, virology, recombinant DNA, and so forth which are within the skill of the art. Such techniques are explained fully in the literature. See e.g., Sambrook, Fritsch, and Maniatis, Molecular Cloning: A Laboratory Manual, Second Edition (1989), Oligonucleotide Synthesis (M. J. Gait Ed., 1984), Animal Cell Culture (R. I. Freshney, Ed., 1987), the series Methods In Enzymology (Academic Press, Inc.); Gene Transfer Vectors For Mammalian Cells (J. M. Miller and M. P. Calos eds. 1987), Current Protocols In Molecular Biology (F. M. Ausubel, R. Brent, R. E. Kingston, D. D. Moore, J. G. Siedman, J. A. Smith, and K. Struhl, eds., 1987).

While illustrative embodiments have been illustrated and described, it will be appreciated that various changes can be made therein without departing from the spirit and scope of the invention.

The invention claimed is:

1. A compound represented by Formula I:

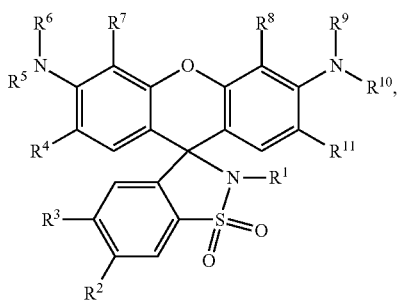

(I)

or a stereoisomer, tautomer, or salt thereof, wherein:
$R^1$ is $C_1$-$C_6$ alkyl or $L^1$-X;
$R^2$ is halogen or $SO_2NH_2$,
$R^3$ is H or halogen;
$R^4$, $R^7$, $R^8$, and $R^{11}$ when taken alone are independently H, halogen, or optionally substituted $C_1$-$C_6$ alkyl,
$R^5$, $R^6$, $R^9$, and $R^{10}$ when taken alone are independently H or optionally substituted $C_1$-$C_6$ alkyl;
$R^4$ and $R^5$ when taken together are an optionally substituted $C_2$-$C_3$ alkylene chain connecting the atoms to which $R^4$ and $R^5$ are attached;
$R^6$ and $R^7$ when taken together are an optionally substituted $C_2$-$C_3$ alkylene chain connecting the atoms to which $R^6$ and $R^7$ are attached;
$R^8$ and $R^9$ when taken together are an optionally substituted $C_2$-$C_3$ alkylene chain connecting the atoms to which $R^8$ and $R^9$ are attached;
$R^{10}$ and $R^{11}$ when taken together are an optionally substituted $C_2$-$C_3$ alkylene chain connecting the atoms to which $R^{10}$ and $R^{11}$ are attached;
$R^5$ and $R^6$, when taken together with the nitrogen atom to which $R^5$ and $R^6$ are attached, form a 5-membered or a 6-membered unsaturated ring;
$R^9$ and $R^{10}$, when taken together with the nitrogen atom to which $R^9$ and $R^{10}$ are attached, form a 5-membered or a 6-membered unsaturated ring;
$L^1$ is an optionally substituted $C_2$-$C_{10}$ alkylene or optionally substituted $C_2$-$C_{20}$ heteroalkylene;
X is —O—P(OCH$_2$CH$_2$CN)NR$^{12}$R$^{13}$ or

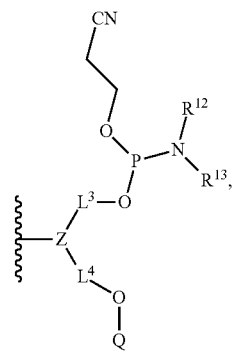

wherein
$L^3$ and $L^4$ are independently an optionally substituted $C_2$-$C_{10}$ alkylene or optionally substituted $C_2$-$C_{30}$ heteroalkylene;
Q is a hydroxyl protecting group;
Z is CH, N, NHC(O)N, or OC(O)N; and $R^{12}$ and $R^{13}$ are independently optionally substituted $C_1$-$C_6$ alkyl.

2. The compound of claim 1, wherein $R^2$ is $C_1$ and $R^3$ is H.

3. The compound of claim 1, wherein X is —OP(OCH$_2$CH$_2$CN)N(i-Pr)$_2$.

4. The compound of claim 1, wherein $L^1$ is a PEG$_{2-10}$ linker.

5. The compound of claim 1, wherein $L^1$ is —CH$_2$CH$_2$OCH$_2$CH$_2$—.

6. The compound of claim 1, wherein $R^4$ and $R^5$ taken together are an optionally substituted $C_3$ alkylene chain connecting the atoms to which $R^4$ and $R^5$ are attached; $R^{10}$ and $R^{11}$ taken together are an optionally substituted $C_3$ alkylene chain connecting the atoms to which $R^{10}$ and $R^{11}$ are attached; $R^6$ and $R^7$ taken together are an optionally substituted $C_3$ alkylene chain connecting the atoms to which $R^6$ and $R^7$ are attached; and $R^8$ and $R^9$ taken together are an optionally substituted $C_3$ alkylene chain connecting the atoms to which $R^8$ and $R^9$ are attached.

7. The compound of claim 1, wherein $R^4$ and $R^5$ taken together are a propylene chain connecting the atoms to which $R^4$ and $R^5$ are attached; $R^{10}$ and $R^{11}$ taken together are a propylene chain connecting the atoms to which $R^{10}$ and $R^{11}$ are attached; $R^6$ and $R^7$ taken together are a propylene chain connecting the atoms to which $R^6$ and $R^7$ are attached; and $R^8$ and $R^9$ taken together are a propylene chain connecting the atoms to which $R^8$ and $R^9$ are attached.

8. The compound of claim 1, wherein $R^5$, $R^6$, $R^9$, and $R^{10}$ are each methyl.

9. The compound of claim 1, wherein Q is an acid-labile hydroxyl protecting group.

10. The compound of claim 1, wherein Q is a trityl or dimethoxytrityl group.

11. The compound of claim 1, wherein $L^3$ and $L^4$ are independently $C_2$-$C_6$ alkylene or —(OCH$_2$CH$_2$)$_m$— wherein m is an integer ranging from 2 to 6.

12. The compound of claim 1, wherein $L^3$ and $L^4$ are independently CH$_2$CH$_2$.

13. The compound of claim 1, wherein X is:

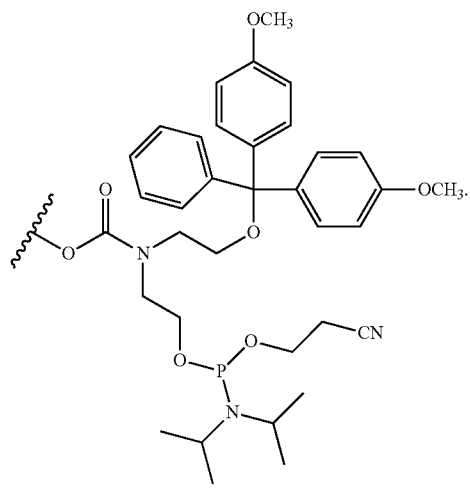 [SMILES: *OC(=O)N(CCOP(OCCC#N)N(C(C)C)C(C)C)CCOC(c1ccccc1)(c1ccc(OC)cc1)c1ccc(OC)cc1]

14. The compound of claim 1, wherein the compound is represented by Formula IA:

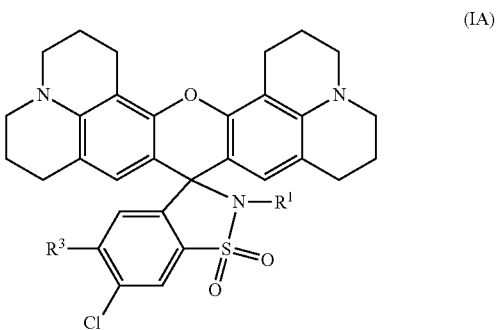

(IA)

or a stereoisomer, tautomer, or salt thereof, wherein $R^1$ is $L^1$X and $R^3$ is H or halogen.

15. The compound of claim 1, wherein the compound is:

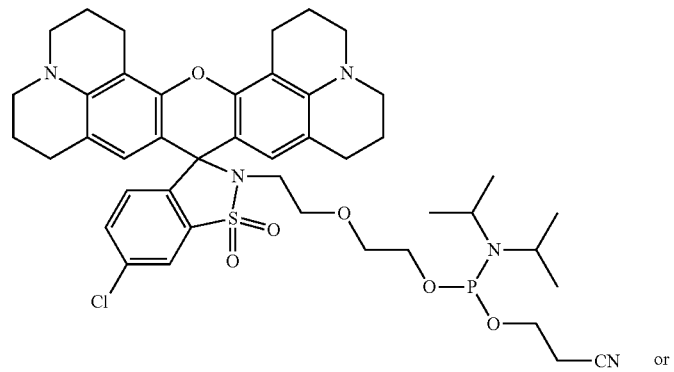

or

-continued
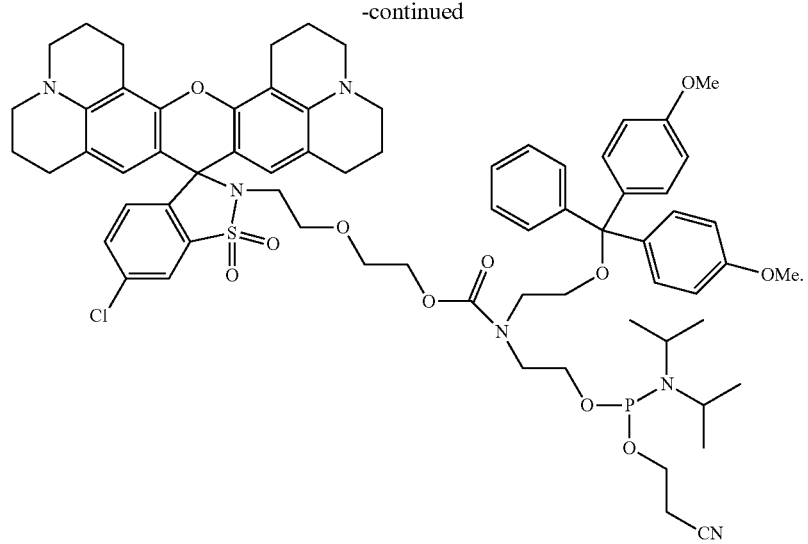
* * * * *